United States Patent
Kutchan et al.

(10) Patent No.: US 11,001,850 B2
(45) Date of Patent: May 11, 2021

(54) CONSTRUCTS AND METHODS FOR BIOSYNTHESIS OF CYCLOPAMINE

(71) Applicant: Donald Danforth Plant Science Center, St. Louis, MO (US)

(72) Inventors: Toni M Kutchan, St. Louis, MO (US); Megan Augustin, St. Louis, MO (US)

(73) Assignee: Donald Danforth Plant Science Center, St. Louis, MO (US)

( * ) Notice: Subject to any disclaimer, the term of this patent is extended or adjusted under 35 U.S.C. 154(b) by 0 days.

(21) Appl. No.: 15/391,190

(22) Filed: Dec. 27, 2016

(65) Prior Publication Data

US 2019/0185868 A1 Jun. 20, 2019

Related U.S. Application Data

(63) Continuation of application No. PCT/US2015/038062, filed on Jun. 26, 2015.

(60) Provisional application No. 62/018,556, filed on Jun. 28, 2014, provisional application No. 62/152,489, filed on Apr. 24, 2015.

(51) Int. Cl.
*C12N 15/82* (2006.01)
*A61K 31/4355* (2006.01)

(52) U.S. Cl.
CPC ...... *C12N 15/8243* (2013.01); *A61K 31/4355* (2013.01)

(58) Field of Classification Search
None
See application file for complete search history.

(56) References Cited

PUBLICATIONS

Simpson et al., 2010, γ-Aminobutyrate transaminase limits the catabolism of γ-aminobutyrate in cold-stressed *Arabidopsis* plants: insights from an overexpression mutant, Botany 88: 522-527.*
Cao et al., 2013, GABA transaminases from *Saccharomyces cerevisiae* and *Arabidopsis thaliana* complement function in cytosol and mitochondria, Yeast 30: 279-289.*
Sharp et al., 1986, Codon usage in yeast: cluster analysis clearly differentiates highly and lowly expressed genes, Nucleic Acids Research 14: 5125-5143.*
Veratrum californicum GABAT1v2 mRNA, GenBank Accession No. KJ869263, published May 8, 2015.*
Augustin et al., 2015, Elucidating steroid alkaloid biosynthesis in *Veratrum californicum*: production of verazine in Sf9 cells, The Plant Journal 82: 991-1003.*

* cited by examiner

*Primary Examiner* — Bratislav Stankovic
(74) *Attorney, Agent, or Firm* — Thompson Coburn LLP; William A. Holtz

(57) ABSTRACT

The present disclosure relates generally to the identification of enzymes within the cyclopamine biosynthesis pathway as well as to engineering transgenic plants or organisms for the production of cyclopamine.

20 Claims, 29 Drawing Sheets

Figures 1A, 1B:
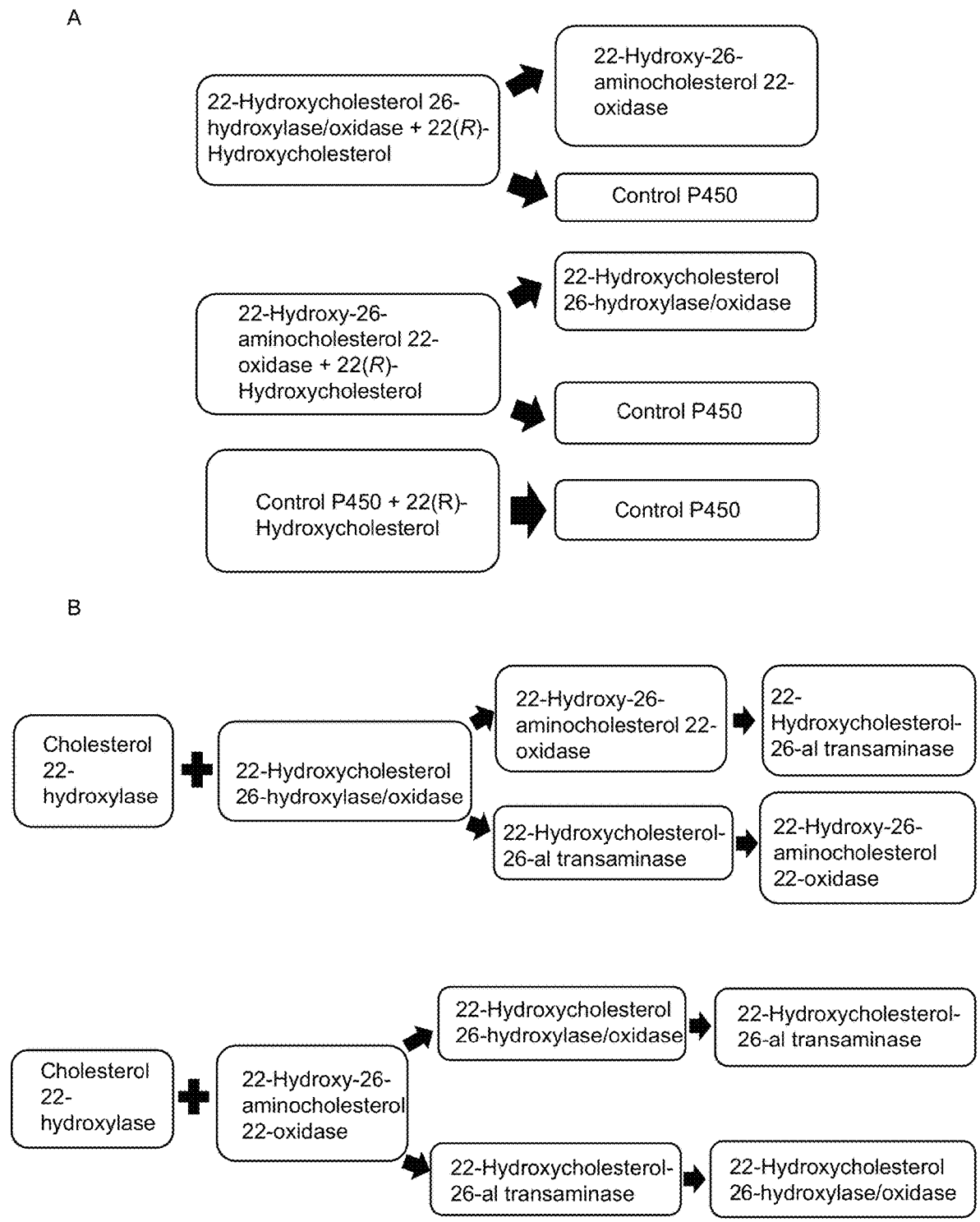

Specification includes a Sequence Listing.

C

D

SEQUENCE LISTING

<160> NUMBER OF SEQ ID NOS: 58

<210> SEQ ID NO 1
<211> LENGTH: 1455
<212> TYPE: DNA
<213> ORGANISM: Veratrum californicum

<400> SEQUENCE: 1

```
atggcgatgg agctcttatt gttgatccct gcgtttatcg tcgccatcat catcttcttc      60
agcttcaagt cgacaaacgg gacgtcgaca aaaccgctga aactcccgcc gggccaaatg     120
ggttggcctt tcatcggcca caccataccc ttcatgcagc cccactcctc cgcatccctc     180
ggtccctaca tcgacctcaa caccgccagg tatgggacta tatttcggat gaacttgttg     240
gcgaaaccga cgattgtgtc ggccgacccc gagttcaacc ggtacatact gcagaacgag     300
ggccggcttt tcgagaacag ctgcccgacg agcatcgcgg agatcatggg ccgttggtcg     360
atgctcgcgc tcaccggaga cgttcaccgc gagatgcggt ccatcgccgt cagcttcatg     420
```

-continued

```
agcaacgtca agctccggac ttacttcatc ggcgacatcg agcagcaggc cattaaagtc    480
ctcgcctcgt gggctggacg agacgctccc ttctcggccc aagatgaagg gaaaaagttt    540
gcattcaatc taatggtgaa gcatctaatg agcatggaac cgggcatgaa agagaccgag    600
cagttgagga gcgaatatca cgctttcatg aaggggatgg cgtcgatccc catcaacttg    660
cccggcaccg cctatagaaa agcgttgcag tcgaggtcca taatcctgaa gatcatgggc    720
gagaagctcg atgagcggat caagcaagtg aaagaaggct gcgagggcct cgagcaggac    780
gacctcctcg cctcggtctc caagcatccc aacctcgcca aggagcagat tctcgacctc    840
attctcagca tgctcttcgc cgggcacgaa acctcttctg ccgccatcgc cctcgccatc    900
tacttcctcg agtcctgccc taaagctgtc gagcagcttc gggaggagca taggagatc     960 gctagacaga agaaagaacg cggagagacc gggctcaact gggatgacta caagaaaatg   1020
gagttcaccc attgtgtcat caatgaaacc ctaagaatgg ggaacattgt gaagttcttg   1080
cataggagag ccatcaagga tgtgcagttc aaagggtatg acatcccatg tgggtgggaa   1140
gtggttccga tcatctcagc cgctcatctg gactcttcga tctacgatga cccacagcgg   1200
tacgatcctt ggaggtggca ggcgattttg gccggaaata ccaagaacaa caacgtgacg   1260
tcaatcatgt cattcagcgg cggaccccgg ctctgccccg cgccgagct ggcgaagctg    1320 gagatcgccg tattccttca ccacctcgtc cagaagtacc agtgggagat ggcggagcac   1380 gattacccccg tctccttccc gttcctcggc tttcccaagc gtttaccgat caaagttcgc   1440
cccctcggag actaa                                                    1455
```

<210> SEQ ID NO 2  
<211> LENGTH: 484  
<212> TYPE: PRT  
<213> ORGANISM: Veratrum californicum

<400> SEQUENCE: 2

```
Met Ala Met Glu Leu Leu Leu Ile Pro Ala Phe Ile Val Ala Ile
1               5                   10                  15

Ile Ile Phe Phe Ser Phe Lys Ser Thr Asn Gly Thr Ser Thr Lys Pro
            20                  25                  30

Leu Lys Leu Pro Pro Gly Gln Met Gly Trp Pro Phe Ile Gly His Thr
        35                  40                  45

Ile Pro Phe Met Gln Pro His Ser Ser Ala Ser Leu Gly Pro Tyr Ile
    50                  55                  60

Asp Leu Asn Thr Ala Arg Tyr Gly Thr Ile Phe Arg Met Asn Leu Leu
65                  70                  75                  80

Ala Lys Pro Thr Ile Val Ser Ala Asp Pro Glu Phe Asn Arg Tyr Ile
                85                  90                  95

Leu Gln Asn Glu Gly Arg Leu Phe Glu Asn Ser Cys Pro Thr Ser Ile
            100                 105                 110

Ala Glu Ile Met Gly Arg Trp Ser Met Leu Ala Leu Thr Gly Asp Val
        115                 120                 125

His Arg Glu Met Arg Ser Ile Ala Val Ser Phe Met Ser Asn Val Lys
    130                 135                 140

Leu Arg Thr Tyr Phe Ile Gly Asp Ile Glu Gln Gln Ala Ile Lys Val
145                 150                 155                 160

Leu Ala Ser Trp Ala Gly Arg Asp Ala Pro Phe Ser Ala Gln Asp Glu
                165                 170                 175

Gly Lys Lys Phe Ala Phe Asn Leu Met Val Lys His Leu Met Ser Met
            180                 185                 190
```

Glu Pro Gly Met Lys Glu Thr Glu Gln Leu Arg Ser Glu Tyr His Ala
            195                 200                 205

Phe Met Lys Gly Met Ala Ser Ile Pro Ile Asn Leu Pro Gly Thr Ala
    210                 215                 220

Tyr Arg Lys Ala Leu Gln Ser Arg Ser Ile Ile Leu Lys Ile Met Gly
225                 230                 235                 240

Glu Lys Leu Asp Glu Arg Ile Lys Gln Val Lys Glu Gly Cys Glu Gly
                245                 250                 255

Leu Glu Gln Asp Asp Leu Leu Ala Ser Val Ser Lys His Pro Asn Leu
            260                 265                 270

Ala Lys Glu Gln Ile Leu Asp Leu Ile Leu Ser Met Leu Phe Ala Gly
        275                 280                 285

His Glu Thr Ser Ser Ala Ala Ile Ala Leu Ala Ile Tyr Phe Leu Glu
    290                 295                 300

Ser Cys Pro Lys Ala Val Glu Gln Leu Arg Glu Glu His Lys Glu Ile
305                 310                 315                 320

Ala Arg Gln Lys Lys Glu Arg Gly Glu Thr Gly Leu Asn Trp Asp Asp
                325                 330                 335

Tyr Lys Lys Met Glu Phe Thr His Cys Val Ile Asn Glu Thr Leu Arg
            340                 345                 350

Met Gly Asn Ile Val Lys Phe Leu His Arg Arg Ala Ile Lys Asp Val
        355                 360                 365

Gln Phe Lys Gly Tyr Asp Ile Pro Cys Gly Trp Glu Val Val Pro Ile
    370                 375                 380

Ile Ser Ala Ala His Leu Asp Ser Ser Ile Tyr Asp Asp Pro Gln Arg
385                 390                 395                 400

Tyr Asp Pro Trp Arg Trp Gln Ala Ile Leu Ala Gly Asn Thr Lys Asn
                405                 410                 415

Asn Asn Val Thr Ser Ile Met Ser Phe Ser Gly Gly Pro Arg Leu Cys
            420                 425                 430

Pro Gly Ala Glu Leu Ala Lys Leu Glu Ile Ala Val Phe Leu His His
        435                 440                 445

Leu Val Gln Lys Tyr Gln Trp Glu Met Ala Glu His Asp Tyr Pro Val
    450                 455                 460

Ser Phe Pro Phe Leu Gly Phe Pro Lys Arg Leu Pro Ile Lys Val Arg
465                 470                 475                 480

Pro Leu Gly Asp

<210> SEQ ID NO 3
<211> LENGTH: 1455
<212> TYPE: DNA
<213> ORGANISM: Veratrum californicum

<400> SEQUENCE: 3
atggcgatgg agctcttatt gttgatccct gcgtttatcg tcgccatcat catcttcttc 60
agcttcaagt cgacaaacgg gacgtcgaca aaaccgctga aactcccgcc gggccaaatg 120
ggttggcctt tcatcggcca caccataccc ttcatgcagc cccactcctc cgcatccctc 180
ggtccctaca tcgacctcaa caccgccagg tatgggacta tatttcggat gaacttgttg 240
gcgaaaccga cgattgtgtc ggccgacccc gagttcaacc ggtacatact gcagaacgag 300
ggccggcttt tcgagaacag ctgcccgacg agcatcgcgg agatcatggg ccgttggtcg 360
atgctcgcgc tcaccggaga cgttcaccgc gagatgcggt ccatcgccgt cagcttcatg 420

-continued

```
agcaacgtca agctccggac ttacttcatc ggcgacatcg agcagcaggc cattaaagtc      480
ctcgcctcgt gggctggacg agacgctccc ttctcggccc aagatgaagg gaaaaagttt      540
gcgttcaatc taatggtgaa gcatctaatg agcatggaac cgggcatgaa agagaccgag      600
cagttgagga gcgaatatca cgctttcatg aaggggatgg catcgatccc catcaacttg      660
cccggcaccg cctatagaaa agcgttgcag tcgaggtcca taatcctgaa gatcatgggc      720
gagaagctcg atgagcggat caagcaagtg aaagaaggct gcgagggcct cgagcaggac      780
gacctcctcg cctcggtctc caagcatccc aacctcgcta aggagcagat tctcgacctc      840
attctcagca tgctcttcgc cgggcacgaa acctcttctg ccgccattgc cctcgccatc      900
tacttcctcg agtcctgccc taaagctgtc gagcagcttc ggggaggagca taaggagatc      960 gctagacaga agaaagaacg cggagagacc gggctcaact gggacgacta caagaaaatg     1020
gagttcaccc attgtgtcat caatgaaacc ctaagaatgg ggaacattgt gaagttcttg     1080
cataggagag ccatcaagga tgtgcagttc aaagggtatg acatcccatg tgggtgggaa     1140
gtggttccga tcatctcagc cgctcatctg gactcttcga tctacgatga cccacagcgg     1200
tacgatcctt ggaggtggca ggcgattttg gccggaaaata ccaagaacaa caacgtgatg     1260
tcaatcatgt cattcagcgg cggacccccgg ctttgccccg tgccgagct ggcgaagctg      1320 gagatcgccg tattccttca ccacctcgtc cagaagtacc agtgggagat ggcggagcac     1380
gattaccccg tctccttccc gttcctcggc tttcccaagc gtttaccgat caaagttcgc     1440
cccctcggag actaa                                                     1455
```

<210> SEQ ID NO 4
<211> LENGTH: 484
<212> TYPE: PRT
<213> ORGANISM: Veratrum californicum

<400> SEQUENCE: 4

```
Met Ala Met Glu Leu Leu Leu Ile Pro Ala Phe Ile Val Ala Ile
1               5                   10                  15

Ile Ile Phe Phe Ser Phe Lys Ser Thr Asn Gly Thr Ser Thr Lys Pro
                20                  25                  30

Leu Lys Leu Pro Pro Gly Gln Met Gly Trp Pro Phe Ile Gly His Thr
            35                  40                  45

Ile Pro Phe Met Gln Pro His Ser Ser Ala Ser Leu Gly Pro Tyr Ile
        50                  55                  60

Asp Leu Asn Thr Ala Arg Tyr Gly Thr Ile Phe Arg Met Asn Leu Leu
65                  70                  75                  80

Ala Lys Pro Thr Ile Val Ser Ala Asp Pro Glu Phe Asn Arg Tyr Ile
                85                  90                  95

Leu Gln Asn Glu Gly Arg Leu Phe Glu Asn Ser Cys Pro Thr Ser Ile
            100                 105                 110

Ala Glu Ile Met Gly Arg Trp Ser Met Leu Ala Leu Thr Gly Asp Val
        115                 120                 125

His Arg Glu Met Arg Ser Ile Ala Val Ser Phe Met Ser Asn Val Lys
    130                 135                 140

Leu Arg Thr Tyr Phe Ile Gly Asp Ile Glu Gln Gln Ala Ile Lys Val
145                 150                 155                 160

Leu Ala Ser Trp Ala Gly Arg Asp Ala Pro Phe Ser Ala Gln Asp Glu
                165                 170                 175

Gly Lys Lys Phe Ala Phe Asn Leu Met Val Lys His Leu Met Ser Met
            180                 185                 190
```

```
Glu Pro Gly Met Lys Glu Thr Glu Gln Leu Arg Ser Glu Tyr His Ala
        195                 200                 205

Phe Met Lys Gly Met Ala Ser Ile Pro Ile Asn Leu Pro Gly Thr Ala
    210                 215                 220

Tyr Arg Lys Ala Leu Gln Ser Arg Ser Ile Ile Leu Lys Ile Met Gly
225                 230                 235                 240

Glu Lys Leu Asp Glu Arg Ile Lys Gln Val Lys Glu Gly Cys Glu Gly
                245                 250                 255

Leu Glu Gln Asp Asp Leu Leu Ala Ser Val Ser Lys His Pro Asn Leu
            260                 265                 270

Ala Lys Glu Gln Ile Leu Asp Leu Ile Leu Ser Met Leu Phe Ala Gly
        275                 280                 285

His Glu Thr Ser Ser Ala Ala Ile Ala Leu Ala Ile Tyr Phe Leu Glu
    290                 295                 300

Ser Cys Pro Lys Ala Val Glu Gln Leu Arg Glu Glu His Lys Glu Ile
305                 310                 315                 320

Ala Arg Gln Lys Lys Glu Arg Gly Glu Thr Gly Leu Asn Trp Asp Asp
                325                 330                 335

Tyr Lys Lys Met Glu Phe Thr His Cys Val Ile Asn Glu Thr Leu Arg
            340                 345                 350

Met Gly Asn Ile Val Lys Phe Leu His Arg Arg Ala Ile Lys Asp Val
        355                 360                 365

Gln Phe Lys Gly Tyr Asp Ile Pro Cys Gly Trp Glu Val Val Pro Ile
    370                 375                 380

Ile Ser Ala Ala His Leu Asp Ser Ser Ile Tyr Asp Asp Pro Gln Arg
385                 390                 395                 400

Tyr Asp Pro Trp Arg Trp Gln Ala Ile Leu Ala Gly Asn Thr Lys Asn
                405                 410                 415

Asn Asn Val Met Ser Ile Met Ser Phe Ser Gly Gly Pro Arg Leu Cys
            420                 425                 430

Pro Gly Ala Glu Leu Ala Lys Leu Glu Ile Ala Val Phe Leu His His
        435                 440                 445

Leu Val Gln Lys Tyr Gln Trp Glu Met Ala Glu His Asp Tyr Pro Val
    450                 455                 460

Ser Phe Pro Phe Leu Gly Phe Pro Lys Arg Leu Pro Ile Lys Val Arg
465                 470                 475                 480

Pro Leu Gly Asp

<210> SEQ ID NO 5
<211> LENGTH: 1545
<212> TYPE: DNA
<213> ORGANISM: Veratrum californicum

<400> SEQUENCE: 5
atggatctac cctccgcctc agccgccgtc gccgccgcta ccgctgccgt aatcttcctc      60
ctcactatct acctcctccc gaagaaaaaa tctccggcgt cgaccggaaa gaacggatcc     120
acatccctgg agagctaccc agtaatcggc aacctccccc acttcgtcaa gaaccgcaac     180
cgcttcctcg actgggtggc ggaaataata tcccagagcc ccaccggcac cgtcatcgcc     240
gaccccttgg tcttcacctc caaccccgag aacgtcgagc acaccgccaa gtcccgcttc     300
gacgcctacg cccgcggccc cgccgccacc gccgtcctcc acgacttcct cggcagcggc     360
atcctcaacg tcgacggcga cagctggcgg gcccagcgga agaccgccag ctccgagttc     420
```

```
accacccgct ccctccgcgc cttcatcctc gacgccgtcg acggcgaggc cgccggccgg      480
ctcctccccc tcctctcccg cgccgctgcc tccggcgagg tgttcgacct ccaggacgtc      540
ctcgagcggt tcgccttcga caacatctgc agcatcatct tcgacgccga ccccaactgc      600
ctcaacgaca cccacgacgg cgtcggcgag cgcttctacc acgccttcca cgacgccacc      660
ctgctctcca ccgggaggta ctactacccc ttccactggg tctggaggct cctgcgttgg      720
ctcaacctcg gcacagaaaa gcgactgcgc gatgcggtgt cggacgttca caaggcgatc      780
gacgaattgg tcgggtcccg gaagacggag gtcgggacga cggtgcggcg cagggcggc      840 gggagcgacc tcctctcgag gttcgcggag ggcggggatt actccgacga cgtcctccgc      900
gacgtgctca tcaacttcgt cctcgccggc cgcgacacca ccccctcggc gctcacctgg      960 ttcttttca tgatctcgtc gcggcccgac gtggtggacc agatcctcga cgagatccga      1020
tcgatccgag atcatcagga ccgtagcaac ccgaacggcg gaggcggtgg tttcacgctg      1080
gaggagctga gggagatgaa ttacctccac gcggcgataa cggagtcgct ccggctcaac      1140
ccgccggtgc cgctgatgcc taagatgtgc atggaggacg acgtgctgcc ggacgggacc      1200
gtggtgcggc gggggtggac ggtgatgtac agcgcgttcg cgatggggag aaggcggaa      1260 atttgggggg aggattgcat ggagttcaag ccggagcgtt gtctggacga cggaggctgt      1320
tttaagtcgg cgagcgcgta tcggcttccg gcgttccacg cgggtccgag gatttgcttg      1380
gggaaggaca tggcctacat ccagatgaag gcggtggcgt cgagcatgct cgagaggttc      1440
gaggtggagg ttgtggagaa gcgcgggaag cccgagctgt cgatcacgat gaggatggat      1500
agggggctgc cggtgaggat caaggagagg aagagagggt gttag                     1545
```

<210> SEQ ID NO 6
<211> LENGTH: 514
<212> TYPE: PRT
<213> ORGANISM: Veratrum californicum

<400> SEQUENCE: 6

```
Met Asp Leu Pro Ser Ala Ser Ala Ala Val Ala Ala Thr Ala Ala
1               5                   10                  15

Val Ile Phe Leu Leu Thr Ile Tyr Leu Leu Pro Lys Lys Lys Ser Pro
            20                  25                  30

Ala Ser Thr Gly Lys Asn Gly Ser Thr Ser Leu Glu Ser Tyr Pro Val
        35                  40                  45

Ile Gly Asn Leu Pro His Phe Val Lys Asn Arg Asn Arg Phe Leu Asp
    50                  55                  60

Trp Val Ala Glu Ile Ile Ser Gln Ser Pro Thr Gly Thr Val Ile Ala
65                  70                  75                  80

Asp Pro Leu Val Phe Thr Ser Asn Pro Glu Asn Val Glu His Thr Ala
                85                  90                  95

Lys Ser Arg Phe Asp Ala Tyr Ala Arg Gly Pro Ala Ala Thr Ala Val
            100                 105                 110

Leu His Asp Phe Leu Gly Ser Gly Ile Leu Asn Val Asp Gly Asp Ser
        115                 120                 125

Trp Arg Ala Gln Arg Lys Thr Ala Ser Ser Glu Phe Thr Thr Arg Ser
    130                 135                 140

Leu Arg Ala Phe Ile Leu Asp Ala Val Asp Gly Glu Ala Ala Gly Arg
145                 150                 155                 160

Leu Leu Pro Leu Leu Ser Arg Ala Ala Ala Ser Gly Glu Val Phe Asp
                165                 170                 175
```

-continued

```
Leu Gln Asp Val Leu Glu Arg Phe Ala Phe Asp Asn Ile Cys Ser Ile
            180                 185                 190

Ile Phe Asp Ala Asp Pro Asn Cys Leu Asn Asp Thr His Asp Gly Val
        195                 200                 205

Gly Glu Arg Phe Tyr His Ala Phe His Asp Ala Thr Leu Leu Ser Thr
    210                 215                 220

Gly Arg Tyr Tyr Tyr Pro Phe His Trp Val Trp Arg Leu Leu Arg Trp
225                 230                 235                 240

Leu Asn Leu Gly Thr Glu Lys Arg Leu Arg Asp Ala Val Ser Asp Val
                245                 250                 255

His Lys Ala Ile Asp Glu Leu Val Gly Ser Arg Lys Thr Glu Val Gly
            260                 265                 270

Thr Thr Val Arg Arg Gln Gly Gly Gly Ser Asp Leu Leu Ser Arg Phe
        275                 280                 285

Ala Glu Gly Gly Asp Tyr Ser Asp Asp Val Leu Arg Asp Val Leu Ile
    290                 295                 300

Asn Phe Val Leu Ala Gly Arg Asp Thr Thr Pro Ser Ala Leu Thr Trp
305                 310                 315                 320

Phe Phe Phe Met Ile Ser Ser Arg Pro Asp Val Val Asp Gln Ile Leu
                325                 330                 335

Asp Glu Ile Arg Ser Ile Arg Asp His Gln Asp Arg Ser Asn Pro Asn
            340                 345                 350

Gly Gly Gly Gly Gly Phe Thr Leu Glu Glu Leu Arg Glu Met Asn Tyr
        355                 360                 365

Leu His Ala Ala Ile Thr Glu Ser Leu Arg Leu Asn Pro Pro Val Pro
    370                 375                 380

Leu Met Pro Lys Met Cys Met Glu Asp Asp Val Leu Pro Asp Gly Thr
385                 390                 395                 400

Val Val Arg Arg Gly Trp Thr Val Met Tyr Ser Ala Phe Ala Met Gly
                405                 410                 415

Arg Lys Ala Glu Ile Trp Gly Glu Asp Cys Met Glu Phe Lys Pro Glu
            420                 425                 430

Arg Cys Leu Asp Asp Gly Gly Cys Phe Lys Ser Ala Ser Ala Tyr Arg
        435                 440                 445

Leu Pro Ala Phe His Ala Gly Pro Arg Ile Cys Leu Gly Lys Asp Met
    450                 455                 460

Ala Tyr Ile Gln Met Lys Ala Val Ala Ser Ser Met Leu Glu Arg Phe
465                 470                 475                 480

Glu Val Glu Val Val Glu Lys Arg Gly Lys Pro Glu Leu Ser Ile Thr
                485                 490                 495

Met Arg Met Asp Arg Gly Leu Pro Val Arg Ile Lys Glu Arg Lys Arg
            500                 505                 510

Gly Cys
```

<210> SEQ ID NO 7
<211> LENGTH: 1545
<212> TYPE: DNA
<213> ORGANISM: Veratrum californicum

<400> SEQUENCE: 7

```
atggatctac cctccgcctc agccgccgtc gccgccgcta ccgctgccgt aatcttcctc      60
ctcactatct acctcctccc gaagaaaaaa tctccggcgt cgaccggaaa gaacggatcc     120
acatccctgg agagctaccc agtaatcggc aacctccccc acttcgtcaa gaaccgcaac     180
```

```
cgcttcctcg actgggtggc ggaaataata tcccagagcc ccaccggcac cgtcatcgcc    240
gccccccttgg tcttcacctc caaccccgag aacgtcgagc acaccgccaa gtcccgcttc    300
gacgcctacg cccgcggccc cgccgccacc gccgtcctcc acgacttcct cggcagcggc    360
atcctcaacg tcgacggcga cagctggcgg gcccagcgga agaccgccag ctccgagttc    420
accaccgct ccctccgcgc cttcatcctc gacgccgtcg acggcgaggc cgccggccgg    480
ctcctcccc tcctctcccg cgccgctgcc tccggcgagg tgttcgacct ccaggacgtc    540
ctcgagcggt tcgccttcga caacatctgc agcatcatct tcgacgccga ccccaactgc    600
ctcaacgaca cccacgacgg cgtcggcgag cgcttctacc acgccttcca cgacgccacc    660
ctgctctcca ccgggaggta ctactacccc ttccactggg tctggaggct cctgcgttgg    720
ctcaacctcg ggacagaaaa gcgactcgcg gatgcggtgt cggacgttca caaggcgatc    780
gacgaattgg tcgggtcccg gaagacggag gtcgggacga cggtgcggcg gcagggcggc    840
gggagcgacc tcctctcgag gttcgcggag ggcggggatt actccgacga cgtcctccgc    900
gacgtgctca tcaacttcgt cctcgccggc cgcgacacca ccccctcggc gctcacctgg    960
ttctttttca tgatctcgtc gcggcccgac gtggtggacc agatcctcga cgagatccga    1020
tcgatccgag atcatcagga ccgtagcaac ccgaacggcg gaggcggtgg tttcacgctg    1080
gaggagctga gggagatgaa ttacctccac gcggcgataa cggagtcgct ccggctcaac    1140
ccgccggtgc cgctgatgcc taagatgtgc atgaggacga cgtgctgcc ggacgggacc    1200
gtggtgcggc ggggtggac ggtgatgtac agcgcgttcg cgatggggag gaaggcggaa    1260
atttgggggg aggattgcat ggagttcaag ccggagcgtt ggctggacga cggaggctgt    1320
tttaagtcgg cgagcgcgta tcggcttccg gcgttccacg cgggtccgag gatttgcttg    1380
gggaaggaca tggcctacat ccagatgaag gcagtggcat cgagcttgct cgagaggttc    1440
gaggtcgagg tggtggagaa gcgagggaag cccgagctgt cgatcacgat gaggatggat    1500
agggggctgc cggtgagggt caaggagagg aagagagggt gttag               1545
```

<210> SEQ ID NO 8
<211> LENGTH: 514
<212> TYPE: PRT
<213> ORGANISM: Veratrum californicum

<400> SEQUENCE: 8

```
Met Asp Leu Pro Ser Ala Ser Ala Ala Val Ala Ala Ala Thr Ala Ala
1               5                   10                  15

Val Ile Phe Leu Leu Thr Ile Tyr Leu Leu Pro Lys Lys Lys Ser Pro
            20                  25                  30

Ala Ser Thr Gly Lys Asn Gly Ser Thr Ser Leu Glu Ser Tyr Pro Val
        35                  40                  45

Ile Gly Asn Leu Pro His Phe Val Lys Asn Arg Asn Arg Phe Leu Asp
    50                  55                  60

Trp Val Ala Glu Ile Ile Ser Gln Ser Pro Thr Gly Thr Val Ile Ala
65                  70                  75                  80

Ala Pro Leu Val Phe Thr Ser Asn Pro Glu Asn Val Glu His Thr Ala
                85                  90                  95

Lys Ser Arg Phe Asp Ala Tyr Ala Arg Gly Pro Ala Ala Thr Ala Val
            100                 105                 110

Leu His Asp Phe Leu Gly Ser Gly Ile Leu Asn Val Asp Gly Asp Ser
        115                 120                 125

Trp Arg Ala Gln Arg Lys Thr Ala Ser Ser Glu Phe Thr Thr Arg Ser
```

```
                130                 135                 140
Leu Arg Ala Phe Ile Leu Asp Ala Val Asp Gly Glu Ala Ala Gly Arg
145                 150                 155                 160

Leu Leu Pro Leu Leu Ser Arg Ala Ala Ala Ser Gly Glu Val Phe Asp
                165                 170                 175

Leu Gln Asp Val Leu Glu Arg Phe Ala Phe Asp Asn Ile Cys Ser Ile
                180                 185                 190

Ile Phe Asp Ala Asp Pro Asn Cys Leu Asn Asp Thr His Asp Gly Val
                195                 200                 205

Gly Glu Arg Phe Tyr His Ala Phe His Asp Ala Thr Leu Leu Ser Thr
                210                 215                 220

Gly Arg Tyr Tyr Tyr Pro Phe His Trp Val Trp Arg Leu Leu Arg Trp
225                 230                 235                 240

Leu Asn Leu Gly Thr Glu Lys Arg Leu Arg Asp Ala Val Ser Asp Val
                245                 250                 255

His Lys Ala Ile Asp Glu Leu Val Gly Ser Arg Lys Thr Glu Val Gly
                260                 265                 270

Thr Thr Val Arg Arg Gln Gly Gly Gly Ser Asp Leu Leu Ser Arg Phe
                275                 280                 285

Ala Glu Gly Gly Asp Tyr Ser Asp Asp Val Leu Arg Asp Val Leu Ile
                290                 295                 300

Asn Phe Val Leu Ala Gly Arg Asp Thr Thr Pro Ser Ala Leu Thr Trp
305                 310                 315                 320

Phe Phe Phe Met Ile Ser Ser Arg Pro Asp Val Val Asp Gln Ile Leu
                325                 330                 335

Asp Glu Ile Arg Ser Ile Arg Asp His Gln Asp Arg Ser Asn Pro Asn
                340                 345                 350

Gly Gly Gly Gly Phe Thr Leu Glu Glu Leu Arg Glu Met Asn Tyr
                355                 360                 365

Leu His Ala Ala Ile Thr Glu Ser Leu Arg Leu Asn Pro Pro Val Pro
                370                 375                 380

Leu Met Pro Lys Met Cys Met Glu Asp Asp Val Leu Pro Asp Gly Thr
385                 390                 395                 400

Val Val Arg Arg Gly Trp Thr Val Met Tyr Ser Ala Phe Ala Met Gly
                405                 410                 415

Arg Lys Ala Glu Ile Trp Gly Glu Asp Cys Met Glu Phe Lys Pro Glu
                420                 425                 430

Arg Trp Leu Asp Asp Gly Gly Cys Phe Lys Ser Ala Ser Ala Tyr Arg
                435                 440                 445

Leu Pro Ala Phe His Ala Gly Pro Arg Ile Cys Leu Gly Lys Asp Met
450                 455                 460

Ala Tyr Ile Gln Met Lys Ala Val Ala Ser Leu Leu Glu Arg Phe
465                 470                 475                 480

Glu Val Glu Val Val Glu Lys Arg Gly Lys Pro Glu Leu Ser Ile Thr
                485                 490                 495

Met Arg Met Asp Arg Gly Leu Pro Val Arg Val Lys Glu Arg Lys Arg
                500                 505                 510

Gly Cys

<210> SEQ ID NO 9
<211> LENGTH: 1545
<212> TYPE: DNA
<213> ORGANISM: Veratrum californicum
```

-continued

<400> SEQUENCE: 9

```
atggatctac cctccgcctc agccgccgtc gcc

```
Lys Ser Arg Phe Asp Thr Tyr Ser Arg Gly Pro Ala Ala Thr Ala Val
            100                 105                 110

Leu His Asp Phe Leu Gly Ser Gly Ile Leu Asn Val Asp Gly Glu Ser
            115                 120                 125

Trp Arg Ala Gln Arg Lys Thr Ala Ser Ser Glu Phe Thr Thr Arg Ser
            130                 135                 140

Leu Arg Ala Phe Ile Leu Asp Ala Val Asp Gly Glu Ala Ala Gly Arg
145                 150                 155                 160

Leu Leu Pro Leu Leu Ser Arg Ala Ala Ser Gly Glu Val Leu Asp
            165                 170                 175

Leu Gln Asp Val Leu Glu Arg Phe Ala Phe Asp Asn Ile Cys Ser Ile
            180                 185                 190

Ile Phe Asp Ala Asp Pro Asn Cys Leu Asn Asp Thr His Asp Gly Val
            195                 200                 205

Gly Glu Arg Phe Tyr His Ala Phe His Asp Ala Thr Leu Leu Ser Thr
            210                 215                 220

Gly Arg Tyr Tyr Tyr Pro Phe His Trp Val Trp Arg Leu Leu Arg Trp
225                 230                 235                 240

Leu Asn Leu Gly Asn Glu Lys Arg Leu Arg Asp Ala Val Ser Asp Val
            245                 250                 255

His Lys Ala Ile Asp Glu Leu Val Gly Ser Arg Arg Thr Glu Val Gly
            260                 265                 270

Thr Thr Val Arg Arg Gln Gly Gly Ser Asp Leu Leu Ser Arg Phe
            275                 280                 285

Ala Glu Ser Gly Asp Tyr Ser Asp Asp Val Leu Arg Asp Val Leu Ile
            290                 295                 300

Asn Phe Val Leu Ala Gly Arg Asp Thr Thr Pro Ser Ala Leu Thr Trp
305                 310                 315                 320

Phe Phe Phe Ser Ile Ser Leu Arg Pro Asp Val Val Asp Lys Ile Leu
            325                 330                 335

Asp Glu Ile Arg Ser Ile Arg Asp Arg Gln Asp Arg Asn Asn Pro Asn
            340                 345                 350

Ser Gly Gly Gly Gly Phe Thr Leu Glu Glu Leu Arg Glu Met Asn Tyr
            355                 360                 365

Leu His Ala Ala Ile Thr Glu Ser Leu Arg Leu Asn Pro Pro Val Pro
            370                 375                 380

Leu Met Pro Lys Met Cys Met Glu Asp Asp Val Leu Pro Asp Gly Thr
385                 390                 395                 400

Val Val Arg Arg Gly Trp Thr Val Met Tyr Ser Ala Phe Val Met Gly
            405                 410                 415

Arg Lys Ala Glu Ile Trp Gly Glu Asp Cys Met Glu Phe Lys Pro Glu
            420                 425                 430

Arg Trp Leu Asp Asp Gly Gly Cys Phe Lys Ser Ala Ser Ala Tyr Arg
            435                 440                 445

Leu Pro Ala Phe His Ala Gly Pro Arg Ile Cys Leu Gly Lys Asp Met
            450                 455                 460

Ala Tyr Ile Gln Met Lys Ala Val Ala Ser Ser Met Leu Glu Arg Phe
465                 470                 475                 480

Glu Val Glu Val Val Glu Lys Arg Gly Lys Pro Glu Leu Ser Ile Thr
            485                 490                 495

Met Arg Met Asp Arg Gly Leu Pro Val Arg Ile Lys Glu Arg Lys Arg
            500                 505                 510
```

Gly Cys

<210> SEQ ID NO 11
<211> LENGTH: 1478
<212> TYPE: DNA
<213> ORGANISM: Veratrum californicum

<400> SEQUENCE: 11

```
tctacctcct cacgaagcaa aagtctccgg cgacgaccgg gaacagcgga tccacatccc    60
tgaagagcta cccaataatc ggaaacctcc cccacttcgt caagaaccgc aaccgcttcc   120
tcgactgggt ggcggagatc atctccctca gccccaccga caccgtcatc gccacccccct  180
tggtcttcac cgccaacccc gacaacgtcg agcacaccgc caagtcccgc ttcgacacct   240
actcccgcgg ccccgccgcc accgccgtcc tccacgactt cctcggcagc ggcatcctca   300
acgtcgacgg cgaaagctgg cgggcccagc ggaagaccgc cagctccgag ttcaccaccc   360
gctcccctccg cgccttcatc ctcgacgccc tcgacggcga ggccgccggc cggctgctcc   420
ccctcctctc ccgcgccgcc gcctccggcg aggtgctcga cctccaggac gtcctcgagc   480
ggttcgcctt tgacaacatc tgcagcatca tcttcgacgc cgaccccaac tgcctcaacg   540
acacccacga cggcgtcggc gagcgcttct accacgcctt ccacgatgcc accctgctct   600
ccaccgggag gtactactac cccttccact gggtctggag gctcctgcgt tggctcaacc   660
ttgggaacga aaagcggctg cgcgacgcgg tgtcggacgt ccacaaggcg atcgatgaat   720
tggtcgggtc ccggaggacg gaggtcggga cgacggtgcg gcggcagggc ggcgggagcg   780
acctcctctc tagattcgcg gagagtgggg attactccga cgacgtcctc cgcgacgtgc   840
tcatcaactt cgtcctcgct ggccgcgaca ccacccccctc cgcactaacc tggttctttt   900
tctcgatctc attgcggccc gacgtggtgg acaagatcct cgacgagatc cgatcgatcc   960
gggatcgtca ggaccgtaac aacccgaaca gcggaggcgg cggtttcacg ctggaggagc  1020
tgagggagat gaattacctc cacgctgcga taacggagtc gctcaggctc aacccgccgg  1080
tgccgctgat gcctaagatg tgcatggagg acgacgtgct gcccgacggg acggtggtgc  1140
ggcgggggtg gacggtgatg tacagcgcgt tcgtgatggg gaggaaggcg gaaatatggg  1200
gggaggattg catggagttc aagccggagc ggtggctgga cgacggaggt tgttttaagt  1260
cggcgagcgc gtatcggctt ccggcgttcc acgcgggtcc gaggatttgc ttggggaagg  1320
acatggccta catccagatg aaggcggtgg cgtcgagcat gctcgagagg ttcgaggtgg  1380
aggttgtgga gaagcgcggg aagcccgagc tgtcgatcac gatgaggatg gatagggggc  1440
tgccggtgag gatcaaggag aggaagagag ggtgttag                          1478
```

<210> SEQ ID NO 12
<211> LENGTH: 511
<212> TYPE: PRT
<213> ORGANISM: Veratrum californicum

<400> SEQUENCE: 12

```
Met Asp Leu Pro Ser Ala Thr Ser Val Ala Ala Ala Leu Ile Ile
1               5                   10                  15

Leu Leu Thr Ile Tyr Leu Leu Thr Lys Gln Lys Ser Pro Ala Thr Thr
            20                  25                  30

Gly Asn Ser Gly Ser Thr Ser Leu Lys Ser Tyr Pro Ile Ile Gly Asn
        35                  40                  45

Leu Pro His Phe Val Lys Asn Arg Asn Arg Phe Leu Asp Trp Val Ala
    50                  55                  60
```

```
Glu Ile Ile Ser Leu Ser Pro Thr Asp Thr Val Ile Ala Thr Pro Leu
 65                  70                  75                  80

Val Phe Thr Ala Asn Pro Asp Asn Val Glu His Thr Ala Lys Ser Arg
                 85                  90                  95

Phe Asp Thr Tyr Ser Arg Gly Pro Ala Ala Thr Ala Val Leu His Asp
            100                 105                 110

Phe Leu Gly Ser Gly Ile Leu Asn Val Asp Gly Glu Ser Trp Arg Ala
        115                 120                 125

Gln Arg Lys Thr Ala Ser Ser Glu Phe Thr Thr Arg Ser Leu Arg Ala
    130                 135                 140

Phe Ile Leu Asp Ala Val Asp Gly Glu Ala Ala Gly Arg Leu Leu Pro
145                 150                 155                 160

Leu Leu Ser Arg Ala Ala Ala Ser Gly Glu Val Leu Asp Leu Gln Asp
                165                 170                 175

Val Leu Glu Arg Phe Ala Phe Asp Asn Ile Cys Ser Ile Ile Phe Asp
            180                 185                 190

Ala Asp Pro Asn Cys Leu Asn Asp Thr His Asp Gly Val Gly Glu Arg
        195                 200                 205

Phe Tyr His Ala Phe His Asp Ala Thr Leu Leu Ser Thr Gly Arg Tyr
    210                 215                 220

Tyr Tyr Pro Phe His Trp Val Trp Arg Leu Leu Arg Trp Leu Asn Leu
225                 230                 235                 240

Gly Asn Glu Lys Arg Leu Arg Asp Ala Val Ser Asp Val His Lys Ala
                245                 250                 255

Ile Asp Glu Leu Val Gly Ser Arg Arg Thr Glu Val Gly Thr Thr Val
            260                 265                 270

Arg Arg Gln Gly Gly Gly Ser Asp Leu Leu Ser Arg Phe Ala Glu Ser
        275                 280                 285

Gly Asp Tyr Ser Asp Asp Val Leu Arg Asp Val Leu Ile Asn Phe Val
    290                 295                 300

Leu Ala Gly Arg Asp Thr Thr Pro Ser Ala Leu Thr Trp Phe Phe Phe
305                 310                 315                 320

Ser Ile Ser Leu Arg Pro Asp Val Val Asp Lys Ile Leu Asp Glu Ile
                325                 330                 335

Arg Ser Ile Arg Asp Arg Gln Asp Arg Asn Asn Pro Asn Ser Gly Gly
            340                 345                 350

Gly Gly Phe Thr Leu Glu Glu Leu Arg Glu Met Asn Tyr Leu His Ala
        355                 360                 365

Ala Ile Thr Glu Ser Leu Arg Leu Asn Pro Pro Val Pro Leu Met Pro
    370                 375                 380

Lys Met Cys Met Glu Asp Asp Val Leu Pro Asp Gly Thr Val Val Arg
385                 390                 395                 400

Arg Gly Trp Thr Val Met Tyr Ser Ala Phe Val Met Gly Arg Lys Ala
                405                 410                 415

Glu Ile Trp Gly Glu Asp Cys Met Glu Phe Lys Pro Glu Arg Trp Leu
            420                 425                 430

Asp Asp Gly Gly Cys Phe Lys Ser Ala Ser Ala Tyr Arg Leu Pro Ala
        435                 440                 445

Phe His Ala Gly Pro Arg Ile Cys Leu Gly Lys Asp Met Ala Tyr Ile
    450                 455                 460

Gln Met Lys Ala Val Ala Ser Ser Met Leu Glu Arg Phe Glu Val Glu
465                 470                 475                 480
```

```
Val Val Glu Lys Arg Gly Lys Pro Glu Leu Ser Ile Thr Met Arg Met
                485                 490                 495

Asp Arg Gly Leu Pro Val Arg Ile Lys Glu Arg Lys Gly Cys
            500                 505                 510
```

<210> SEQ ID NO 13
<211> LENGTH: 1479
<212> TYPE: DNA
<213> ORGANISM: Veratrum californicum

<400> SEQUENCE: 13

```
atgggatcca ctgaggcgcc tgtatcaact cccaacccccg gcgtacagac agttgcggcg    60
aacgggtcat catgcttggc agggaccaag tccgttgaag cgaaagggtt taaggggcat   120
gacatgctgg caccttttcac ccctggatgg aagagcacct ccttggagcc tgttgtcatt   180
gagaagtcgg agggttgtta tgtttacgac aatcatggaa cgaaatatct tgatactatt   240
gctgggttgt ggtgcacgtc tttaggagga aatgagcctc gacttataga agctgcaact   300
gcacagttaa ataaattgcc atttaccac aacttctgca atcgtgtcac catacccttct   360
ttggatctag ccaaagaact tcttgatatg ttcactgcca agaaaatggg aaaggtgttc   420
ttcactaata gtggttctga ggccaatgac actcaggtga gctggttcg atattattttc   480
aatgcactgg gaaagccaaa taagaagaaa tttatagctc aaacgaaatc gttccatgga   540
actacagtag catctgctag tctctcgggc cttatgcatc tacattataa gttcgatctg   600
ccaattccaa atgtattgca ctcagattgt ccacactatt ggcgttacca tctaccaggt   660
gagtcggaag aggagttctc gtcaagatta gctgataatt tggagaaact tattctaaaa   720
gaagaaccag atacggttgc tgctttcatt gctgaacctg tcatgggcgc atcgggtgtt   780
ttccttcccc ccgagaccta ctttgagaag attcaagctg tcctaaagaa atacgatatt   840
ctcttcattg cggatgaggt cgtcactgca ttcgcaaggt tagggacaat gtttggatgt   900
gacaaataca acattcagcc ggacctcgtc tccttagcaa aagctctttc atctgcctac   960
attcccatcg gcgcagttat cgttagccaa gaaatttctg aagttataaa tcgtcaaagc  1020
acccaaattg gtacatttgc tcacgggtgt acgttttcgg ggcatccagt ggcctgcgct  1080
gttgctttgg agacacttaa gatttataag gagaggaata ttgttgagcg cgtccaggct  1140
atatcaacaa ggtttcaaga tggcatcaaa gccttctctg atagcccat tattggggag  1200
attcgtggaa ccgggttgat catcggggtc gactttacta agaacaagtc tccgaatgat  1260
gtcttcccctt acaagtgggg ggtcggagga atatttgtat cagaatgcgc aaaacgcggt  1320
atgatagttc atgagcctat cggagattgc acgacgttgt cacctgcact gataatatct  1380
gaagaagaga ttgaacaaat aatacaaatc tttggagaag ccctgaagag tacagagaag  1440
caagtggagc agatccagtc tcagaatacc gcaacttaa                         1479
```

<210> SEQ ID NO 14
<211> LENGTH: 492
<212> TYPE: PRT
<213> ORGANISM: Veratrum californicum

<400> SEQUENCE: 14

```
Met Gly Ser Thr Glu Ala Pro Val Ser Thr Pro Asn Pro Gly Val Gln
1               5                   10                  15

Thr Val Ala Ala Asn Gly Ser Ser Cys Leu Ala Gly Thr Lys Ser Val
            20                  25                  30

Glu Ala Lys Gly Phe Lys Gly His Asp Met Leu Ala Pro Phe Thr Pro
```

```
                35                  40                  45
Gly Trp Lys Ser Thr Ser Leu Glu Pro Val Ile Glu Lys Ser Glu
 50                  55                  60

Gly Cys Tyr Val Tyr Asp Asn His Gly Thr Lys Tyr Leu Asp Thr Ile
 65                  70                  75                  80

Ala Gly Leu Trp Cys Thr Ser Leu Gly Gly Asn Glu Pro Arg Leu Ile
                 85                  90                  95

Glu Ala Ala Thr Ala Gln Leu Asn Lys Leu Pro Phe Tyr His Asn Phe
                100                 105                 110

Cys Asn Arg Val Thr Ile Pro Ser Leu Asp Leu Ala Lys Glu Leu Leu
                115                 120                 125

Asp Met Phe Thr Ala Lys Lys Met Gly Lys Val Phe Phe Thr Asn Ser
    130                 135                 140

Gly Ser Glu Ala Asn Asp Thr Gln Val Lys Leu Val Arg Tyr Tyr Phe
145                 150                 155                 160

Asn Ala Leu Gly Lys Pro Asn Lys Lys Lys Phe Ile Ala Gln Thr Lys
                165                 170                 175

Ser Phe His Gly Thr Thr Val Ala Ser Ala Ser Leu Ser Gly Leu Met
                180                 185                 190

His Leu His Tyr Lys Phe Asp Leu Pro Ile Pro Asn Val Leu His Ser
    195                 200                 205

Asp Cys Pro His Tyr Trp Arg Tyr His Leu Pro Gly Glu Ser Glu Glu
    210                 215                 220

Glu Phe Ser Ser Arg Leu Ala Asp Asn Leu Glu Lys Leu Ile Leu Lys
225                 230                 235                 240

Glu Glu Pro Asp Thr Val Ala Ala Phe Ile Ala Glu Pro Val Met Gly
                245                 250                 255

Ala Ser Gly Val Phe Leu Pro Pro Glu Thr Tyr Phe Glu Lys Ile Gln
                260                 265                 270

Ala Val Leu Lys Lys Tyr Asp Ile Leu Phe Ile Ala Asp Glu Val Val
    275                 280                 285

Thr Ala Phe Ala Arg Leu Gly Thr Met Phe Gly Cys Asp Lys Tyr Asn
290                 295                 300

Ile Gln Pro Asp Leu Val Ser Leu Ala Lys Ala Leu Ser Ser Ala Tyr
305                 310                 315                 320

Ile Pro Ile Gly Ala Val Ile Val Ser Gln Glu Ile Ser Glu Val Ile
                325                 330                 335

Asn Arg Gln Ser Thr Gln Ile Gly Thr Phe Ala His Gly Cys Thr Phe
                340                 345                 350

Ser Gly His Pro Val Ala Cys Ala Val Ala Leu Glu Thr Leu Lys Ile
    355                 360                 365

Tyr Lys Glu Arg Asn Ile Val Glu Arg Val Gln Ala Ile Ser Thr Arg
    370                 375                 380

Phe Gln Asp Gly Ile Lys Ala Phe Ser Asp Ser Pro Ile Ile Gly Glu
385                 390                 395                 400

Ile Arg Gly Thr Gly Leu Ile Ile Gly Val Asp Phe Thr Lys Asn Lys
                405                 410                 415

Ser Pro Asn Asp Val Phe Pro Tyr Lys Trp Gly Val Gly Gly Ile Phe
                420                 425                 430

Val Ser Glu Cys Ala Lys Arg Gly Met Ile Val His Glu Pro Ile Gly
    435                 440                 445

Asp Cys Thr Thr Leu Ser Pro Ala Leu Ile Ile Ser Glu Glu Glu Ile
    450                 455                 460
```

Glu Gln Ile Ile Gln Ile Phe Gly Glu Ala Leu Lys Ser Thr Glu Lys
465                 470                 475                 480

Gln Val Glu Gln Ile Gln Ser Gln Asn Thr Ala Thr
                485                 490

<210> SEQ ID NO 15
<211> LENGTH: 1479
<212> TYPE: DNA
<213> ORGANISM: Veratrum californicum

<400> SEQUENCE: 15

| | | | | | |
|---|---|---|---|---|---|
| atgggatcca |

```
Glu Ala Lys Gly Phe Lys Gly His Asp Met Leu Ala Pro Phe Thr Pro
             35                  40                  45
Gly Trp Lys Ser Thr Ser Leu Glu Pro Val Val Ile Glu Lys Ser Glu
 50                  55                  60
Gly Cys Tyr Val Tyr Asp Asn His Gly Thr Lys Tyr Leu Asp Thr Ile
 65                  70                  75                  80
Ala Gly Leu Trp Cys Thr Ser Leu Gly Gly Asn Glu Pro Arg Leu Ile
                 85                  90                  95
Glu Ala Ala Thr Ala Gln Leu Asn Lys Leu Pro Phe Tyr His Asn Phe
                100                 105                 110
Cys Asn Arg Val Thr Ile Pro Ser Leu Asp Leu Ala Lys Glu Leu Leu
            115                 120                 125
Asp Met Phe Thr Ala Lys Lys Met Gly Lys Val Phe Phe Thr Asn Ser
        130                 135                 140
Gly Ser Glu Ala Asn Asp Thr Gln Val Lys Leu Val Arg Tyr Tyr Phe
145                 150                 155                 160
Asn Ala Leu Gly Lys Pro Asn Lys Lys Phe Ile Ala Gln Thr Lys
                165                 170                 175
Ser Phe His Gly Thr Thr Val Ala Ser Ala Ser Leu Ser Gly Leu Met
            180                 185                 190
His Leu His Tyr Lys Phe Asp Leu Pro Ile Pro Asn Val Leu His Ser
        195                 200                 205
Asp Cys Pro His Tyr Trp Arg Tyr His Leu Pro Gly Glu Ser Glu Glu
        210                 215                 220
Glu Phe Ser Ser Arg Leu Ala Asp Asn Leu Glu Lys Leu Ile Leu Lys
225                 230                 235                 240
Glu Glu Pro Asp Thr Val Ala Ala Phe Ile Ala Glu Pro Val Met Gly
                245                 250                 255
Ala Ser Gly Val Phe Leu Pro Pro Glu Thr Tyr Phe Glu Lys Ile Gln
                260                 265                 270
Ala Val Leu Lys Lys Tyr Asp Ile Leu Phe Ile Ala Asp Glu Val Val
            275                 280                 285
Thr Ala Phe Ala Arg Leu Gly Thr Met Phe Gly Cys Asp Lys Tyr Asn
        290                 295                 300
Ile Gln Pro Asp Leu Val Ser Leu Ala Lys Ala Leu Ser Ser Ala Tyr
305                 310                 315                 320
Ile Pro Ile Gly Ala Val Ile Val Ser Gln Glu Ile Ser Glu Val Ile
                325                 330                 335
Asn Arg Gln Ser Thr Gln Ile Gly Thr Phe Ala His Gly Cys Thr Phe
            340                 345                 350
Ser Gly His Pro Val Ala Cys Ala Val Ala Leu Glu Thr Leu Lys Ile
        355                 360                 365
Tyr Lys Glu Arg Asn Ile Val Glu Arg Val Gln Ala Ile Ser Lys Arg
        370                 375                 380
Phe Gln Asp Gly Ile Lys Ala Phe Ser Asp Ser Pro Ile Ile Gly Glu
385                 390                 395                 400
Ile Arg Gly Thr Gly Leu Ile Ile Gly Val Asp Phe Thr Lys Asn Lys
                405                 410                 415
Ser Pro Asn Asp Val Phe Pro Tyr Lys Trp Gly Val Gly Gly Ile Phe
            420                 425                 430
Val Ser Glu Cys Ala Lys Arg Gly Met Ile Val His Glu Pro Ile Gly
        435                 440                 445
Asp Cys Thr Thr Leu Ser Pro Ala Leu Ile Ile Ser Glu Glu Glu Ile
```

Glu Gln Ile Ile Gln Ile Phe Gly Glu Ala Leu Lys Ser Thr Glu Lys
465                 470                 475                 480

Gln Val Glu Gln Leu Gln Ser Gln Asn Thr Ala Thr
            485                 490

<210> SEQ ID NO 17
<211> LENGTH: 1479
<212> TYPE: DNA
<213> ORGANISM: Veratrum californicum

<400> SEQUENCE: 17

| | |
|---|---|
| atgggatcca ctgaggcgcc tgtatcaact cccaaccccg gcgtacagac agttgcggcg | 60 |
| aacgggtcat catgcttggc agggaccaag tccgttgaag tgaaagggtt taaggggcat | 120 |
| gacatgctgg caccttttcac ccctggatgg aagagcacct ccttggagcc tgttgtcatt | 180 |
| gagaagtcgg agggttgtta tgtttacgac aatcatggaa cgaaatatct tgatactatt | 240 |
| gctgggttgt ggtgcacgtc tttaggagga atgagcctc gacttataga agctgcaact | 300 |
| gcacagttaa ataaattgcc attttaccac aacttctgca atcgtgtcac catacccttct | 360 |
| ttggatctag ccaaagaact tcttgatatg ttcactgcca agaaaatggg aaaggtgttc | 420 |
| ttcactaata gtggttctga ggccaatgac actcaggtga agctggttcg atattatttc | 480 |
| aatgcactgg gaaagccaaa taagaagaaa tttatagctc aaacgaaatc gttccatgga | 540 |
| actacagtag catctgctag tctctcgggc cttatgcatc tacattataa gttcgatctg | 600 |
| ccaattccaa atgtattgca ctcagattgt ccacactatt ggcgttacca tctaccaggt | 660 |
| gagtcggaag aggagttctc gtcaagatta gctgataatt tggagaaact tattctaaaa | 720 |
| gaagaaccag atacggttgc tgctttcatt gctgaacctg tcatgggcgc atcgggtgtt | 780 |
| ttccttcccc ccgagaccta ctttgagaag attcaagctg tcctaaagaa atacgatatt | 840 |
| ctcttcattg cggatgaggt cgtcactgca ttcgcaaggt tagggacaat gtttggatgt | 900 |
| gacaaataca acattcagcc ggacctcgtc tccttagcaa aagctctttc atctgcctac | 960 |
| attcccatcg gcgcagttat cgttagccaa gaaatttctg aagttataaa tcgtcaaagc | 1020 |
| acccaaattg gtacatttgc tcacgggtgt acgttttcgg ggcatccagt ggcctgcgct | 1080 |
| gttgctttgg agacacttaa gatttataag gagaggaata ttgttgagcg cgtccaggct | 1140 |
| atatcaacaa ggtttcaaga tggcatcaaa gccttctctg atagccccat tattggggag | 1200 |
| attcgtggaa ccgggttgat catcggggtc gactttacta gaacaagtc tccgaatgat | 1260 |
| gtcttccctt acaagtgggg ggtcggagga atatttgtat cagaatgcgc aaaacgcggt | 1320 |
| atgatagttc atgagcctat cggagattgc acgacgttgt cacctgcact gataatatct | 1380 |
| gaagaagaga ttgaacaaat aatacaaatc tttggagaag ccctgaagag tacagagaag | 1440 |
| caagtggagc agatccagtc tcagaatacc gcaacttaa | 1479 |

<210> SEQ ID NO 18
<211> LENGTH: 492
<212> TYPE: PRT
<213> ORGANISM: Veratrum californicum

<400> SEQUENCE: 18

Met Gly Ser Thr Glu Ala Pro Val Ser Thr Pro Asn Pro Gly Val Gln
1               5                   10                  15

Thr Val Ala Ala Asn Gly Ser Ser Cys Leu Ala Gly Thr Lys Ser Val
            20                  25                  30

```
Glu Val Lys Gly Phe Lys Gly His Asp Met Leu Ala Pro Phe Thr Pro
         35                  40                  45

Gly Trp Lys Ser Thr Ser Leu Glu Pro Val Val Ile Glu Lys Ser Glu
     50                  55                  60

Gly Cys Tyr Val Tyr Asp Asn His Gly Thr Lys Tyr Leu Asp Thr Ile
 65                  70                  75                  80

Ala Gly Leu Trp Cys Thr Ser Leu Gly Gly Asn Glu Pro Arg Leu Ile
                 85                  90                  95

Glu Ala Ala Thr Ala Gln Leu Asn Lys Leu Pro Phe Tyr His Asn Phe
                100                 105                 110

Cys Asn Arg Val Thr Ile Pro Ser Leu Asp Leu Ala Lys Glu Leu Leu
            115                 120                 125

Asp Met Phe Thr Ala Lys Lys Met Gly Lys Val Phe Phe Thr Asn Ser
        130                 135                 140

Gly Ser Glu Ala Asn Asp Thr Gln Val Lys Leu Val Arg Tyr Tyr Phe
145                 150                 155                 160

Asn Ala Leu Gly Lys Pro Asn Lys Lys Phe Ile Ala Gln Thr Lys
                165                 170                 175

Ser Phe His Gly Thr Thr Val Ala Ser Ala Ser Leu Ser Gly Leu Met
                180                 185                 190

His Leu His Tyr Lys Phe Asp Leu Pro Ile Pro Asn Val Leu His Ser
            195                 200                 205

Asp Cys Pro His Tyr Trp Arg Tyr His Leu Pro Gly Glu Ser Glu Glu
        210                 215                 220

Glu Phe Ser Ser Arg Leu Ala Asp Asn Leu Glu Lys Leu Ile Leu Lys
225                 230                 235                 240

Glu Glu Pro Asp Thr Val Ala Ala Phe Ile Ala Glu Pro Val Met Gly
                245                 250                 255

Ala Ser Gly Val Phe Leu Pro Pro Glu Thr Tyr Phe Glu Lys Ile Gln
                260                 265                 270

Ala Val Leu Lys Lys Tyr Asp Ile Leu Phe Ile Ala Asp Glu Val Val
            275                 280                 285

Thr Ala Phe Ala Arg Leu Gly Thr Met Phe Gly Cys Asp Lys Tyr Asn
        290                 295                 300

Ile Gln Pro Asp Leu Val Ser Leu Ala Lys Ala Leu Ser Ser Ala Tyr
305                 310                 315                 320

Ile Pro Ile Gly Ala Val Ile Ser Gln Glu Ile Ser Glu Val Ile
                325                 330                 335

Asn Arg Gln Ser Thr Gln Ile Gly Thr Phe Ala His Gly Cys Thr Phe
                340                 345                 350

Ser Gly His Pro Val Ala Cys Ala Val Ala Leu Glu Thr Leu Lys Ile
            355                 360                 365

Tyr Lys Glu Arg Asn Ile Val Glu Arg Val Gln Ala Ile Ser Thr Arg
        370                 375                 380

Phe Gln Asp Gly Ile Lys Ala Phe Ser Asp Ser Pro Ile Ile Gly Glu
385                 390                 395                 400

Ile Arg Gly Thr Gly Leu Ile Ile Gly Val Asp Phe Thr Lys Asn Lys
                405                 410                 415

Ser Pro Asn Asp Val Phe Pro Tyr Lys Trp Gly Val Gly Gly Ile Phe
                420                 425                 430

Val Ser Glu Cys Ala Lys Arg Gly Met Ile Val His Glu Pro Ile Gly
            435                 440                 445
```

Asp Cys Thr Thr Leu Ser Pro Ala Leu Ile Ile Ser Glu Glu Glu Ile
            450                 455                 460

Glu Gln Ile Ile Gln Ile Phe Gly Glu Ala Leu Lys Ser Thr Glu Lys
465                 470                 475                 480

Gln Val Glu Gln Ile Gln Ser Gln Asn Thr Ala Thr
            485                 490

<210> SEQ ID NO 19
<211> LENGTH: 1464
<212> TYPE: DNA
<213> ORGANISM: Veratrum californicum

<400> SEQUENCE: 19

| | |
|---|---:|
| atggctccag tagttgttct cttctttctg ttccctacac tactagtgtt ggtggttgca | 60 |
| gcatttgggc agctagcagg caaggatgat gggtggagga agaggggct gaggctccca | 120 |
| ccgggcacca tgggttggcc gctcgtcgga gaaaccctgt ccttcggaaa gatccacccc | 180 |
| agcacttcca tcggagacta cctcgaggag cacatccaca agttcggaaa gattttcaag | 240 |
| gcgaacttgt tcgcatctca ggcggtggtt tcggtggacg cggagctgaa ccggttcgtg | 300 |
| atgctgaacg acgggcggct gttcgagccg tgcaccccga aggggtgct ggacatcctg | 360 |
| gggcacgcga cgccgatggc gttgtcgggt gatctgcacc gctacatcaa gtctttgtcc | 420 |
| gttgatttca tggggatcgg aaggatgaag agctacttcc tccccgacgc cgagcggtac | 480 |
| atcacggaga cgctcgcctc gtgggaggag gcacgccat ccaagccaa ggaggaggca | 540 |
| tccaagatga tgttcaattt gatggtgaag aacgttctca gcatgaaagc tggtgtcccc | 600 |
| gagactgagc ggctccgcaa gctttacatg tctttcatga agggggtcat tgcattacct | 660 |
| ctcaatttcc ctggatctgc ctacaaaaaa gccgtagagg caagaaaagt gattctggga | 720 |
| gtgataaacg agttgatgaa ggaaaggatc caaaagagaa gagacggaac ggacgatatc | 780 |
| ggcgaagctg acctattagg gttcgtactc gagcagtcca acctcgacgc cgagcagttc | 840 |
| ggcgatctct tgtttgggttt gttgttcggc ggccacgaga cctcagctac ggccatcacc | 900 |
| ctgctcatct acttccttca cgactgcccct ttggccgtta acaactccg ggaagagcac | 960 |
| atggagatcg tgaggatgaa aaggcaaaga ggagagcctg ctgcactaac atgggaggac | 1020 |
| tacaaactga tggagtttag ccaatgtgtg gtgcgagaga ctcttcgatt gggtaacgtg | 1080 |
| gtcaagttta ttgtgcgcaa ggcgagcact gatattaaat tcaaagggta tgatattccc | 1140 |
| aaagggtgga ccgtgttgcc gatcttaaca gccgcccatg ttgatccctc tgtttatgag | 1200 |
| aacgttcaca aattcgatcc atggagatgg cagactggtt ctacaagcaa agccttgaac | 1260 |
| gacaactaca tgcctttcgg tttgggattg cgcaactgcg cgggcctgca actcgccaag | 1320 |
| ttggagattg ttgtgtttct tcaccatctc gtactcaact ttgactggga gctggcagag | 1380 |
| cccgacaatc ccatagcgtc ccctttcccc gagttcccca ggggcctacc catcaaggtt | 1440 |
| cgccggcttt cgctcctcca ataa | 1464 |

<210> SEQ ID NO 20
<211> LENGTH: 487
<212> TYPE: PRT
<213> ORGANISM: Veratrum californicum

<400> SEQUENCE: 20

Met Ala Pro Val Val Val Leu Phe Phe Leu Phe Pro Thr Leu Leu Val
1               5                   10                  15

Leu Val Val Ala Ala Phe Gly Gln Leu Ala Gly Lys Asp Asp Gly Trp

```
              20                  25                  30
Arg Lys Arg Gly Leu Arg Leu Pro Pro Gly Thr Met Gly Trp Pro Leu
             35                  40                  45
Val Gly Glu Thr Leu Ser Phe Gly Lys Ile His Pro Ser Thr Ser Ile
         50                  55                  60
Gly Asp Tyr Leu Glu Glu His Ile His Lys Phe Gly Lys Ile Phe Lys
 65                  70                  75                  80
Ala Asn Leu Phe Ala Ser Gln Ala Val Val Ser Val Asp Ala Glu Leu
                 85                  90                  95
Asn Arg Phe Val Met Leu Asn Asp Gly Arg Leu Phe Glu Pro Cys Thr
                100                 105                 110
Pro Lys Gly Val Leu Asp Ile Leu Gly His Ala Thr Pro Met Ala Leu
            115                 120                 125
Ser Gly Asp Leu His Arg Tyr Ile Lys Ser Leu Ser Val Asp Phe Met
        130                 135                 140
Gly Ile Gly Arg Met Lys Ser Tyr Phe Leu Pro Asp Ala Glu Arg Tyr
145                 150                 155                 160
Ile Thr Glu Thr Leu Ala Ser Trp Glu Glu Gly Thr Pro Phe Gln Ala
                165                 170                 175
Lys Glu Glu Ala Ser Lys Met Met Phe Asn Leu Met Val Lys Asn Val
                180                 185                 190
Leu Ser Met Lys Ala Gly Val Pro Glu Thr Glu Arg Leu Arg Lys Leu
            195                 200                 205
Tyr Met Ser Phe Met Lys Gly Val Ile Ala Leu Pro Leu Asn Phe Pro
        210                 215                 220
Gly Ser Ala Tyr Lys Lys Ala Val Glu Ala Arg Lys Val Ile Leu Gly
225                 230                 235                 240
Val Ile Asn Glu Leu Met Lys Glu Arg Ile Gln Lys Arg Arg Asp Gly
                245                 250                 255
Thr Asp Asp Ile Gly Glu Ala Asp Leu Leu Gly Phe Val Leu Glu Gln
            260                 265                 270
Ser Asn Leu Asp Ala Glu Gln Phe Gly Asp Leu Leu Leu Gly Leu Leu
        275                 280                 285
Phe Gly Gly His Glu Thr Ser Ala Thr Ala Ile Thr Leu Leu Ile Tyr
    290                 295                 300
Phe Leu His Asp Cys Pro Leu Ala Val Lys Gln Leu Arg Glu Glu His
305                 310                 315                 320
Met Glu Ile Val Arg Met Lys Arg Gln Arg Gly Glu Pro Ala Ala Leu
                325                 330                 335
Thr Trp Glu Asp Tyr Lys Leu Met Glu Phe Ser Gln Cys Val Val Arg
            340                 345                 350
Glu Thr Leu Arg Leu Gly Asn Val Val Lys Phe Ile Val Arg Lys Ala
        355                 360                 365
Ser Thr Asp Ile Lys Phe Lys Gly Tyr Asp Ile Pro Lys Gly Trp Thr
    370                 375                 380
Val Leu Pro Ile Leu Thr Ala Ala His Val Asp Pro Ser Val Tyr Glu
385                 390                 395                 400
Asn Val His Lys Phe Asp Pro Trp Arg Trp Gln Thr Gly Ser Thr Ser
                405                 410                 415
Lys Ala Leu Asn Asp Asn Tyr Met Pro Phe Gly Leu Gly Leu Arg Asn
            420                 425                 430
Cys Ala Gly Leu Gln Leu Ala Lys Leu Glu Ile Val Val Phe Leu His
        435                 440                 445
```

His Leu Val Leu Asn Phe Asp Trp Glu Leu Ala Glu Pro Asp Asn Pro
    450                 455                 460

Ile Ala Ser Pro Phe Pro Glu Phe Pro Arg Gly Leu Pro Ile Lys Val
465                 470                 475                 480

Arg Arg Leu Ser Leu Leu Gln
            485

<210> SEQ ID NO 21
<211> LENGTH: 1470
<212> TYPE: DNA
<213> ORGANISM: Veratrum californicum

<400> SEQUENCE: 21

| | | | | | |
|---|---|---|---|---|---|
| atggctccag | tagttgttct | cttctttctg | ttccctacac | tactagtgtt | ggtggttgca | 60 |
| gcatttgggc | agctagcagg | caaggatgat | gggtggagga | agaggggggct | gaggctccca | 120 |
| ccgggcacca | tgggttggcc | gctcgtcgga | gaaaccctgt | ccttcggaaa | gatccacccc | 180 |
| agcacttcca | tcggagacta | cctcgaggag | cacatccaca | agttcggaaa | gattttcaag | 240 |
| gcgaacttgt | tcgcatctca | ggcggtggtt | tcggtggacg | cggagctgaa | ccggttcgtg | 300 |
| atgctgaacg | acgggcggct | gttcgagccg | tgcaccccga | agggggtgct | ggacatcctg | 360 |
| gggcacgcga | cgccgatggc | gttgtcgggt | gatctgcacc | gctacatcaa | gtctttgtcc | 420 |
| gttgatttca | tggggatcgg | aaggatgaag | agctacttcc | tccccgacgc | cgagcggtac | 480 |
| atcacggaga | cgctcgcctc | gtgggaggag | ggcacgccat | tccaagccaa | ggaggaggca | 540 |
| tccaagatga | tgttcaattt | gatggtgaag | aacgttctca | gcatgaaagc | tggtgtcccc | 600 |
| gagactgagc | ggctccgcaa | gctttacatg | tctttcatga | agggggtcat | tgcattacct | 660 |
| ctcaatttcc | ctggatctgc | ctacaaaaaa | gccgtagagg | caagaaaggt | gattctagga | 720 |
| gtgattaacg | agttgatgaa | ggaaaggatc | caaaacagga | gagacggaac | agacgatatc | 780 |
| ggcgaagctg | acctactagg | gttcgtactc | gagcagtcca | acctcgacgc | cgagcagttc | 840 |
| ggcgatctct | tgtttgggttt | gttgttcggc | ggccacgaga | cctcagccac | ggccattacc | 900 |
| ctgctcatct | acttccttca | cgactgccct | tggccgttc | aacaactccg | ggaagagcac | 960 |
| atggagattg | tgaggatgaa | aaggcaaaga | ggagagactg | ctgcactaac | atgggaggac | 1020 |
| tataaaactga | tggagttcag | ccaatgtgtg | gtgcgagaga | ctcttcgatt | gggtaacgtg | 1080 |
| gtcaagttta | ttgtgcgcaa | ggcgagcact | gatattaaat | caaagggta | tgatattccg | 1140 |
| aaaggttgga | cagtgttgcc | gatcttgaca | gccgcccatg | ttgatcccac | tgcttacgag | 1200 |
| aacgttcaca | aattcgatcc | atggagatgg | cagacgcaga | ccggttctac | aagcaaagcc | 1260 |
| ttgaacgaca | actacatgcc | ttttggttg | ggattgcgca | attgcgcggg | cctacaactc | 1320 |
| gccaagttgg | agattgttgt | gtttcttcac | catctcgtgc | tcaacttcga | ctgggaactc | 1380 |
| gcagagcccg | acagtcccgt | agcgtcccct | ttccccgagt | tccccagggg | cctacccatc | 1440 |
| aaggttcgcc | ggctttcgct | cctccaataa | | | | 1470 |

<210> SEQ ID NO 22
<211> LENGTH: 489
<212> TYPE: PRT
<213> ORGANISM: Veratrum californicum

<400> SEQUENCE: 22

Met Ala Pro Val Val Val Leu Phe Phe Leu Phe Pro Thr Leu Leu Val
1               5                   10                  15

```
Leu Val Val Ala Ala Phe Gly Gln Leu Ala Gly Lys Asp Asp Gly Trp
                20                  25                  30

Arg Lys Arg Gly Leu Arg Leu Pro Pro Gly Thr Met Gly Trp Pro Leu
            35                  40                  45

Val Gly Glu Thr Leu Ser Phe Gly Lys Ile His Pro Ser Thr Ser Ile
        50                  55                  60

Gly Asp Tyr Leu Glu Glu His Ile His Lys Phe Gly Lys Ile Phe Lys
 65                  70                  75                  80

Ala Asn Leu Phe Ala Ser Gln Ala Val Val Ser Val Asp Ala Glu Leu
                85                  90                  95

Asn Arg Phe Val Met Leu Asn Asp Gly Arg Leu Phe Glu Pro Cys Thr
            100                 105                 110

Pro Lys Gly Val Leu Asp Ile Leu Gly His Ala Thr Pro Met Ala Leu
        115                 120                 125

Ser Gly Asp Leu His Arg Tyr Ile Lys Ser Leu Ser Val Asp Phe Met
    130                 135                 140

Gly Ile Gly Arg Met Lys Ser Tyr Phe Leu Pro Asp Ala Glu Arg Tyr
145                 150                 155                 160

Ile Thr Glu Thr Leu Ala Ser Trp Glu Glu Gly Thr Pro Phe Gln Ala
                165                 170                 175

Lys Glu Glu Ala Ser Lys Met Met Phe Asn Leu Met Val Lys Asn Val
            180                 185                 190

Leu Ser Met Lys Ala Gly Val Pro Glu Thr Glu Arg Leu Arg Lys Leu
        195                 200                 205

Tyr Met Ser Phe Met Lys Gly Val Ile Ala Leu Pro Leu Asn Phe Pro
    210                 215                 220

Gly Ser Ala Tyr Lys Lys Ala Val Glu Ala Arg Lys Val Ile Leu Gly
225                 230                 235                 240

Val Ile Asn Glu Leu Met Lys Glu Arg Ile Gln Asn Arg Arg Asp Gly
                245                 250                 255

Thr Asp Asp Ile Gly Glu Ala Asp Leu Leu Gly Phe Val Leu Glu Gln
            260                 265                 270

Ser Asn Leu Asp Ala Glu Gln Phe Gly Asp Leu Leu Leu Gly Leu Leu
        275                 280                 285

Phe Gly Gly His Glu Thr Ser Ala Thr Ala Ile Thr Leu Leu Ile Tyr
    290                 295                 300

Phe Leu His Asp Cys Pro Leu Ala Val Gln Gln Leu Arg Glu Glu His
305                 310                 315                 320

Met Glu Ile Val Arg Met Lys Arg Gln Arg Gly Glu Thr Ala Ala Leu
                325                 330                 335

Thr Trp Glu Asp Tyr Lys Leu Met Glu Phe Ser Gln Cys Val Val Arg
            340                 345                 350

Glu Thr Leu Arg Leu Gly Asn Val Val Lys Phe Ile Val Arg Lys Ala
        355                 360                 365

Ser Thr Asp Ile Lys Phe Lys Gly Tyr Asp Ile Pro Lys Gly Trp Thr
    370                 375                 380

Val Leu Pro Ile Leu Thr Ala Ala His Val Asp Pro Thr Ala Tyr Glu
385                 390                 395                 400

Asn Val His Lys Phe Asp Pro Trp Arg Trp Gln Thr Gln Thr Gly Ser
                405                 410                 415

Thr Ser Lys Ala Leu Asn Asp Asn Tyr Met Pro Phe Gly Leu Gly Leu
            420                 425                 430

Arg Asn Cys Ala Gly Leu Gln Leu Ala Lys Leu Glu Ile Val Val Phe
```

435                 440                 445
Leu His His Leu Val Leu Asn Phe Asp Trp Glu Leu Ala Glu Pro Asp
        450                 455                 460

Ser Pro Val Ala Ser Pro Phe Pro Glu Phe Pro Arg Gly Leu Pro Ile
465                 470                 475                 480

Lys Val Arg Arg Leu Ser Leu Leu Gln
                485

<210> SEQ ID NO 23
<211> LENGTH: 1464
<212> TYPE: DNA
<213> ORGANISM: Veratrum californicum

<400> SEQUENCE: 23

| | | | | |
|---|---|---|---|---|
| atgactccat | tagttgttct | cttctttctg | ttccctacac | tactagtgtt ggtggttgca | 60 |
| gcatttgggc | agctagcagg | caaggatgat | gggtggagga | gaggggggct gaggctccca | 120 |
| ccgggcacca | tgggttggcc | gctcgtcgga | gaaaccctgt | ccttcggaaa gatccacccc | 180 |
| agcacttcca | tcggagacta | cctcgaggag | cacatccaca | gtacggaaa gattttcaag | 240 |
| gcgaacttgt | tcgcatctca | ggcggtggtt | tcggtggacg | cggagctgaa ccggttcgtg | 300 |
| atgctgaatg | acgggcggct | gttcgagccg | tgcaccccga | aggggtgct ggacatcctg | 360 |
| gggcacgcga | cgccgatggc | gttgtcgggt | gatctgcacc | gctacatcaa gtctctgtcc | 420 |
| gttgatttca | tggggatcgg | aaggatgaag | agctacttcc | tccccgacgc cgagcggtac | 480 |
| atcacggaga | cgctcgcctc | gtgggaggag | ggcacgccat | tccaagccaa ggaggaggca | 540 |
| tccaagatga | tgttcaattt | gatggtgaag | aacgttctca | gcatgaaagc tggtgtcccc | 600 |
| gagactgagc | ggctccgcaa | gctttacatg | tctttcatga | aggggtcat tgcattacct | 660 |
| ctcaatttcc | ctggatctgc | ctacaaaaaa | gccgtagagg | caagaaaagt gattctggga | 720 |
| gtgataaacg | agttgatgaa | ggaaaggatc | caaaagagaa | gagacggaac ggacgatatc | 780 |
| ggcgaagctg | acctattagg | gttcgtactc | gagcagtcca | acctcgacgc cgagcagttt | 840 |
| ggcgatctct | tgtttgggttt | gttgttcggc | ggccacgaga | cttcagctac ggccatcacc | 900 |
| ctgctcatct | acttccttca | cgactgccct | ttagccgtta | acaactccg ggaagagcac | 960 |
| atggagatcg | tgaggatgaa | aaggcaaaga | ggagagcctg | ctgcactaac atgggaggac | 1020 |
| tacaaactga | tggagtttag | ccaatgtgtg | gtgcgagaga | ctcttcgatt gggtaacgtg | 1080 |
| gtcaagttta | ttgtgcgcaa | ggcgagcact | gatattaaat | tcaaagggta tgatattccc | 1140 |
| aaagggtgga | ccgtgttgcc | gatcttaaca | gccgcccatg | ttgatccctc tgtttatgag | 1200 |
| aacgttcaca | aattcgatcc | atggagatgg | cagactggtt | ctacaagcaa agccttgaac | 1260 |
| gacaactaca | tgccttcgg | tttgggattg | cgcaactgcg | cgggcctgca actcgccaag | 1320 |
| ttggagattg | ttgtgttct | tcaccatctc | gtactcaact | tcgactggga gctggcagag | 1380 |
| cccgacaatc | ccatagcgtc | ccctttcccc | gagttcccca | ggggcctacc catcaaggtt | 1440 |
| cgccggcttt | cgctcctcca | ataa | | | 1464 |

<210> SEQ ID NO 24
<211> LENGTH: 487
<212> TYPE: PRT
<213> ORGANISM: Veratrum californicum

<400> SEQUENCE: 24

Met Thr Pro Leu Val Val Leu Phe Phe Leu Phe Pro Thr Leu Leu Val
1               5                   10                  15

-continued

Leu Val Val Ala Ala Phe Gly Gln Leu Ala Gly Lys Asp Asp Gly Trp
            20                  25                  30

Arg Lys Arg Gly Leu Arg Leu Pro Pro Gly Thr Met Gly Trp Pro Leu
        35                  40                  45

Val Gly Glu Thr Leu Ser Phe Gly Lys Ile His Pro Ser Thr Ser Ile
    50                  55                  60

Gly Asp Tyr Leu Glu Glu His Ile His Lys Tyr Gly Lys Ile Phe Lys
65                  70                  75                  80

Ala Asn Leu Phe Ala Ser Gln Ala Val Val Ser Val Asp Ala Glu Leu
                85                  90                  95

Asn Arg Phe Val Met Leu Asn Asp Gly Arg Leu Phe Glu Pro Cys Thr
            100                 105                 110

Pro Lys Gly Val Leu Asp Ile Leu Gly His Ala Thr Pro Met Ala Leu
        115                 120                 125

Ser Gly Asp Leu His Arg Tyr Ile Lys Ser Leu Ser Val Asp Phe Met
130                 135                 140

Gly Ile Gly Arg Met Lys Ser Tyr Phe Leu Pro Asp Ala Glu Arg Tyr
145                 150                 155                 160

Ile Thr Glu Thr Leu Ala Ser Trp Glu Glu Gly Thr Pro Phe Gln Ala
            165                 170                 175

Lys Glu Glu Ala Ser Lys Met Met Phe Asn Leu Met Val Lys Asn Val
        180                 185                 190

Leu Ser Met Lys Ala Gly Val Pro Glu Thr Glu Arg Leu Arg Lys Leu
    195                 200                 205

Tyr Met Ser Phe Met Lys Gly Val Ile Ala Leu Pro Leu Asn Phe Pro
    210                 215                 220

Gly Ser Ala Tyr Lys Lys Ala Val Glu Ala Arg Lys Val Ile Leu Gly
225                 230                 235                 240

Val Ile Asn Glu Leu Met Lys Glu Arg Ile Gln Lys Arg Arg Asp Gly
            245                 250                 255

Thr Asp Asp Ile Gly Glu Ala Asp Leu Leu Gly Phe Val Leu Glu Gln
        260                 265                 270

Ser Asn Leu Asp Ala Glu Gln Phe Gly Asp Leu Leu Gly Leu Leu
    275                 280                 285

Phe Gly Gly His Glu Thr Ser Ala Thr Ala Ile Thr Leu Leu Ile Tyr
    290                 295                 300

Phe Leu His Asp Cys Pro Leu Ala Val Lys Gln Leu Arg Glu Glu His
305                 310                 315                 320

Met Glu Ile Val Arg Met Lys Arg Gln Arg Gly Glu Pro Ala Ala Leu
            325                 330                 335

Thr Trp Glu Asp Tyr Lys Leu Met Glu Phe Ser Gln Cys Val Val Arg
        340                 345                 350

Glu Thr Leu Arg Leu Gly Asn Val Val Lys Phe Ile Val Arg Lys Ala
    355                 360                 365

Ser Thr Asp Ile Lys Phe Lys Gly Tyr Asp Ile Pro Lys Gly Trp Thr
    370                 375                 380

Val Leu Pro Ile Leu Thr Ala Ala His Val Asp Pro Ser Val Tyr Glu
385                 390                 395                 400

Asn Val His Lys Phe Asp Pro Trp Arg Trp Gln Thr Gly Ser Thr Ser
            405                 410                 415

Lys Ala Leu Asn Asp Asn Tyr Met Pro Phe Gly Leu Gly Leu Arg Asn
        420                 425                 430

```
Cys Ala Gly Leu Gln Leu Ala Lys Leu Glu Ile Val Val Phe Leu His
        435                 440                 445

His Leu Val Leu Asn Phe Asp Trp Glu Leu Ala Glu Pro Asp Asn Pro
    450                 455                 460

Ile Ala Ser Pro Phe Pro Glu Phe Pro Arg Gly Leu Pro Ile Lys Val
465             470                 475                 480

Arg Arg Leu Ser Leu Leu Gln
                485

<210> SEQ ID NO 25
<211> LENGTH: 1464
<212> TYPE: DNA
<213> ORGANISM: Veratrum californicum

<400> SEQUENCE: 25
atgactccac tagttgttct cttctttctg ttccctacac

```
1               5                   10                  15
Leu Val Val Ala Ala Phe Gly Gln Leu Ala Gly Lys Asp Asp Gly Trp
                20                  25                  30

Arg Lys Arg Gly Leu Arg Leu Pro Pro Gly Thr Met Gly Trp Pro Leu
                35                  40                  45

Val Gly Glu Thr Leu Ser Phe Gly Lys Ile His Pro Ser Thr Ser Ile
                50                  55                  60

Gly Asp Tyr Leu Glu Glu His Ile His Lys Phe Gly Lys Ile Phe Lys
65                  70                  75                  80

Ala Asn Leu Phe Ala Ser Gln Ala Val Val Ser Val Asp Ala Glu Leu
                85                  90                  95

Asn Arg Phe Val Met Leu Asn Asp Gly Arg Leu Phe Glu Pro Cys Thr
                100                 105                 110

Pro Lys Gly Val Leu Asp Ile Leu Gly His Ala Thr Pro Met Ala Leu
                115                 120                 125

Ser Gly Asp Leu His Arg Tyr Ile Lys Ser Leu Ser Val Asp Phe Met
    130                 135                 140

Gly Ile Gly Arg Met Lys Ser Tyr Phe Leu Pro Asp Ala Glu Arg Tyr
145                 150                 155                 160

Ile Thr Glu Thr Leu Ala Ser Trp Glu Glu Gly Thr Pro Phe Gln Ala
                165                 170                 175

Lys Glu Glu Ala Ser Lys Met Met Phe Asn Leu Met Val Lys Asn Val
                180                 185                 190

Leu Ser Met Lys Ala Gly Val Pro Glu Thr Glu Arg Leu Arg Lys Leu
        195                 200                 205

Tyr Met Ser Phe Met Lys Gly Val Ile Ala Leu Pro Leu Asn Phe Pro
    210                 215                 220

Gly Ser Ala Tyr Lys Lys Ala Val Glu Ala Arg Lys Val Ile Leu Gly
225                 230                 235                 240

Val Ile Asn Glu Leu Met Lys Glu Arg Ile Gln Lys Arg Arg Asp Gly
                245                 250                 255

Thr Asp Asp Ile Gly Glu Ala Asp Leu Leu Gly Phe Val Leu Glu Gln
            260                 265                 270

Ser Asn Leu Asp Ala Glu Gln Phe Gly Asp Leu Leu Leu Gly Leu Leu
        275                 280                 285

Phe Gly Gly His Glu Thr Ser Ala Thr Ala Ile Thr Leu Leu Ile Tyr
290                 295                 300

Phe Leu His Asp Cys Pro Leu Ala Val Lys Gln Leu Arg Glu Glu His
305                 310                 315                 320

Met Glu Ile Val Arg Met Lys Arg Gln Arg Gly Glu Pro Ala Ala Leu
                325                 330                 335

Thr Trp Glu Asp Tyr Lys Leu Met Glu Phe Ser Gln Cys Val Val Arg
            340                 345                 350

Glu Thr Leu Arg Leu Gly Asn Val Val Lys Phe Ile Val Arg Lys Ala
        355                 360                 365

Ser Thr Asp Ile Lys Phe Lys Gly Tyr Asp Ile Pro Lys Gly Trp Thr
    370                 375                 380

Val Leu Pro Ile Leu Thr Ala Ala His Val Asp Pro Ser Val Tyr Glu
385                 390                 395                 400

Asn Val His Lys Phe Asp Pro Trp Arg Trp Gln Thr Gly Ser Thr Ser
                405                 410                 415

Lys Ala Leu Asn Asp Asn Tyr Met Pro Phe Gly Leu Gly Leu Arg Asn
            420                 425                 430
```

```
Cys Ala Gly Leu Gln Leu Ala Lys Leu Glu Ile Val Val Phe Leu His
        435                 440                 445

His Leu Val Leu Asn Phe Asp Trp Glu Leu Ala Glu Pro Asp Asn Pro
    450                 455                 460

Ile Ala Ser Pro Phe Pro Glu Phe Pro Arg Gly Leu Pro Ile Lys Val
465                 470                 475                 480

Arg Arg Leu Ser Leu Leu Gln
                485

<210> SEQ ID NO 27
<211> LENGTH: 29
<212> TYPE: DNA
<213> ORGANISM: Artificial Sequence
<220> FEATURE:
<223> OTHER INFORMATION: PCR Primer 5' UTR outer for 2646

<400> SEQUENCE: 27
caagtcgtga ttgatggctt tagaaggca                                   29

<210> SEQ ID NO 28
<211> LENGTH: 29
<212> TYPE: DNA
<213> ORGANISM: Artificial Sequence
<220> FEATURE:
<223> OTHER INFORMATION: PCR Primer 5' UTR inner  for 2646

<400> SEQUENCE: 28
tggatctctg aagccatgaa tcgctagta                                   29

<210> SEQ ID NO 29
<211> LENGTH: 27
<212> TYPE: DNA
<213> ORGANISM: Artificial Sequence
<220> FEATURE:
<223> OTHER INFORMATION: PCR Primer 3' UTR outer for 2646

<400> SEQUENCE: 29
tcctataacc atttatttct cgtaacc                                     27

<210> SEQ ID NO 30
<211> LENGTH: 26
<212> TYPE: DNA
<213> ORGANISM: Artificial Sequence
<220> FEATURE:
<223> OTHER INFORMATION: PCR Primer 3' UTR inner for 2646

<400> SEQUENCE: 30
atgcagagag caatattaca acccaa                                      26

<210> SEQ ID NO 31
<211> LENGTH: 35
<212> TYPE: DNA
<213> ORGANISM: Artificial Sequence
<220> FEATURE:
<223> OTHER INFORMATION: PCR Primer 5' gene specific primer (GSP) used
      to amplify 2646

<400> SEQUENCE: 31
tgagcggccg catggcgatg gagctcttat tgttg                            35

<210> SEQ ID NO 32
<211> LENGTH: 32
<212> TYPE: DNA
<213> ORGANISM: Artificial Sequence
```

```
<220> FEATURE:
<223> OTHER INFORMATION: PCR Primer 3' used to amplify 2646

<400> SEQUENCE: 32
tgaggatcct tagtctccga gggggcgaac tt                              32

<210> SEQ ID NO 33
<211> LENGTH: 27
<212> TYPE: DNA
<213> ORGANISM: Artificial Sequence
<220> FEATURE:
<223> OTHER INFORMATION: PCR Primer 5' UTR for 13284

<400> SEQUENCE: 33
agaaagaaag agagagagat gactcca                                    27

<210> SEQ ID NO 34
<211> LENGTH: 31
<212> TYPE: DNA
<213> ORGANISM: Artificial Sequence
<220> FEATURE:
<223> OTHER INFORMATION: PCR Primer 3' UTR for 13284

<400> SEQUENCE: 34
tagagaaaga ctgcttgaat ttttcaggca a                               31

<210> SEQ ID NO 35
<211> LENGTH: 33
<212> TYPE: DNA
<213> ORGANISM: Artificial Sequence
<220> FEATURE:
<223> OTHER INFORMATION: PCR Primer 5' used to amplify 13284

<400> SEQUENCE: 35
gggctgcaga tgactccact agttgttctc ttc                             33

<210> SEQ ID NO 36
<211> LENGTH: 30
<212> TYPE: DNA
<213> ORGANISM: Artificial Sequence
<220> FEATURE:
<223> OTHER INFORMATION: PCR Primer 3' used to amplify 13284

<400> SEQUENCE: 36
gggtctagat tattggagga gcgaaagccg                                 30

<210> SEQ ID NO 37
<211> LENGTH: 35
<212> TYPE: DNA
<213> ORGANISM: Artificial Sequence
<220> FEATURE:
<223> OTHER INFORMATION: PCR Primer 5' used to amplify 12084

<400> SEQUENCE: 37
gggagatcta tgggatccac tgaggcgcct gtatc                           35

<210> SEQ ID NO 38
<211> LENGTH: 34
<212> TYPE: DNA
<213> ORGANISM: Artificial Sequence
<220> FEATURE:
<223> OTHER INFORMATION: PCR Primer 3' used to amplify 12084

<400> SEQUENCE: 38
ggggaattct taagttgcgg tattctgaga ctgg                            34
```

```
<210> SEQ ID NO 39
<211> LENGTH: 23
<212> TYPE: DNA
<213> ORGANISM: Artificial Sequence
<220> FEATURE:
<223> OTHER INFORMATION: PCR Primer 5' outer RACE for 12709

<400> SEQUENCE: 39
gcactggagc acgaggacac tga                                          23

<210> SEQ ID NO 40
<211> LENGTH: 26
<212> TYPE: DNA
<213> ORGANISM: Artificial Sequence
<220> FEATURE:
<223> OTHER INFORMATION: PCR Primer 5' inner RACE for 12709

<400> SEQUENCE: 40
ggacactgac atggactgaa ggagta                                       26

<210> SEQ ID NO 41
<211> LENGTH: 28
<212> TYPE: DNA
<213> ORGANISM: Artificial Sequence
<220> FEATURE:
<223> OTHER INFORMATION: PCR Primer Outer gene specific internal reverse
      for 12709 5' RACE

<400> SEQUENCE: 41
tggtccacca cgtgcggccg cgacgaga                                     28

<210> SEQ ID NO 42
<211> LENGTH: 27
<212> TYPE: DNA
<213> ORGANISM: Artificial Sequence
<220> FEATURE:
<223> OTHER INFORMATION: PCR Primer Inner Gene specific internal reverse
      for 12709 5' RACE

<400> SEQUENCE: 42
gaaccaggtg agcgccgagg gggtggt                                      27

<210> SEQ ID NO 43
<211> LENGTH: 29
<212> TYPE: DNA
<213> ORGANISM: Artificial Sequence
<220> FEATURE:
<223> OTHER INFORMATION: PCR Primer 5' used to amplify 12709

<400> SEQUENCE: 43
gggagatcta tggatctacc ctccgcctc                                    29

<210> SEQ ID NO 44
<211> LENGTH: 34
<212> TYPE: DNA
<213> ORGANISM: Artificial Sequence
<220> FEATURE:
<223> OTHER INFORMATION: PCR Primer 3' used to amplify 12709

<400> SEQUENCE: 44
ggggaattcc taacaccctc tcttcctctc cttg                              34

<210> SEQ ID NO 45
<211> LENGTH: 34
<212> TYPE: DNA
<213> ORGANISM: Artificial Sequence
```

```
<220> FEATURE:
<223> OTHER INFORMATION: PCR Primer 5' used to amplify Tomato GABAT

<400> SEQUENCE: 45
cacactgcag atggccaaga ctaatggatt tatg                                34

<210> SEQ ID NO 46
<211> LENGTH: 39
<212> TYPE: DNA
<213> ORGANISM: Artificial Sequence
<220> FEATURE:
<223> OTHER INFORMATION: PCR Primer 3' used to amplify Tomato GABAT

<400> SEQUENCE: 46
cacatctaga ttacttcttc tgagacttta attcttcca                           39

<210> SEQ ID NO 47
<211> LENGTH: 32
<212> TYPE: DNA
<213> ORGANISM: Artificial Sequence
<220> FEATURE:
<223> OTHER INFORMATION: PCR Primer 5' used to amplify VC674 GABAT

<400> SEQUENCE: 47
cacactgcag atgttctcaa ggcaagctac ag                                  32

<210> SEQ ID NO 48
<211> LENGTH: 36
<212> TYPE: DNA
<213> ORGANISM: Artificial Sequence
<220> FEATURE:
<223> OTHER INFORMATION: PCR Primer 3' used to amplify VC674 GABAT

<400> SEQUENCE: 48
cacatctaga ctacttctgc ttctgagact tgagct                              36

<210> SEQ ID NO 49
<211> LENGTH: 22
<212> TYPE: DNA
<213> ORGANISM: Artificial Sequence
<220> FEATURE:
<223> OTHER INFORMATION: RT PCR Primer 5' -- 3'

<400> SEQUENCE: 49
ccatcaagga tgtgcagttc aa                                             22

<210> SEQ ID NO 50
<211> LENGTH: 23
<212> TYPE: DNA
<213> ORGANISM: Artificial Sequence
<220> FEATURE:
<223> OTHER INFORMATION: RT PCR Primer 5' -- 3'

<400> SEQUENCE: 50
gccgctgaat gacatgattg acg                                            23

<210> SEQ ID NO 51
<211> LENGTH: 22
<212> TYPE: DNA
<213> ORGANISM: Artificial Sequence
<220> FEATURE:
<223> OTHER INFORMATION: RT PCR Primer 5' -- 3'

<400> SEQUENCE: 51
acggtgatgt acagcgcgtt cg                                             22
```

```
<210> SEQ ID NO 52
<211> LENGTH: 20
<212> TYPE: DNA
<213> ORGANISM: Artificial Sequence
<220> FEATURE:
<223> OTHER INFORMATION: RT PCR Primer 5' -- 3'

<400> SEQUENCE: 52
gatacgcgct cgccgactta                                                   20

<210> SEQ ID NO 53
<211> LENGTH: 25
<212> TYPE: DNA
<213> ORGANISM: Artificial Sequence
<220> FEATURE:
<223> OTHER INFORMATION: RT PCR Primer 5' -- 3'

<400> SEQUENCE: 53
gatgaaggaa aggatccaaa agaga                                             25

<210> SEQ ID NO 54
<211> LENGTH: 21
<212> TYPE: DNA
<213> ORGANISM: Artificial Sequence
<220> FEATURE:
<223> OTHER INFORMATION: RT PCR Primer 5' -- 3'

<400> SEQUENCE: 54
agggtgatgg ccgtagctga a                                                 21

<210> SEQ ID NO 55
<211> LENGTH: 23
<212> TYPE: DNA
<213> ORGANISM: Artificial Sequence
<220> FEATURE:
<223> OTHER INFORMATION: RT PCR Primer 5' -- 3'

<400> SEQUENCE: 55
acatttgctc acgggtgtac gtt                                               23

<210> SEQ ID NO 56
<211> LENGTH: 24
<212> TYPE: DNA
<213> ORGANISM: Artificial Sequence
<220> FEATURE:
<223> OTHER INFORMATION: RT PCR Primer 5' -- 3'

<400> SEQUENCE: 56
cttagtaaag tcgaccccga tgat                                              24

<210> SEQ ID NO 57
<211> LENGTH: 23
<212> TYPE: DNA
<213> ORGANISM: Artificial Sequence
<220> FEATURE:
<223> OTHER INFORMATION: RT PCR Primer 5' -- 3'

<400> SEQUENCE: 57
gagtttcctg atgttagact caa                                               23

<210> SEQ ID NO 58
<211> LENGTH: 22
<212> TYPE: DNA
<213> ORGANISM: Artificial Sequence
<220> FEATURE:
<223> OTHER INFORMATION: RT PCR Primer 5' -- 3'
```

```
<400> SEQUENCE: 58
acacctaact gacttgccaa ca                                                      22
```

CONSTRUCTS AND METHODS FOR BIOSYNTHESIS OF CYCLOPAMINE

CROSS REFERENCE TO RELATED APPLICATIONS

The present application claims the benefit of U.S. Provisional Application No. 62/018,556, filed Jun. 28, 2014, entitled "Constructs and Methods for Biosynthesis of Cyclopamine," and U.S. Provisional Application No. 62/152,489 filed Apr. 24, 2015 entitled "Constructs and Methods for Biosynthesis of Cyclopamine," and is a continuation of International Application No. WO 2015/200831, filed Jun. 26, 2015, entitled "Constructs and Methods for Biosynthesis of Cyclopamine," all of which are herein incorporated by reference.

STATEMENT REGARDING FEDERALLY SPONSORED RESEARCH

This invention was made with government support under Grant No. DA025197 awarded by the National Institutes of Health. The government has certain rights in the invention.

INCORPORATION BY REFERENCE OF THE SEQUENCE LISTING

The accompanying "Sequence Listing" forms a part of this application and the sequences disclosed therein are herein incorporated by reference.

BACKGROUND

Cyclopamine (11-deoxojervine):

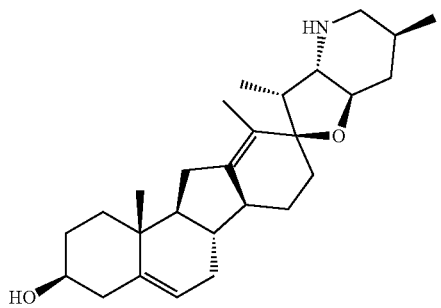 [SMILES: CC1=C2C[C@H]3[C@@H](CC=C4C[C@@H](O)CC[C@@]43C)[C@@H]2CC[C@]12O[C@@H]1C[C@H](C)CN[C@H]1[C@H]2C]

is a naturally occurring alkaloid isolated from the corn lily (*Veratrum californicum*). It belongs to the group of steroidal jerveratrum alkaloids, and causes usually fatal birth defects such as preventing the fetal brain from dividing into two lobes (holoprosencephaly) and inducing cyclopian teratogenic effects in sheep, causing the development of a single eye (cyclopia). It does so by inhibiting the hedgehog signaling pathway (Hh), and is therefore useful in studying the role of Hh in normal development.

Inappropriate activation of the Hh can also trigger cancer in adult humans, leading to basal cell carcinoma, medulloblastoma, rhabdomyosarcoma, and prostate, pancreatic, and breast cancers. Cyclopamine appears to act as a primary inhibitor of the Hh in cells, and controlling the pathway using cyclopamine could provide a way to treat cancers in which the Hh is overexpressed. It is currently being investigated as a treatment agent in basal cell carcinoma, medulloblastoma, and rhabdomyosarcoma, which are tumors that result from excessive Hh activity, glioblastoma, and as a treatment agent for multiple myeloma.

Cyclopamine has thus far been described from the California corn lily *Veratrum californicum* and the Japanese species *Veratrum glandiflorum*. Cyclopamine is of pharmacological interest as a Hedgehog signaling pathway inhibitor. Cyclopamine was discovered to inhibit the Hedgehog signaling pathway by direct binding to the G protein-coupled receptor Smoothened. As such, it has shown promising antineoplastic activities against several cancers in which Hedgehog signaling pathway malfunction is implicated, including pancreatic cancer, renal cell carcinoma, medulloblastoma, and leukemia. A semi-synthetic analog of cyclopamine, IPI-926, has been in clinical trials for treatment of several cancers including metastatic solid tumors, pancreatic cancer and leukemia. Due to a complicated total synthesis, wild-collected *V. californicum* is the current source of cyclopamine. Cultivation of the plant has not been achieved. Coupled with slow growth in the wild, this makes cyclopamine an attractive target for biotechnological production.

Little is known about the cyclopamine biosynthetic pathway. Studies performed in the 1960's and 1970's on *V. californicum* and *V. grandiflorum* provide a general framework for the pathway and described hypothetical precursors, intermediates, and related compounds found in planta. Cholesterol has been shown to be a common precursor to the steroid alkaloids in this and similar pathways. Thus far, none of the genes involved in cyclopamine biosynthesis has been identified.

In view of the potential importance of cyclopamine and verazine metabolite derivatives with improved properties as a cancer therapeutics, the need for adequate supplies of these compounds to facilitate development of these molecules for patients, the complex chemical synthesis of cyclopamine, and the supply constraints imposed by wild collection of the source plant *Veratrum californicum*, there is a need in the art for methods to enhance the accumulation of this compound in plants via the development of a synthetic biology production platform. Engineering of the cyclopamine biosynthetic pathway into an easily cultivated host plant can result in an economically attractive, sustainable supply of this drug to meet future market demand. However, improved in planta production requires knowledge of the underlying biosynthetic genes, which is currently lacking.

SUMMARY

Accordingly, to address this need, disclosed herein is a broadly applicable biosynthetic gene discovery method based on correlating cyclopamine accumulation with RNAseq gene expression data.

Figure 16A:
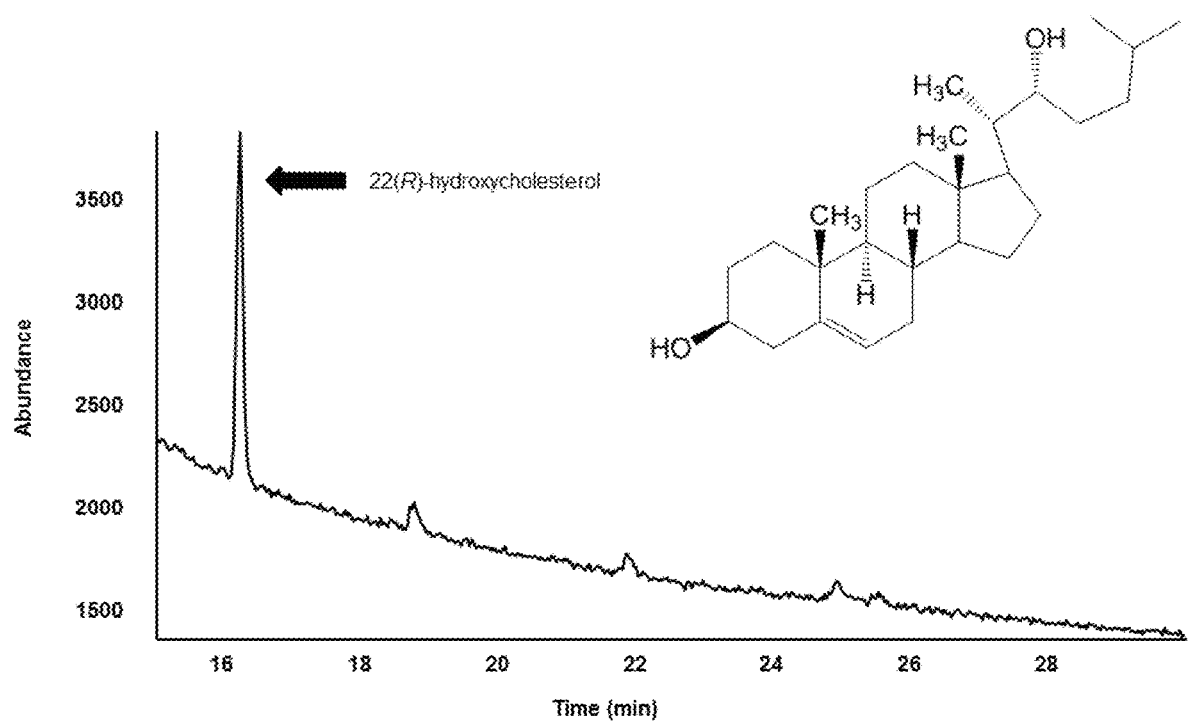
Figure 16B:
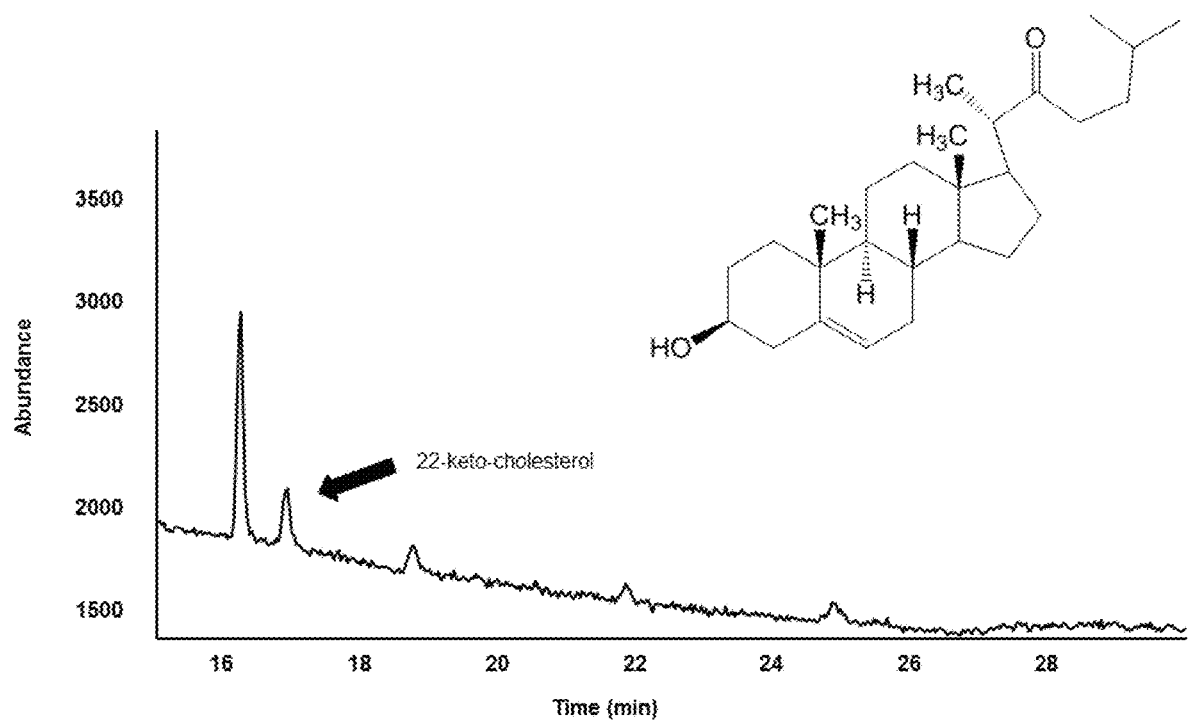

Further scope of the applicability of the presently disclosed embodiments will become apparent from the detailed description and drawings provided below. However, it should be understood that the detailed description and specific examples, while indicating preferred embodiments of this disclosure, are given by way of illustration only since various changes and modifications within the spirit and scope of these embodiments will become apparent to those skilled in the art from this detailed description.

BRIEF DESCRIPTION OF THE DRAWINGS

The foregoing and other aspects, features, and advantages of the present disclosure will be better understood from the following detailed description taken in conjunction with the accompanying figures, all of which are given by way of illustration only, and are not limitative of the present specification, in which:

FIGS. 1A, B. Enzyme assay workflow for clarification of cyclopamine biosynthetic pathway. FIGS. 1A and 1B show assays were performed with crude *S. frugiperda* Sf9 cells infected with baculovirus containing select *V. californicum* genes. Each arrow represents an extraction step; the resulting product was utilized as substrate for the subsequent enzyme assay. All cytochromes P450 were co-expressed with *E. californica* cytochrome P450 reductase (CPR). (1A) 12 assays each of 22-hydroxycholesterol 26-hydroxylase/oxidase, 22-hydroxy-26-aminocholesterol 22-oxidase, and control cytochrome P450 each with pure 22(R)-hydroxycholesterol were incubated and extracted. Dried extracts from each were split according to panel A. Final extracts were analyzed by gas chromatography mass spectrometry with results shown in FIGS. 16A and 16B. (1B) 8 assays of cholesterol 22-hydroxylase and 22-hydroxycholesterol 26-hydroxylase/oxidase and 8 assays of cholesterol 22-hydroxylase and 22-hydroxy-26-aminocholesterol 22-oxidase were incubated and extracted. Dried extracts were split and used as substrate in 2 more enzyme assays, 4 reactions each. These were extracted then split into 2 more assays, 2 reactions each. Products at each step were analyzed by liquid chromatography mass spectrometry with results shown in FIGS. 11A and 11B.

Figure 2:
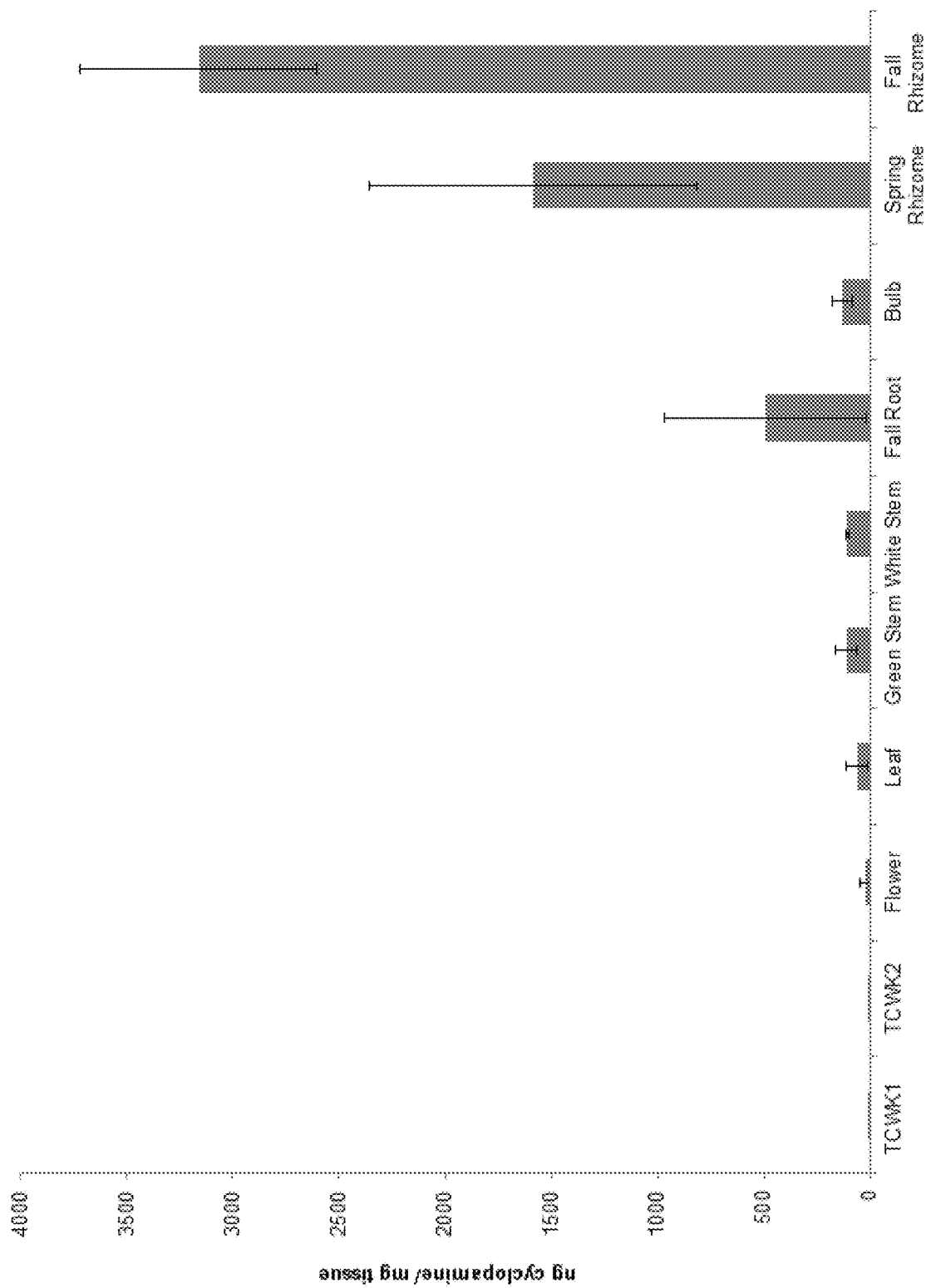

FIG. 2. Cyclopamine accumulation profile in *V. californicum*. Each V californicum tissue underwent three independent ethanol extractions followed by liquid chromatography mass spectrometry analysis on a 4000 QTRAP. Quantitation with authentic cyclopamine was accomplished using a standard curve with peak areas. Each value represents ng of alkaloid per mg of tissue; error bars representing standard deviation. Sample dilutions were as follows: 10 fold for tissue culture samples, 1000 fold for flower, 5000 fold for leaf and stem, and 10000 fold for root, bulb, and rhizome. TCWK1 and TCWK2 stand for tissue culture one- and two-weeks after transfer to new media, respectively.

Figure 3:
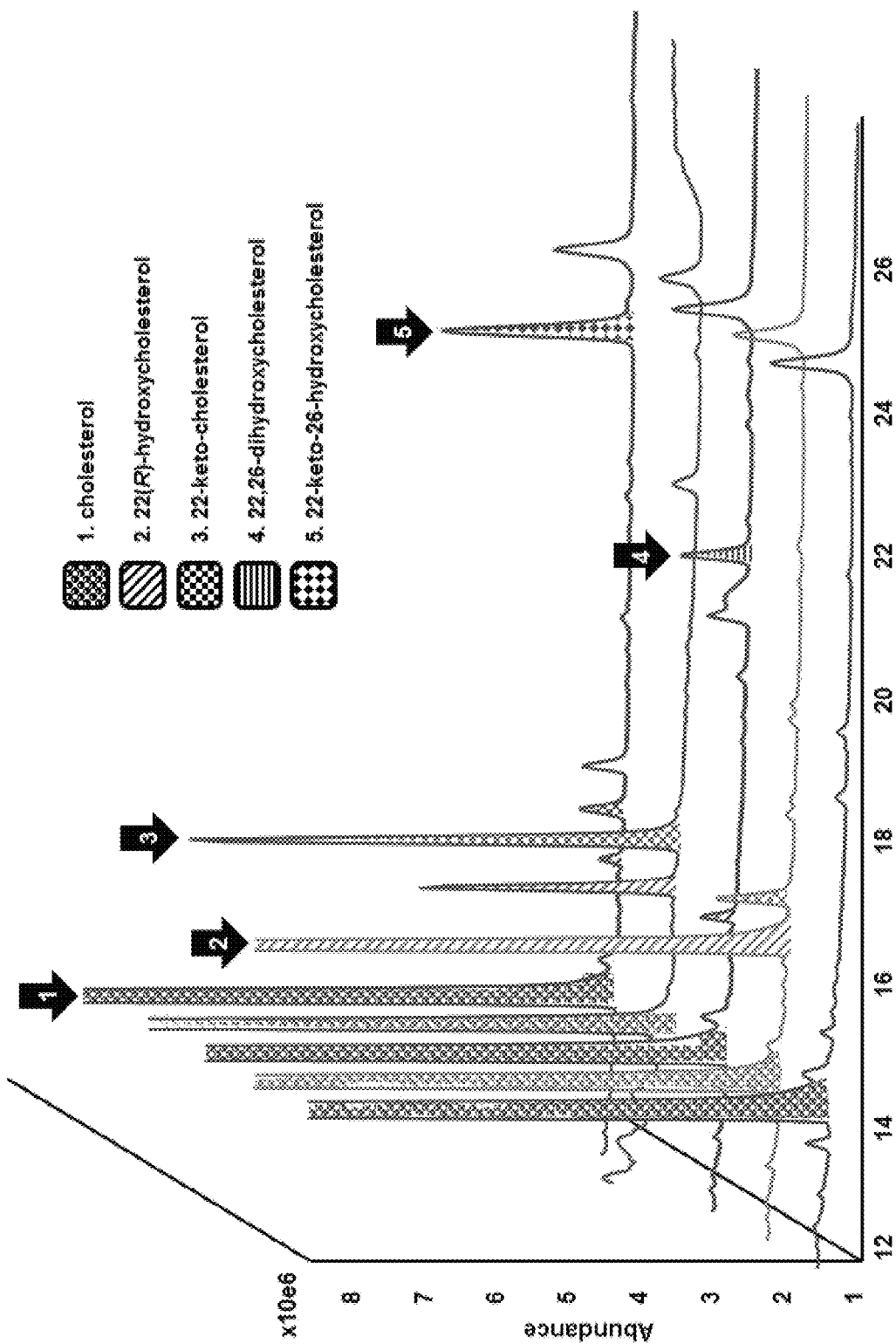

FIG. 3. GC-MS Overlay of *S. frugiperda* Sf9 extracts expressing *V. californicum* genes. Extracts of *S. frugiperda* Sf9 cells infected with several combinations of Baculovirus containing genes from *V. californicum* were extracted and analyzed by gas chromatography mass spectrometry. Each colored chromatograph corresponds to the following: Red-control cytochrome P450+CPR, Orange-cholesterol 22-hydroxylase+CPR, Green-cholesterol 22-hydroxylase+22-hydroxycholesterol 26-hydroxylase/oxidase+CPR, Blue-cholesterol 22-hydroxylase+22-hydroxy-26-aminocholesterol 22-oxidase+CPR, Purple-cholesterol 22-hydroxylase+22-hydroxycholesterol 26-hydroxylase/oxidase+22-hydroxy-26-aminocholesterol 22-oxidase+CPR. Metabolites are numbered according to the legend and shaded for clarity. CPR refers to the cytochrome P450 reductase from *Eschscholzia californica* and control P450 refers to CYP719A14 cheilanthifoline synthase from *Argemone mexicana*.

FIGS. 4A-D. LC-MS/MS of *S. frugiperda* Sf9 extracts expressing V californicum genes. FIGS. 4A, 4B, 4C and 4D show *S. frugiperda* Sf9 cells infected with several combinations of Baculovirus containing select genes from *V. californicum* were extracted and analyzed by liquid chromatography mass spectrometry with method stated above. (4A) Extract of *S. frugiperda* Sf9 infection with cholesterol 22-hydroxylase, 22-hydroxycholesterol 26-hydroxylase/oxidase, 22-hydroxycholesterol-26-al transaminase, and CPR, (4B) extract of *S. frugiperda* Sf9 infection with cholesterol 22-hydroxylase, 22-hydroxycholesterol 26-hydroxylase/oxidase, 22-hydroxy-26-aminocholesterol 22-oxidase, and CPR, (4C) extract of *S. frugiperda* Sf9 infection with cholesterol 22-hydroxylase, 22-hydroxycholesterol 26-hydroxylase/oxidase, 22-hydroxycholesterol-26-al transaminase, 22-hydroxy-26-aminocholesterol 22-oxidase, and CPR, (4D) extract of *S. frugiperda* Sf9 infection with cholesterol 22-hydroxylase, 22-hydroxycholesterol 26-hydroxylase/oxidase, 22-hydroxy-26-aminocholesterol 22-oxidase, *S. lycopersicum* GABA transaminase isozyme 2, and CPR. MRM signals for each metabolite were combined and shaded for clarity. CPR refers to *E. californica* cytochrome P450 reductase.

Figure 5:
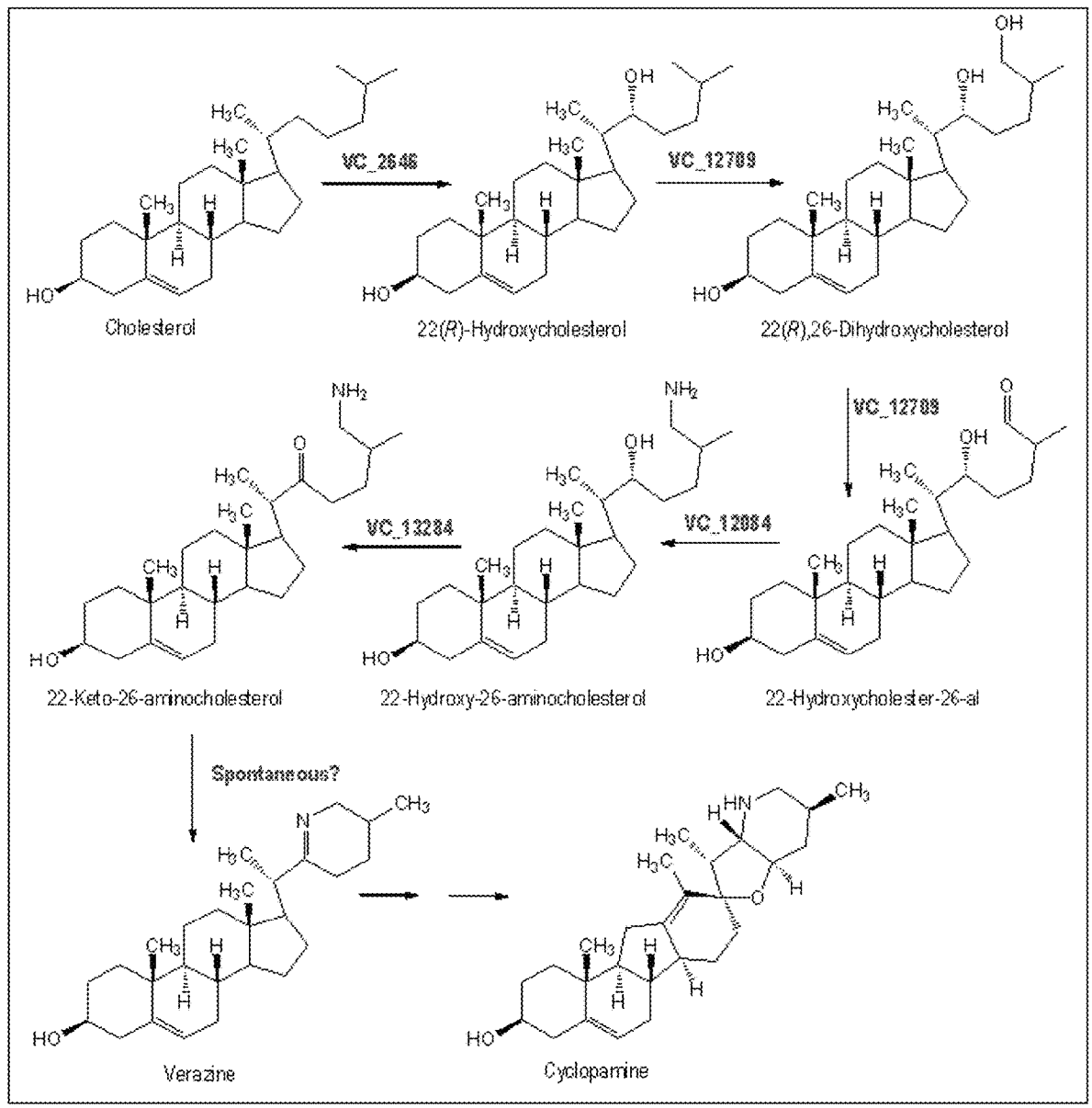

FIG. 5. Proposed *V. californicum* cyclopamine biosynthetic pathway leading from cholesterol. Cholesterol is first hydroxylated at position C-22 in the R-orientation by cholesterol 22-hydroxylase, followed by hydroxylation/oxidation at position C-26 by 22-hydroxycholesterol 26-hydroxylase/oxidase. Next, a transamination reaction by 22-hydroxycholesterol-26-al transaminase transfers an amino group from γ-aminobutyric acid to the C-26-aldehyde, forming 22-hydroxy-26-aminocholesterol. The C-22-hydroxy group is then oxidized to a ketone by 22-hydroxy-26-aminocholesterol 22-oxidase to form 22-keto-26-aminocholesterol, a reactive intermediate that quickly cyclizes to verazine.

Figure 6A:
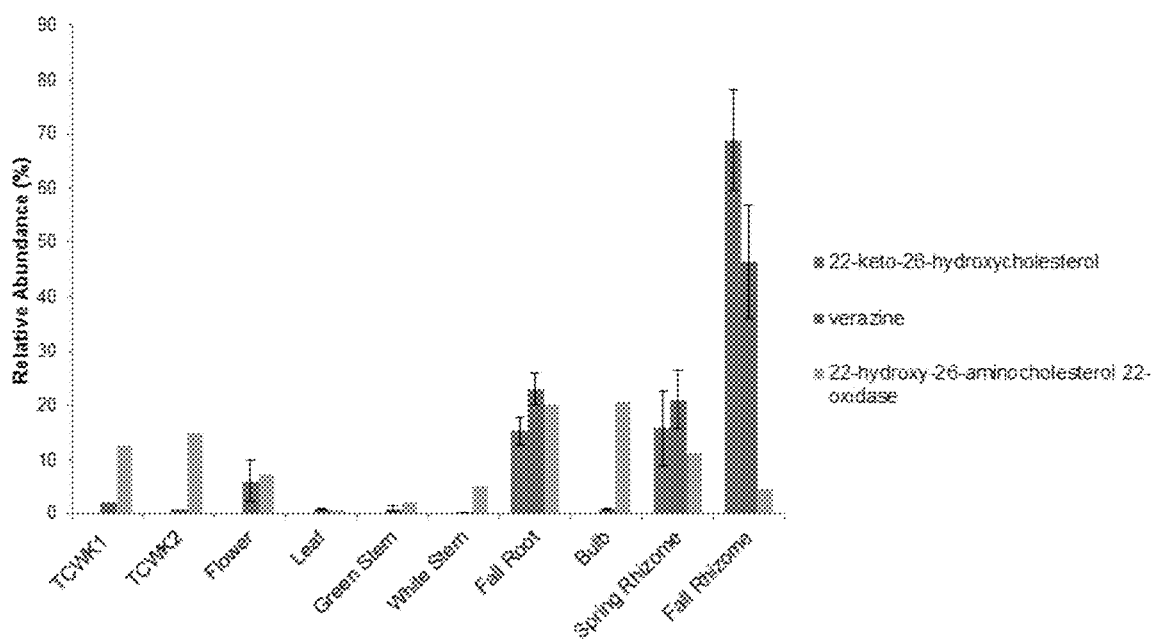
Figure 6B:
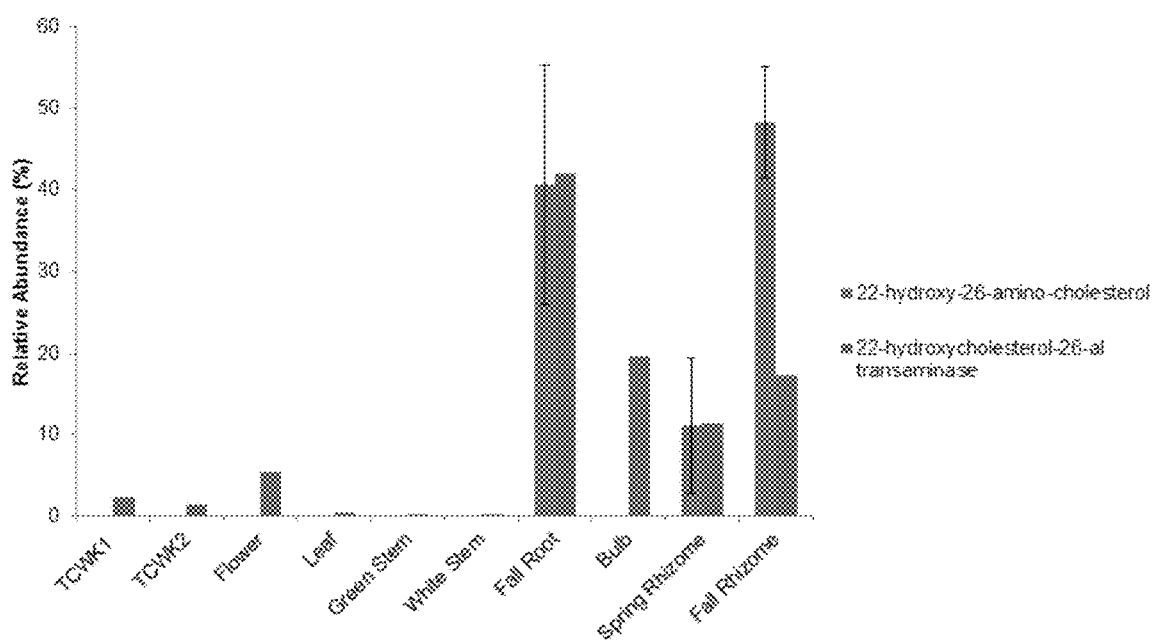

FIGS. 6A, B. Relative accumulation of select *V. californicum* metabolites and transcript abundance of biosynthetic genes per tissue type. FIGS. 6A and 6B show relative quantities of metabolites are shown by percent of total peak area, error bars show standard deviation for three replicates as determined by LC-MS/MS; quantities of transcript abundance are represented by percent of total reads. (6A) A comparison of relative amounts of 22-keto-26-hydroxycholesterol and verazine to 22-hydroxy-26-aminocholesterol 22-oxidase, and (6B) a comparison of 22-hydroxy-26-aminocholesterol to 22-hydroxycholesterol-26-al transaminase as determined by liquid chromatography mass spectrometry (metabolites) and read alignments to assembled transcriptome (gene transcripts). TCWK1 and TCWK2 stand for tissue culture one- and two-weeks after transfer for new media, respectively.

Figure 7:
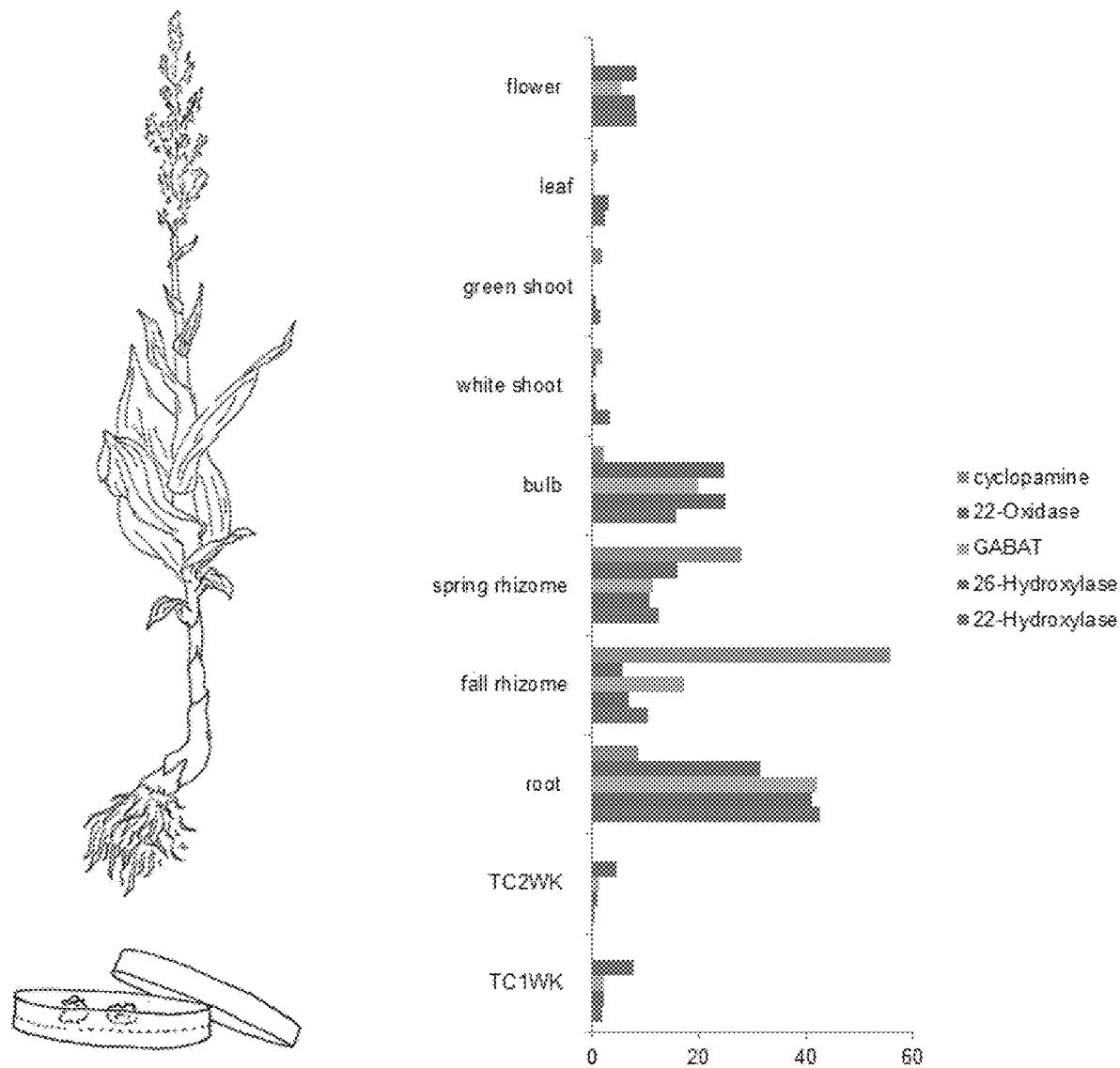

FIG. 7. Cyclopamine accumulation vs gene expression of steroidal alkaloid biosynthetic genes. The presented tissues types from *V. californicum* were extracted and analyzed by liquid chromatography mass spectrometry for cyclopamine amount. Transcript abundance was analyzed by alignment of individual reads to the assembled transcriptome for gene expression. Both gene expression and cyclopamine accumulation are shown as a percent of the total for comparison. The abbreviation TC1WK and TC2WK stands for tissue culture one and two weeks after transfer to fresh media (respectively).

Figure 8:
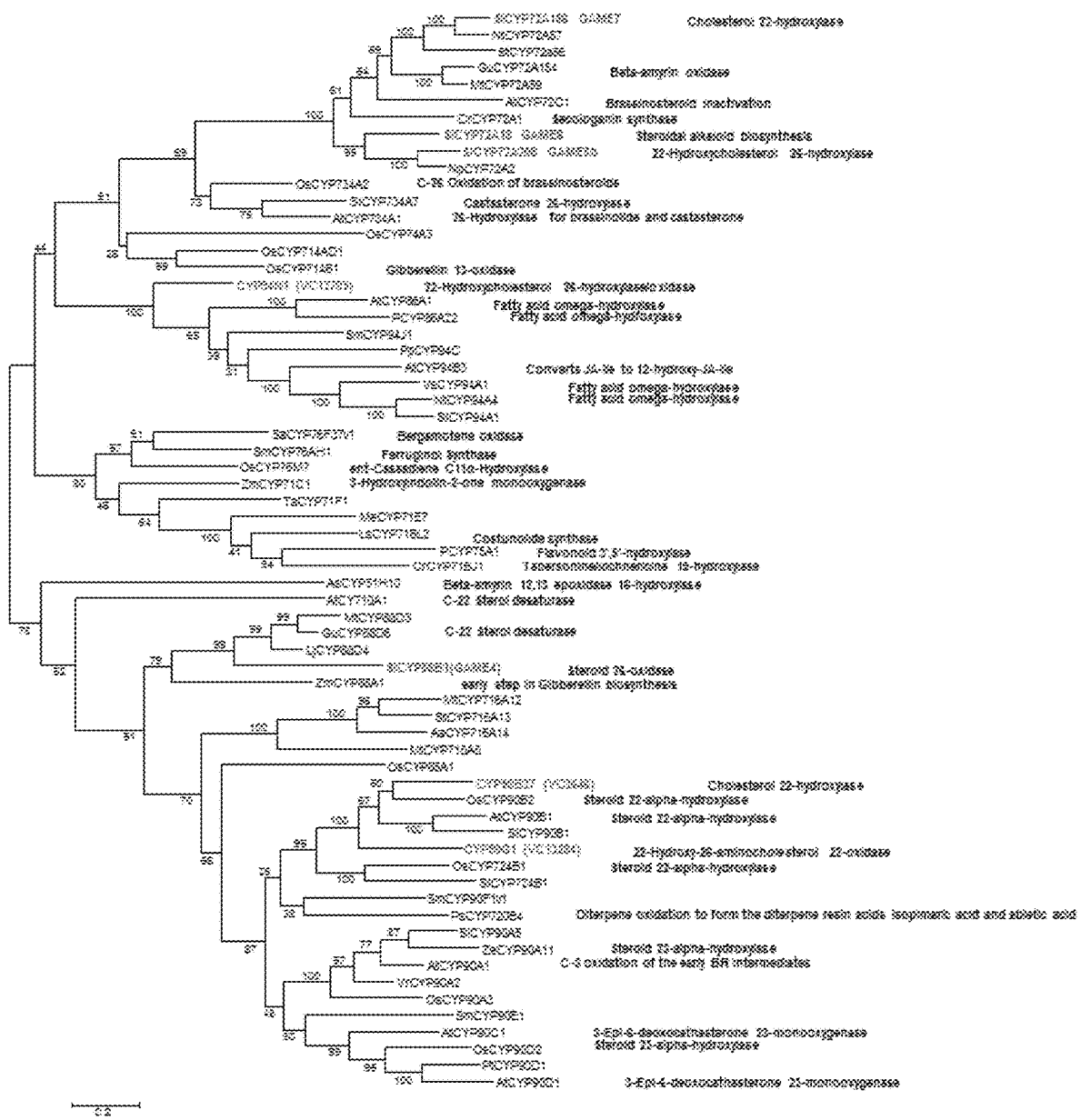

FIG. 8. Phylogenetic tree of select plant cytochrome P450 enzymes. Nucleotide sequences obtained from Genbank, Uniprot, and the Sol Genomics Network of select cytochrome P450 enzymes were aligned by codon with the Muscle algorithm. Only experimentally determined functions are designated in the figure. Phylogenetic reconstruction was performed using the Maximum likelihood statistical method with bootstrapping in MEGA version 6.06 with default parameters.

Figure 9:
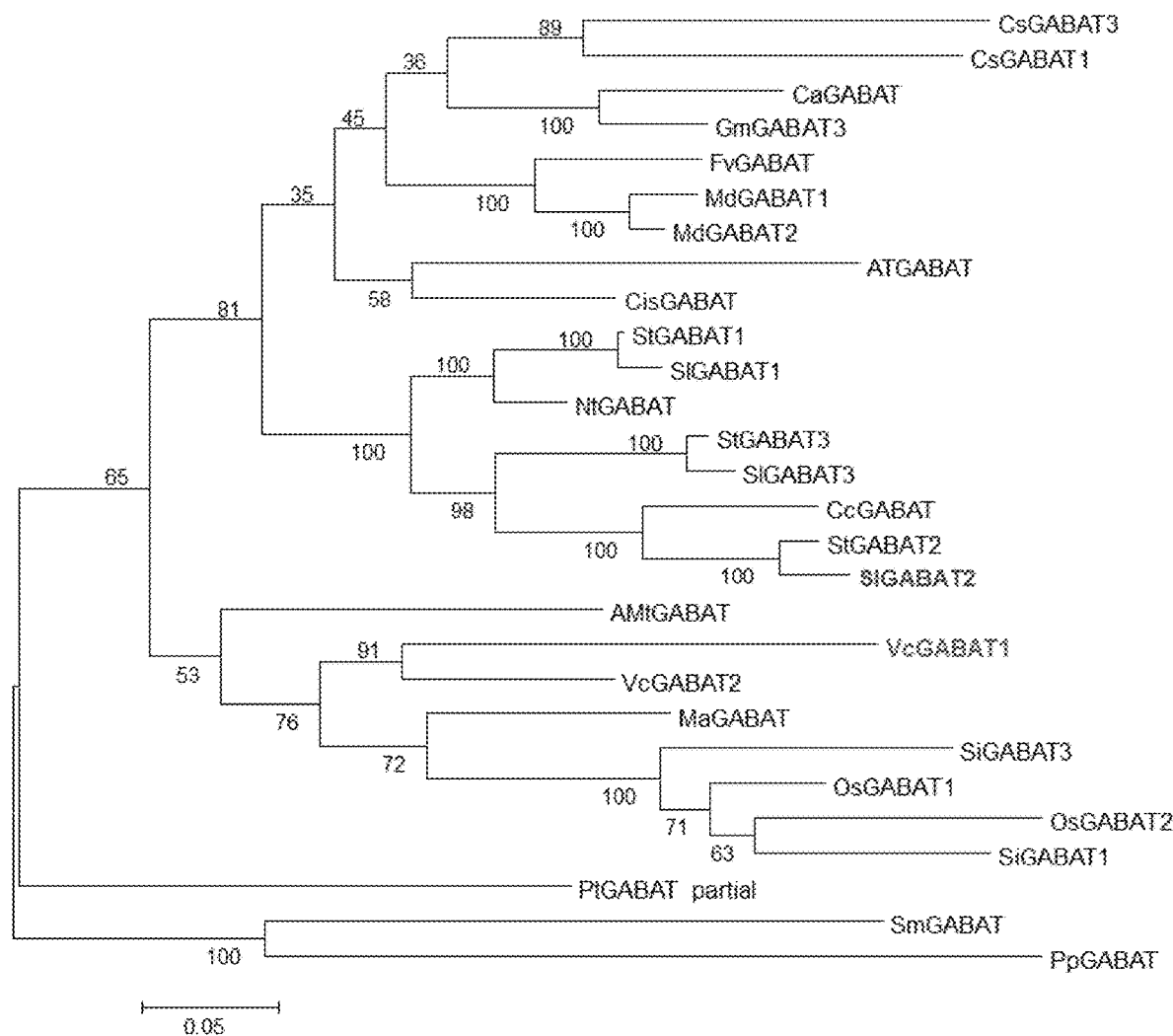

FIG. 9. Phylogenetic tree of select γ-aminobutyrate transaminases (GABATS). Nucleotide sequences obtained from Genbank and Dendrome of select GABA-transaminases were aligned with the Muscle algorithm. Phylogenetic reconstruction was performed using the Maximum likelihood statistical method with bootstrapping in MEGA version 6.06 with default parameters.

Figure 10:
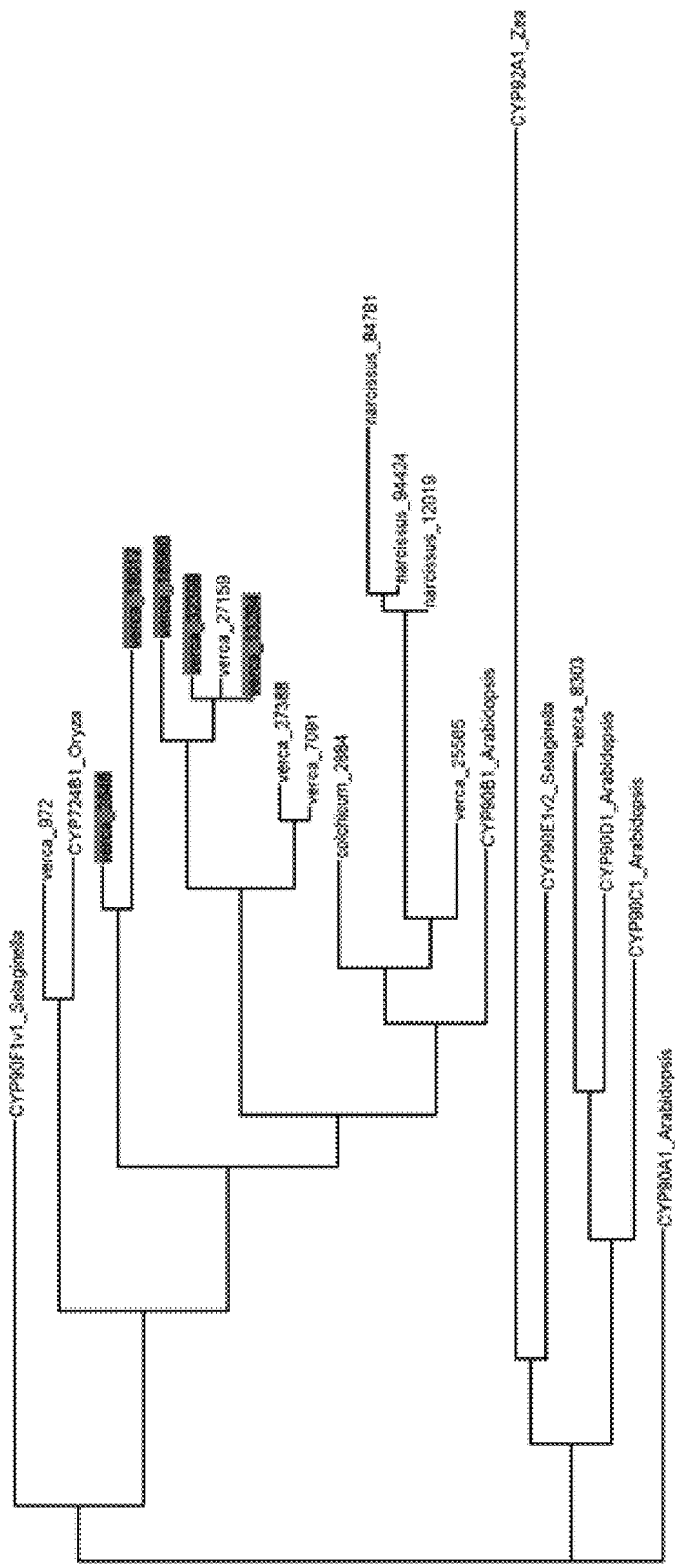

FIG. 10. Neighbor-joining phylogeny of CYP90B1 members. Candidate genes from Haystack are highlighted in red.

Figures 11A, 11B:
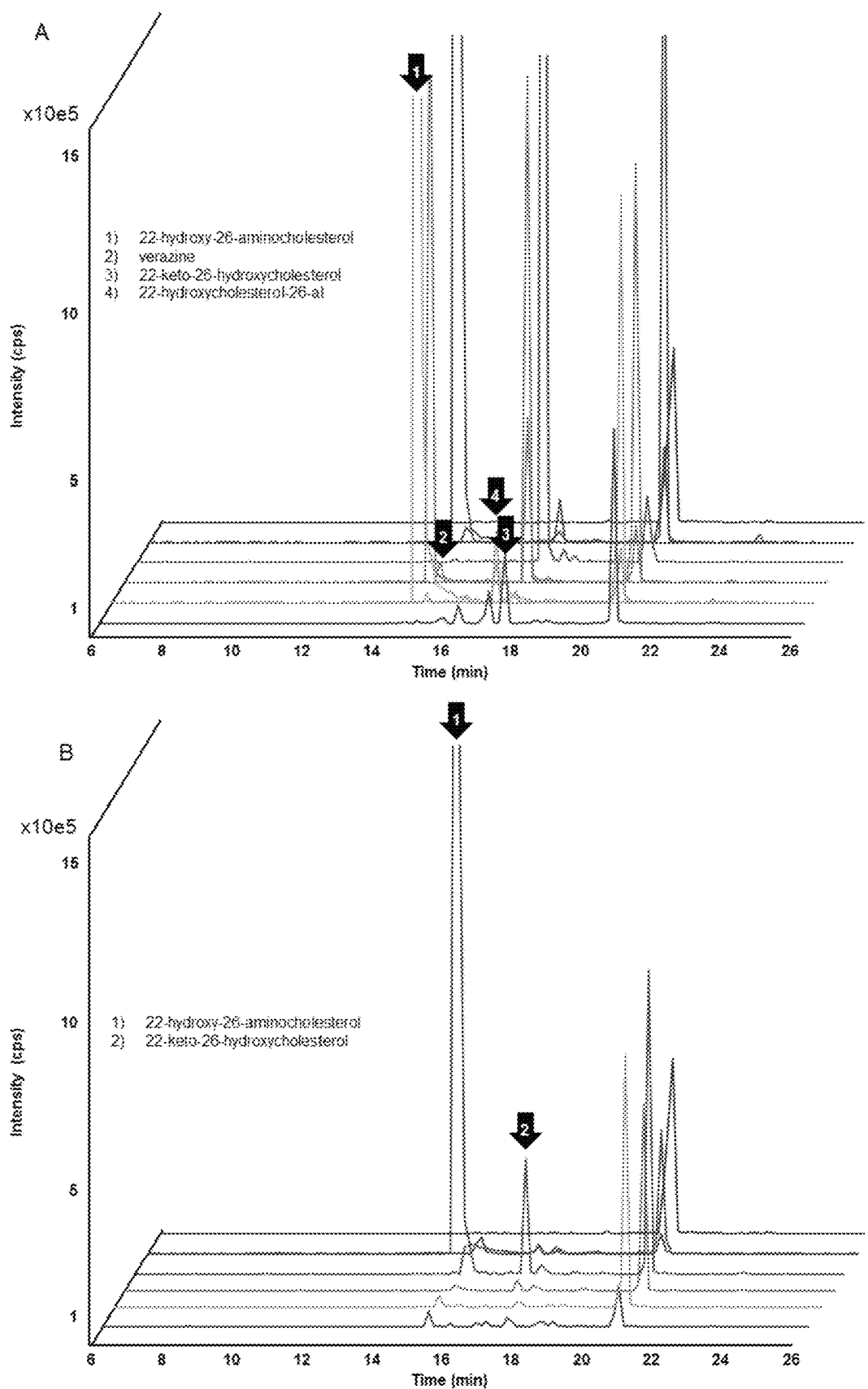

FIGS. 11A, B. Enzyme Assays for biosynthetic pathway order clarification in *V. californicum* using LC-MS/MS. FIGS. 11A and 11B show enzyme assays were performed as described in FIG. 1B using crude *S. frugiperda* Sf9 cells infected with baculovirus containing each *V. californicum* gene. All cytochromes P450 were co-expressed with *E. californica* cytochrome P450 reductase (CPR); 22-hydroxycholesterol-26-al transaminase was expressed alone. Cholesterol substrate for each initial reaction was provided by *S. frugiperda* Sf9 cells. Extracts were taken at each step and analyzed by liquid chromatography mass spectrometry. Chromatographs for each sample are a combination of product ions for clarity. (11A) Chromatograms of assays run initially with cholesterol 22-hydroxylase combined with 22-hydroxycholesterol 26-hydroxylase/oxidase. Each colored chromatograph corresponds to the following: Red-cholesterol 22-hydroxylase+22-hydroxycholesterol 26-hydroxylase/oxidase, Orange-cholesterol 22-hydroxylase+22-hydroxycholesterol 26-hydroxylase/oxidase, extracted, then added as substrate to assay with 22-hydroxycholesterol-26-al transaminase, Green-cholesterol 22-hydroxylase+22-hydroxycholesterol 26-hydroxylase/oxidase, extracted, then added as substrate to assay with 22-hydroxycholesterol-26-al transaminase, extracted, and added as substrate to 22-hydroxy-26-aminocholesterol 22-oxidase, Blue-cholesterol 22-hydroxylase+22-hydroxycholesterol 26-hydroxylase/oxidase extracted and added as substrate to 22-hydroxy-26-aminocholesterol 22-oxidase, Purple-cholesterol 22-hydroxylase+22-hydroxycholesterol 26-hydroxylase/oxidase, extracted, and added as substrate to 22-hydroxy-26-aminocholesterol 22-oxidase, extracted, and added as substrate to 22-hydroxycholesterol-26-al transaminase, Grey-CPR only control. (11B) Chromatograms of assays run initially with cholesterol 22-hydroxylase+22-hydroxy-26-aminocholesterol 22-oxidase. Each colored chromatogram corresponds to the following: Red-cholesterol 22-hydroxylase+22-hydroxy-26-aminocholesterol 22-oxidase, Orange-cholesterol 22-hydroxylase+22-hydroxy-26-aminocholesterol 22-oxidase, extracted, and added as substrate to 22-hydroxycholesterol-26-al transaminase, Green-cholesterol 22-hydroxylase+22-hydroxy-26-aminocholesterol 22-oxidase, extracted, and added as substrate to 22-hydroxycholesterol-26-al transaminase, extracted, then added as substrate to 22-hydroxycholesterol 26-hydroxylase/oxidase, Blue-cholesterol 22-hydroxylase+22-hydroxy-26-aminocholesterol 22-oxidase, extracted, and added as substrate to 22-hydroxycholesterol 26-hydroxylase/oxidase, Purple-cholesterol 22-hydroxylase+22-hydroxy-26-aminocholesterol 22-oxidase, extracted, and added as substrate to 22-hydroxycholesterol 26-hydroxylase/oxidase, extracted, then added as substrate to 22-hydroxycholesterol-26-al transaminase, Grey-CPR only control.

FIGS. 12A, B. Orbitrap structural analysis. FIGS. 12A and 12B show purified (12A) 22-hydroxy-26-aminocholesterol and (12B) verazine were analyzed by high-resolution mass spectrometry for structural identification. Key fragments for each are shown.

FIGS. 13A-C. SDS-PAGE of heterologously expressed *V. californicum* cytochromes P450 in *S. frugiperda* Sf9 cells. FIGS. 13A, 13B and 13C show *S. frugiperda* Sf9 cell extracts expressing *V. californicum* cytochromes P450 co-expressed with *E. californica* cytochrome P450 reductase (CPR) was analyzed by SDS-PAGE and visualized by Coomassie Blue staining. (13A) Lane 1, protein standards; lane 2-4, independent preparations of cholesterol 22-hydroxylase; lane 5, *S. frugiperda* Sf9 cell expression CPR only; lane 6, 0.3 μg bovine serum albumin (BSA); lane 7, 0.6 μg BSA; lane 8, 1.2 μg BSA; lane 9, 1.8 μg BSA; lane 10, replicate of lane 2. (13B) Lane 1, loading buffer only; lane 2, 1.8 μg BSA; lane 3, 1.2 μg BSA; lane 4, 0.6 μg BSA; lane 5, loading buffer only; lane 6-8, independent preparations of 22-hydroxycholesterol 26-hydroxylase/oxidase; lane 9, CPR only; lane 10, protein standards. (13C) Lane 1, loading buffer only; lane 2, 0.6 μg BSA; lane 3, 1.2 μg BSA; lane 4, 1.8 μg BSA; lane 5, CPR only; lane 6-9, independent preparations of 22-hydroxy-26-aminocholesterol 22-oxidase; lane 10, protein standards.

FIGS. 14A, B. Expression profile of *V. californicum* genes involved in the biosynthesis of steroidal alkaloids from Illumina RNAseq and semi-quantitative RT-PCR. FIGS. 14A and 14B show relative abundance is based on percent of the total for each gene, normalized to the total number of reads or total density. (14A) Cleaned Illumina reads were mapped to assembled contigs to obtain alignment data. (14B) Band density of semi-quantitative RT-PCR was used for quantitation.

FIGS. 15A, B. GC-MS analysis of select *V. californicum* cytochrome P450 enzymes with cholesterol. FIGS. 15A and 15B show enzyme assays were extracted and derivatized before GC-MS analysis. (15A) Overlay of enzyme assays performed with either cholesterol 22-hydroxylase or 22-hydroxy-26-aminocholesterol 22-oxidase using cholesterol as substrate. Both cytochrome P450 enzymes were co-expressed with *E. californica* cytochrome P450 reductase (CPR). 22(R)-Hydroxycholesterol pure standard was included for reference. (15B) Enzyme assay of 22-hydroxycholesterol 26-hydroxylase/oxidase co-expressed with CPR with cholesterol as substrate overlain with pure 26-hydroxycholesterol for reference.

FIGS. 16A-F. Enzyme assays for biosynthetic pathway order clarification in *V. californicum* using GC-MS. FIGS. 16A, 16B, 16C, 16D, 16E and 16F show assays were completed according to FIG. 1A and analyzed by gas chromatography mass spectrometry. (16A) Assay with control cytochrome P450 co-expressed with *E. californica* cytochrome P450 reductase (CPR) and authentic 22(R)-hydroxycholesterol was extracted, dried, and used as substrate in an assay with the same control cytochrome P450+CPR. (16B) Assay with 22-hydroxy-26-aminocholesterol 22-oxidase+CPR and 22(R)-hydroxycholesterol was extracted and used as substrate in assay with control cytochrome P450+CPR. (16C) Assay with 22-hydroxy-26-aminocholesterol 22-oxidase+CPR and 22(R)-hydroxycholesterol was extracted and used as substrate in assay with 22-hydroxycholesterol 26-hydroxylase/oxidase+CPR. (16D) Assay with 22-hydroxycholesterol 26-hydroxylase/oxidase+CPR was extracted and used as substrate in assay with control cytochrome P450+CPR. (16E) Assay with 22-hydroxycholesterol 26-hydroxylase/oxidase+CPR and 22(R)-hydroxycholesterol was extracted and used as substrate in assay with 22-hydroxy-26-aminocholesterol 22-oxidase+CPR. (16F) Schematic of possible transformation order; red X indicating which reaction was not observed. Ion 187 was extracted for the presented chromatograms.

FIG. 17. Dimedone aldehyde trapping experiment. *S. frugiperda* Sf9 cell extracts expressing *V. californicum* cholesterol 22-hydroxylase co-expressed with *E. californica* cytochrome P450 reductase (CPR) and *V. californicum*

22-hydroxycholesterol 26-hydroxylase/oxidase co-expressed with CPR were mixed for enzyme assay using cholesterol provided by the crude cell extract as substrate. Assays performed without dimedone (blue) and with dimedone (red) were analyzed by liquid chromatography mass spectrometry. Chromatograms were obtained by overlay of Enhanced Product Ion scans (EPI) for molecular mass 417.

Figure 18:
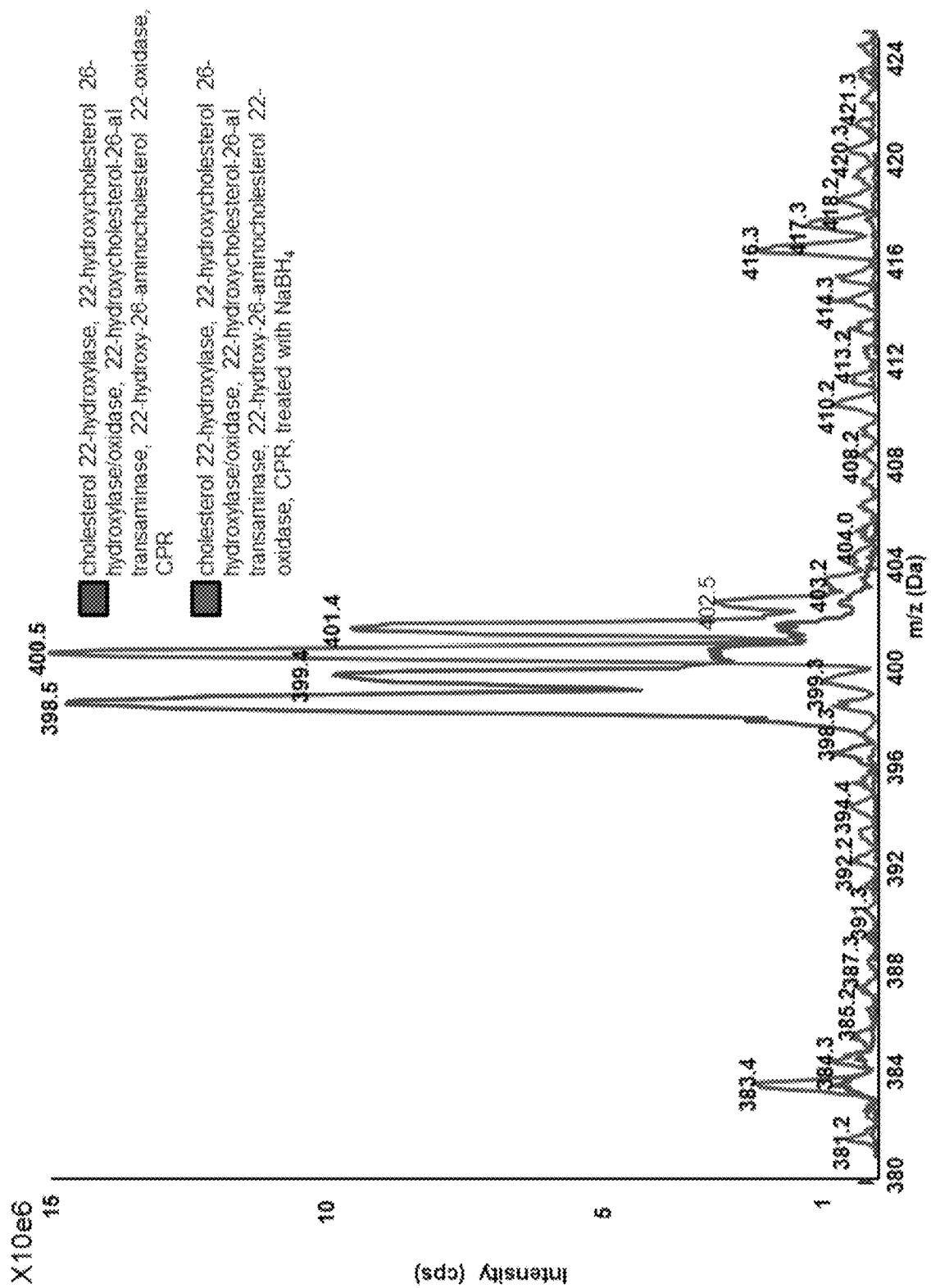

FIG. 18. Borohydride reduction of verazine. *S. frugiperda* Sf9 cells expressing the *V. californicum* genes cholesterol 22-hydroxylase, 22-hydroxycholesterol 26-hydroxylase/oxidase, 22-hydroxycholesterol-26-al transaminase, 22-hydroxy-26-aminocholesterol 22-oxidase, and *E. californica* cytochrome P450 reductase were extracted and analyzed by liquid chromatography mass spectrometry either directly (blue) or after treatment with $NaBH_4$ (red). Enhance MS scans detecting ions 380-425 m/z are presented.

Figure 19A:
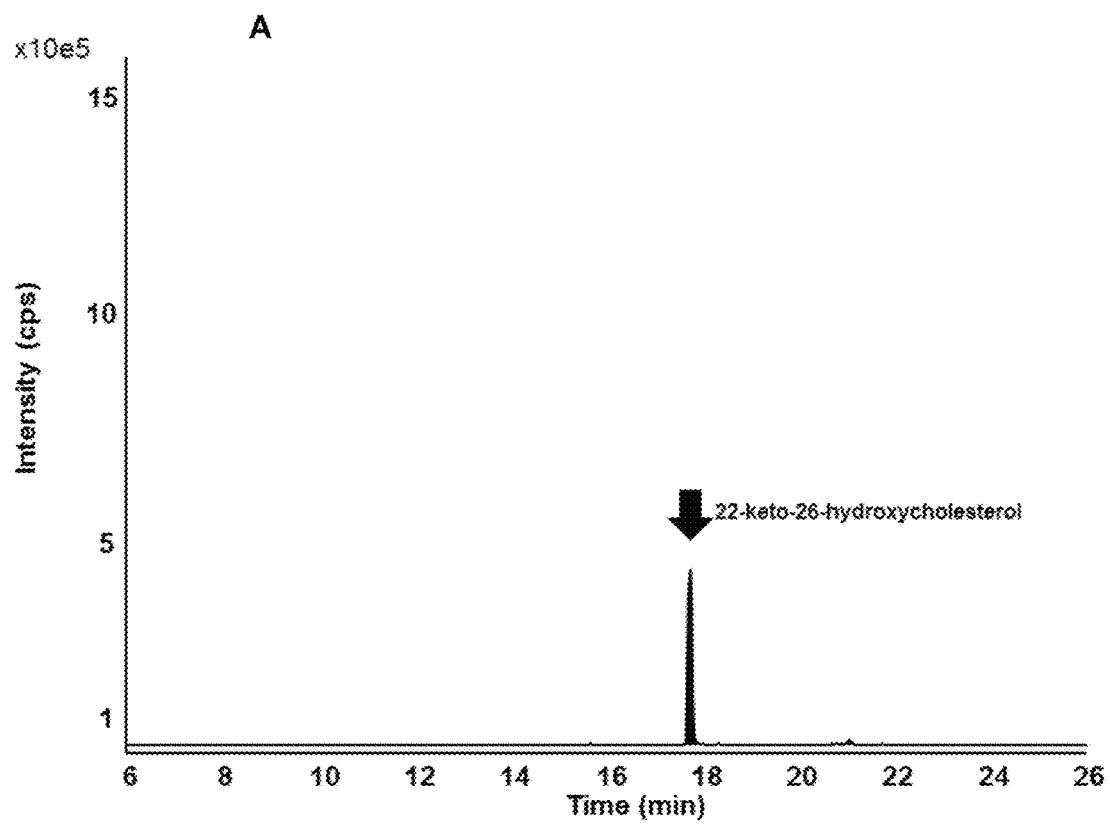
Figure 19B:
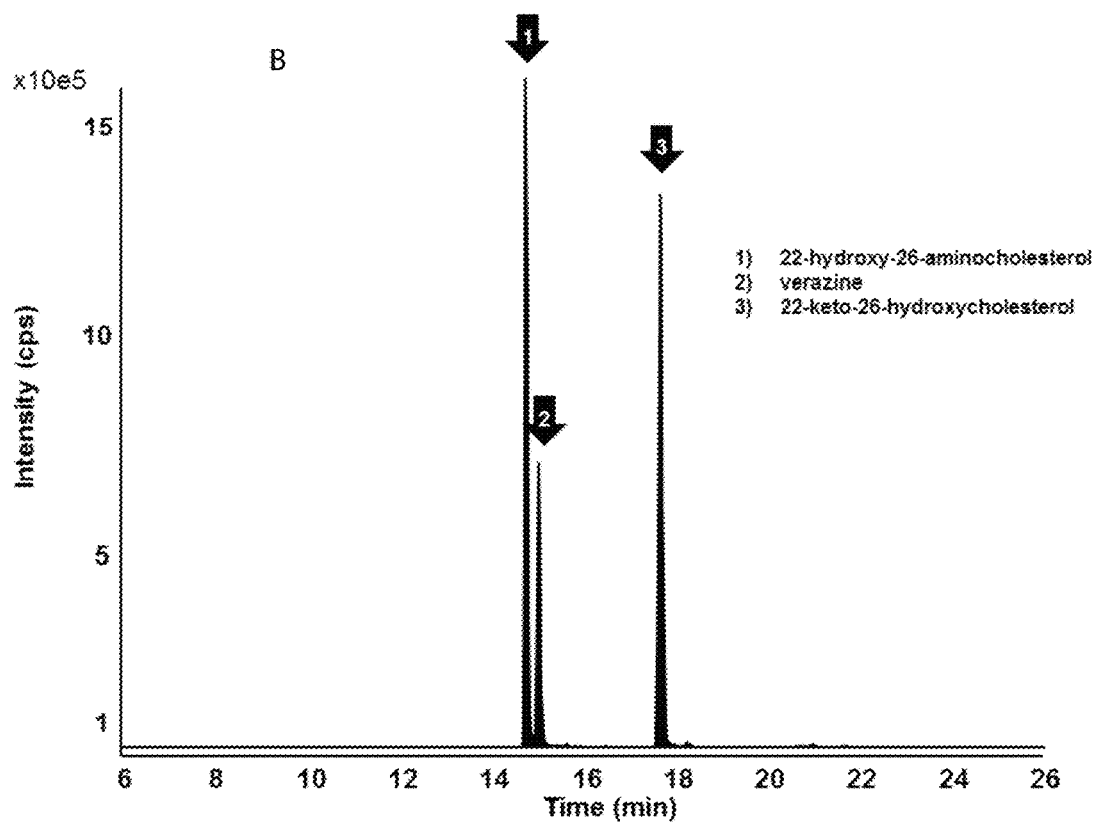

FIGS. 19A, B. LC-MS/MS analysis of *V. californicum* contig 674 (GABA transaminase 2). FIGS. 19A and 19B show *S. frugiperda* Sf9 cells were co-transformed with *E. californica* cytochrome P450 reductase, *V. californicum* cytochrome P450 enzymes: cholesterol 22-hydroxylase, 22-hydroxycholesterol 26-hydroxylase/oxidase, 22-hydroxy-26-aminocholesterol 22-oxidase, and (19A) Contig 674 or (19B) 22-hydroxycholesterol-26-al transaminase. Extracts were analyzed by LC-MS/MS; ions for each peak were combined and shaded for clarity.

Figure 20:
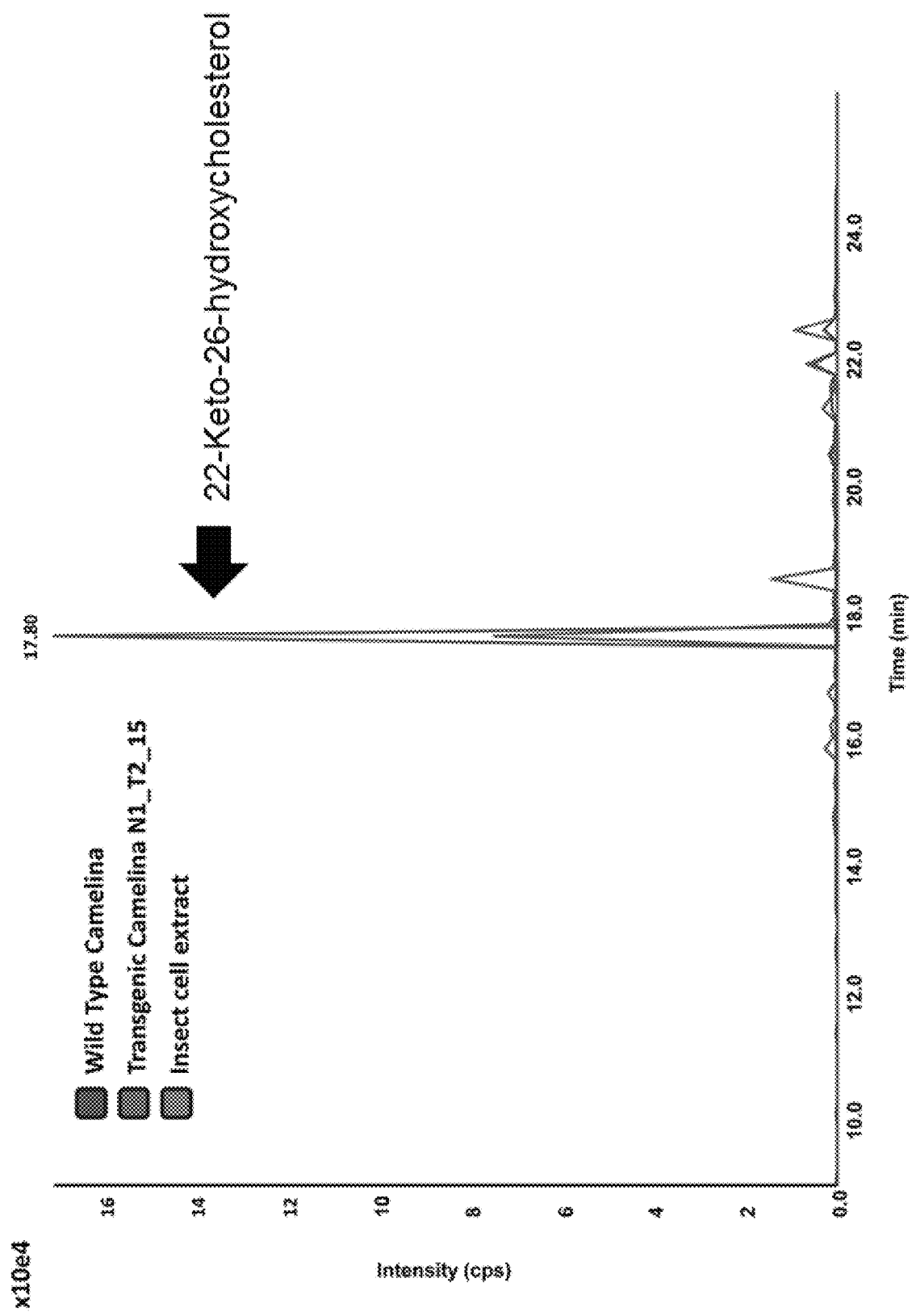

FIG. 20. 22-Keto-26-hydroxycholesterol in refactored *S. frugiperda* Sf9 cells and *Camelina sativa*. Extracts were analyzed by liquid chromatography mass spectrometry using MRM mode for ion 417/271. Blue-wild type camelina seed extract, Red-transgenic camelina seed extract expressing cholesterol 22-hydroxylase, 22-hydroxycholesterol 26-hydroxylase/oxidase, 22-hydroxy-26-aminocholesterol 22-oxidase, and 22-hydroxycholesterol-26-al transaminase, Green-*S. frugiperda* Sf9 cells expressing cholesterol 22-hydroxylase, 22-hydroxycholesterol 26-hydroxylase/oxidase, 22-hydroxy-26-aminocholesterol 22-oxidase, 22-hydroxycholesterol-26-al transaminase, CPR.

Figure 21:
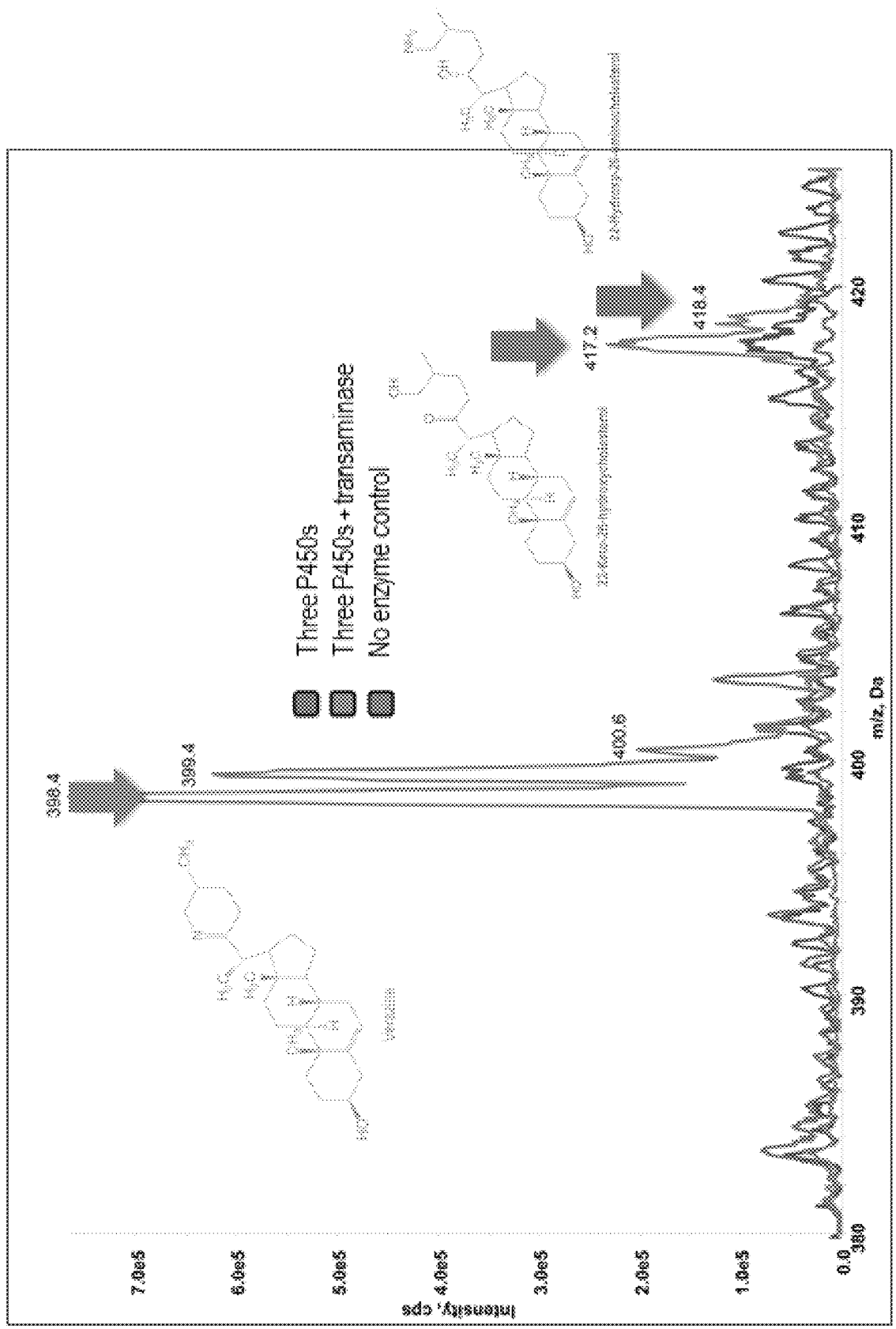
Figures 22A, 22B, 22C, 22D, 22E, 22F:
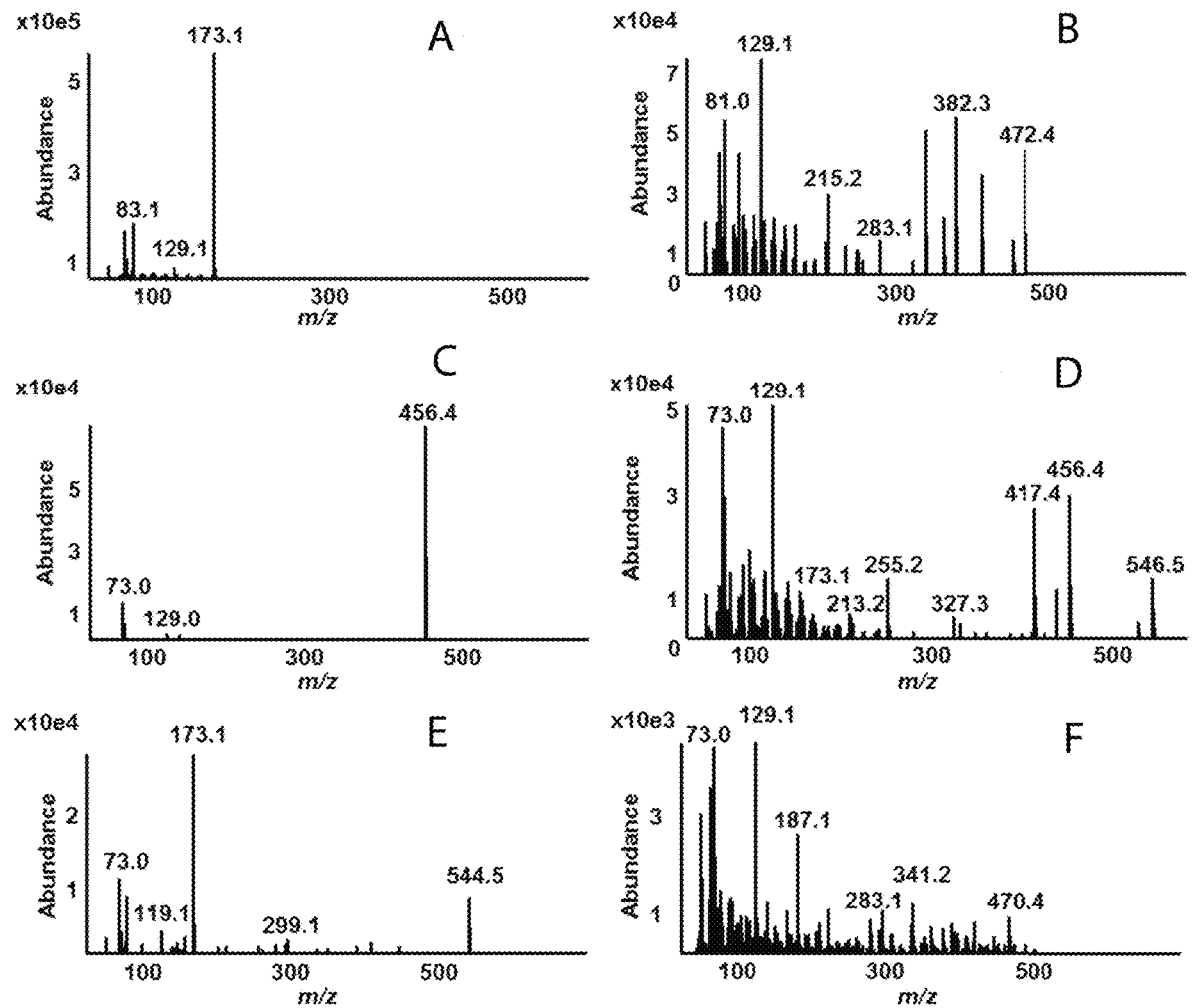
Figures 23A, 23B:
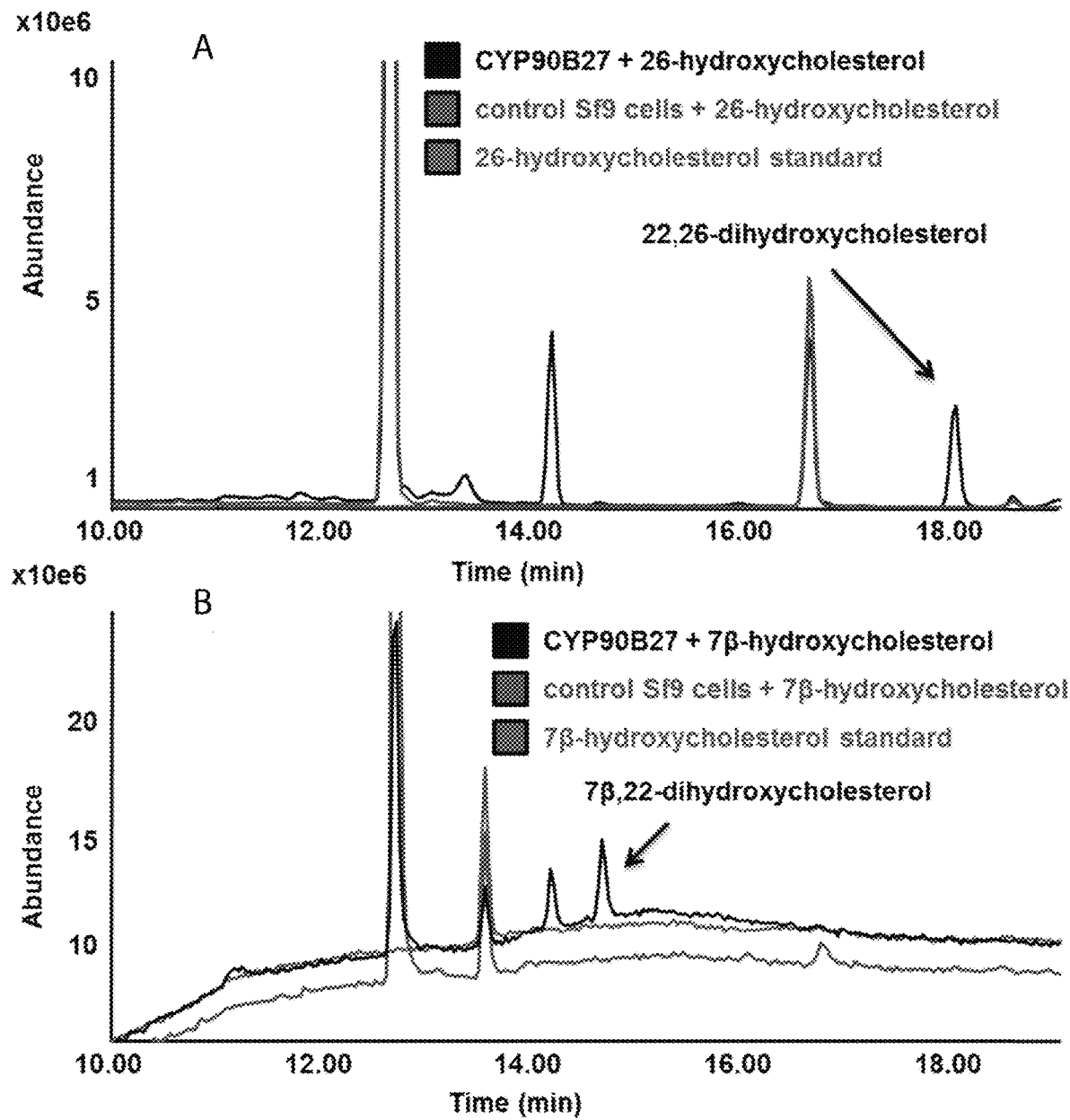
Figure 24:
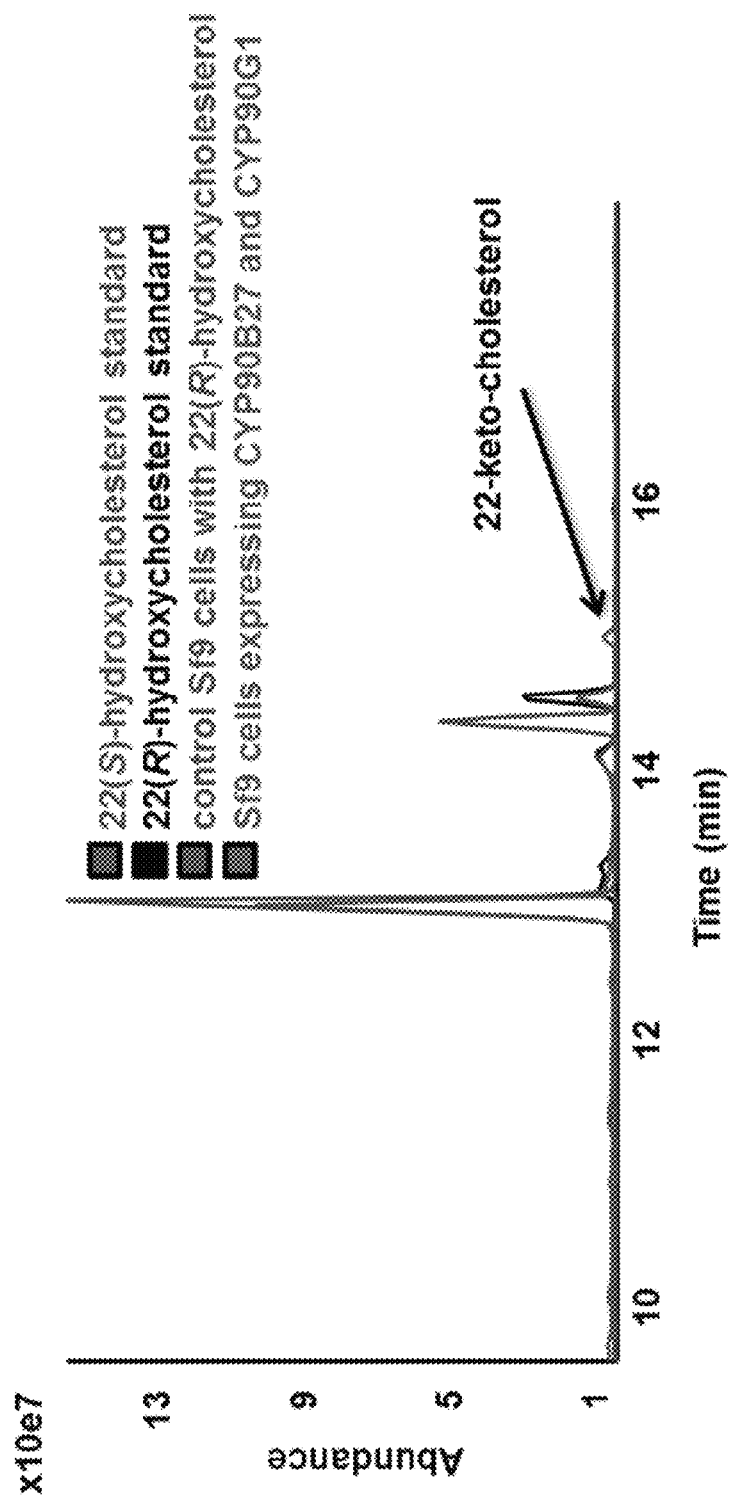
Figure 25:
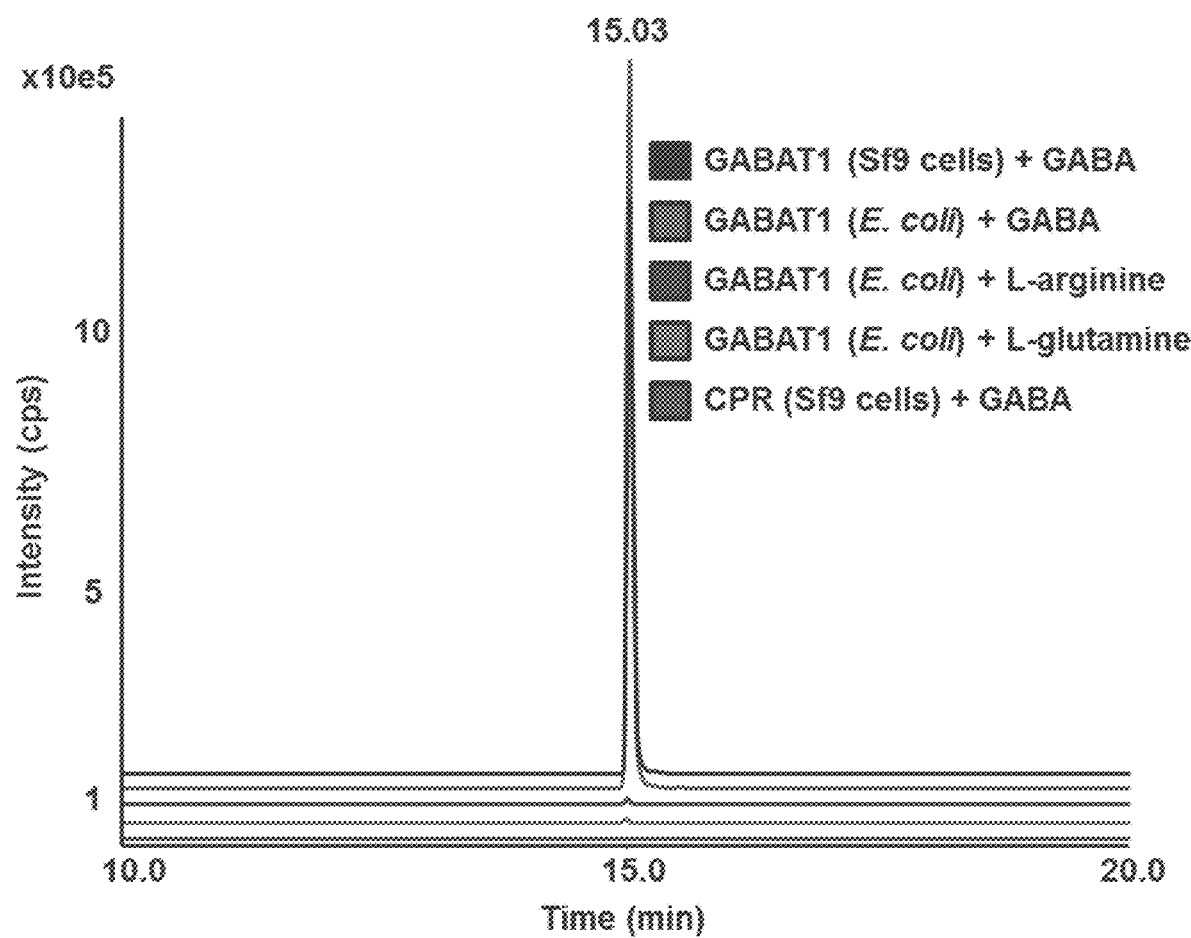

FIG. 21. Production of verazine by heterologous expression of *Veratrum californica* genes in *S. frugiperda* Sf9 cells. Select genes were introduced into *S. frugiperda* Sf9 cells using a baculovirus expression system. Metabolites were extracted and analyzed by LC-MS/MS in the full scan Enhanced MS mode detecting masses 380-425. Each colored chromatogram represent the combination of genes as follows: Green-Cholesterol 22-hydroxylase, 22-Hydroxycholesterol 26-hydroxylase/oxidase, 22-Hydroxy-26-aminocholesterol 22-oxidase, and CPR; Orange-Cholesterol 22-hydroxylase, 22-Hydroxycholesterol 26-hydroxylase/oxidase, 22-Hydroxy-26-aminocholesterol 22-oxidase, 22-Hydroxycholesterol-26-al transaminase, CPR; Pink-No enzyme control. CPR refers to the cytochrome P450 reductase from *Eschscholzia californica*. Peak at 398.4 is verazine, peak at 417.2 is 22-keto-26-hydroxycholesterol, and peak 418.4 is for 22-hydroxy-26-aminocholesterol.

FIGS. 22A-F. Mass spectra of select derivatized standards and enzymatically formed products. FIGS. 22A, 22B, 22C, 22D, 22E and 22F show enzyme assays using recombinant *Veratrum califomicum* genes and authentic standards were first extracted with hexane and derivatized with Sylon HTP before GC-MS analysis. (22A) Spectrum of 22(R)-hydroxycholesterol produced by enzyme assay using *S. frugiperda* Sf9 cells expressing CYP90B27 (cholesterol 22-hydroxylase) and *E. californica* cytochrome P450 reductase (CPR) with pure cholesterol as substrate. (22B) Spectrum of 22-keto-cholesterol produced by enzyme assay using Sf9 cells expressing CYP90G1 (22-hydroxy-26-aminocholesterol 22-oxidase) with pure 22(R)-hydroxycholesterol as substrate. (22C) Spectrum of pure 7β-hydroxycholesterol. (22D) Spectrum of pure 26-hydroxycholesterol. (22E) Spectrum of 7β,22-dihydroxycholesterol produced by enzyme assay using Sf9 cells expressing CYP90B27 and CPR with pure 7β-hydroxycholesterol as substrate. (22F) Spectrum of 22-keto-26-hydroxycholesterol produce by infection of Sf9 cells with CYP90B27, CYP90G1, CYP94N1 (22-hydroxycholesterol 26-hydroxylase/oxidase), and CPR. Mass spectra after background subtraction is shown.

FIGS. 23A, B. GC-MS analysis of *Veratrum californicum* CYP90B27 with 26-hydroxycholesterol and 7β-hydroxycholesterol. FIGS. 23A and 23B show enzyme assays using *S. frugiperda* Sf9 cells expressing CYP90B27 (cholesterol 22-hydroxylase) and *E. californica* cytochrome P450 reductase (CPR) were extracted and derivatized with Sylon HTP before GC-MS analysis. (23A) Enzyme assays using 26-hydroxycholesterol [27(25R)-hydroxycholesterol] as substrate. 26-Hydroxycholesterol [27(25R)-hydroxycholesterol] pure standard was included for reference. Control Sf9 cells expressing CYP719A14, cheilanthifoline synthase from *Argemone mexicana* (an unrelated cytochrome P450), and CPR, were run in parallel with 26-hydroxycholesterol [27(25R)-hydroxycholesterol] as a control. (23B) Enzyme assays with 7β-hydroxycholesterol as substrate. 7β-Hydroxycholesterol pure standard was included for reference and Sf9 cells expressing CYP719A14 and CPR were run in parallel with 7β-hydroxycholesterol as a control.

FIG. 24. GC-MS analysis of *Veratrum califomicum* cytochrome P450 enzymes CYP90B27 and CYP90G1. *S. frugiperda* Sf9 cells expressing enzyme CYP90B27 (cholesterol 22-hydroxylase), CYP90G1 (22-hydroxy-26-aminocholesterol 22-oxidase), and *E. californica* cytochrome P450 reductase (CPR) were extracted and derivatized with Sylon HTP before GC-MS analysis. 22(R)-Hydroxycholesterol and 22(S)-hydroxycholesterol pure standards were included for reference. Control cells expressing CYP719A14, cheilanthifoline synthase from *A. mexicana* (an unrelated cytochrome P450), and CPR were also assayed with 22(R)-hydroxycholesterol as a control.

FIG. 25. LC-MS/MS of enzyme assays with his-tag purified GABAT1. Recombinant GABAT1 from *Veratrum califomicum* was his-tag purified from *E. coli* PLUS E cells and used in enzyme assays with the substrate 22-hydroxycholesterol-26-al and GABA, L-arginine, or L-glutamine to determine the amino group donor. Sf9 cells infected with CPR were used as a negative control, and Sf9 cells infected with GABAT1 were used as a positive control. MRM signal 418/400 is presented for each assay. CPR refers to *E. californica* cytochrome P450 reductase. Each assay was performed in duplicate, with one representative chromatogram shown.

DESCRIPTION

The following detailed description is provided to aid those skilled in the art. Even so, the following detailed description should not be construed to unduly limit, as modifications and variations in the embodiments discussed herein may be made by those of ordinary skill in the art without departing from the spirit or scope of the present disclosure.

Any feature, or combination of features, described herein is (are) included within the scope of the present disclosure, provided that the features included in any such combination are not mutually inconsistent as will be apparent from the context, this specification, and the knowledge of one of ordinary skill in the art. Additional advantages and aspects of the present disclosure are apparent in the following detailed description and claims.

The contents of each of the publications, patent applications, patents, and other references mentioned herein are incorporated by reference in their entirety. In case of conflict, the present disclosure, including explanations of terms, will control.

I. Terms

The following definitions are provided to aid the reader in understanding the various aspects of the present disclosure. Unless defined otherwise, all technical and scientific terms used herein have the same meaning as commonly understood by those of ordinary skill in the art to which the disclosure pertains. Units, prefixes and symbols may be denoted in their SI accepted form. Provision, or lack of the provision, of a definition for a particular term or phrase is not meant to signify any particular importance, or lack thereof. Rather, and unless otherwise noted, terms used and the manufacture or laboratory procedures described herein are well known and commonly employed in the art. Conventional methods are used for these procedures, such as those provided in the art and various general references.

As used herein and in the appended claims, the singular forms "a", "an", and "the" include plural reference unless the context clearly dictates otherwise. Thus, for example, reference to "a plant" includes a plurality of such plants, reference to "a cell" includes one or more cells and equivalents thereof known to those skilled in the art, and so forth. Similarly, the word "or" is intended to include "and" unless the context clearly indicates otherwise. Hence "comprising A or B" means including A, or B, or A and B. Furthermore, the use of the term "including", as well as other related forms, such as "includes" and "included", is not limiting.

The term "comprising" as used in a claim herein is open-ended, and means that the claim must have all the features specifically recited therein, but that there is no bar on additional features that are not recited being present as well. The term "comprising" leaves the claim open for the inclusion of unspecified ingredients even in major amounts. The term "consisting essentially of" in a claim means that the invention necessarily includes the listed ingredients, and is open to unlisted ingredients that do not materially affect the basic and novel properties of the invention. A "consisting essentially of" claim occupies a middle ground between closed claims that are written in a closed "consisting of" format and fully open claims that are drafted in a "comprising' format". These terms can be used interchangeably herein if, and when, this may become necessary. Furthermore, the use of the term "including", as well as other related forms, such as "includes" and "included", is not limiting.

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as is known to one of ordinary skill in the art and is understood as included in embodiments where it would be appropriate. Nucleotides may be referred to by their commonly accepted single-letter codes. Unless otherwise indicated, amino acid sequences are written left to right in amino to carboxyl orientation, respectively. Amino acids may be referred to herein by either their commonly known three letter symbols or by the one-letter symbols recommended by the IUPAC-IUM Biochemical Nomenclature Commission. It is further to be understood that all base sizes or amino acid sizes, and all molecular weight or molecular mass values, given for nucleic acids or polypeptides are approximate, and are provided for description purposes and are not to be unduly limiting. Unless otherwise provided for, software, electrical, and electronics terms as used herein are as defined in The New IEEE Standard Dictionary of Electrical and Electronics Terms (5th edition, 1993). The terms defined below are more fully defined by reference to the specification as a whole.

If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.). Numeric ranges recited with the specification are inclusive of the numbers defining the range and include each integer within the defined range.

The term "about" as used herein is a flexible word with a meaning similar to "approximately" or "nearly". The term "about" indicates that exactitude is not claimed, but rather a contemplated variation. Thus, as used herein, the term "about" means within 1 or 2 standard deviations from the specifically recited value, or a range of up to 20%, up to 15%, up to 10%, up to 5%, or up to 4%, 3%, 2%, or 1% compared to the specifically recited value.

As used herein, "altering level of production" or "altering level of expression" means changing, either by increasing or decreasing, the level of production or expression of a nucleic acid sequence or an amino acid sequence (for example a polypeptide, an siRNA, a miRNA, an mRNA, a gene), as compared to a control level of production or expression.

The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and R. H. Schirmer (1979) Principles of Protein Structure, Springer-Verlag). According to such analyses, groups of amino acids can be defined where amino acids within a group exchange preferentially with each other, and therefore resemble each other most in their impact on the overall protein structure.

Examples of amino acid groups defined in this manner include: a "charged/polar group," consisting of Glu, Asp, Asn, Gln, Lys, Arg and His; an "aromatic, or cyclic group," consisting of Pro, Phe, Tyr and Trp; and an "aliphatic group" consisting of Gly, Ala, Val, Leu, Ile, Met, Ser, Thr and Cys. Within each group, subgroups can also be identified, for example, the group of charged/polar amino acids can be sub-divided into the sub-groups consisting of the "positively-charged sub-group," consisting of Lys, Arg and His; the negatively-charged sub-group," consisting of Glu and Asp, and the "polar sub-group" consisting of Asn and Gln. The aromatic or cyclic group can be sub-divided into the sub-groups consisting of the "nitrogen ring sub-group," consisting of Pro, His and Trp; and the "phenyl sub-group" consisting of Phe and Tyr. The aliphatic group can be sub-divided into the sub-groups consisting of the "large aliphatic non-polar sub-group," consisting of Val, Leu and Ile; the "aliphatic slightly-polar sub-group," consisting of Met, Ser, Thr and Cys; and the "small-residue sub-group," consisting of Gly and Ala. Examples of conservative mutations include substitutions of amino acids within the sub-groups above, for example, Lys for Arg and vice versa such that a positive charge can be maintained; Glu for Asp and vice versa such that a negative charge can be maintained; Ser for Thr such that a free —OH can be maintained; and Gln for Asn such that a free —NH₂ can be maintained.

As used herein "control" or "control level" means the level of a molecule, such as a polypeptide or nucleic acid, normally found in nature under a certain condition and/or in a specific genetic background. In certain embodiments, a control level of a molecule can be measured in a cell or specimen that has not been subjected, either directly or indirectly, to a treatment. A control level is also referred to as a wildtype or a basal level. These terms are understood by those of ordinary skill in the art. A control plant, i.e. a plant that does not contain a recombinant DNA that confers (for instance) an enhanced trait in a transgenic plant, is used as a baseline for comparison to identify an enhanced trait in the transgenic plant. A suitable control plant may be a non-transgenic plant of the parental line used to generate a transgenic plant. A control plant may in some cases be a transgenic plant line that comprises an empty vector or marker gene, but does not contain the recombinant DNA, or does not contain all of the recombinant DNAs in the test plant.

The terms "enhance", "enhanced", "increase", or "increased" refer to a statistically significant increase. For the avoidance of doubt, these terms generally refer to about a 5% increase in a given parameter or value, about a 10% increase, about a 15% increase, about a 20% increase, about a 25% increase, about a 30% increase, about a 35% increase, about a 40% increase, about a 45% increase, about a 50% increase, about a 55% increase, about a 60% increase, about a 65% increase, about 70% increase, about a 75% increase, about an 80% increase, about an 85% increase, about a 90% increase, about a 95% increase, about a 100% increase, or more over the control value. These terms also encompass ranges consisting of any lower indicated value to any higher indicated value, for example "from about 5% to about 50%", etc.

As used herein, "expression" or "expressing" refers to production of a functional product, such as, the generation of an RNA transcript from an introduced construct, an endogenous DNA sequence, or a stably incorporated heterologous DNA sequence. A nucleotide encoding sequence may comprise intervening sequence (e.g. introns) or may lack such intervening non-translated sequences (e.g. as in cDNA). Expressed genes include those that are transcribed into mRNA and then translated into protein and those that are transcribed into RNA but not translated (for example, siRNA, transfer RNA and ribosomal RNA). The term may also refer to a polypeptide produced from an mRNA generated from any of the above DNA precursors. Thus, expression of a nucleic acid fragment, such as a gene or a promoter region of a gene, may refer to transcription of the nucleic acid fragment (e.g., transcription resulting in mRNA or other functional RNA) and/or translation of RNA into a precursor or mature protein (polypeptide), or both.

An "expression cassette" refers to a nucleic acid construct, which when introduced into a host cell, results in transcription and/or translation of a RNA or polypeptide, respectively.

The term "genome" as it applies to a plant cells encompasses not only chromosomal DNA found within the nucleus, but organelle DNA found within subcellular components (e.g., mitochondrial, plastid) of the cell. As used herein, the term "genome" refers to the nuclear genome unless indicated otherwise. However, expression in a plastid genome, e.g., a chloroplast genome, or targeting to a plastid genome such as a chloroplast via the use of a plastid targeting sequence, is also encompassed by the present disclosure.

A polynucleotide sequence is "heterologous to" a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants. Heterologous nucleic acid fragments, such as coding sequences that have been inserted into a host organism, are not normally found in the genetic complement of the host organism. As used herein, the term "heterologous" also refers to a nucleic acid fragment derived from the same organism, but which is located in a different, e.g., non-native, location within the genome of this organism. Thus, the organism can have more than the usual number of copy(ies) of such nucleic acid fragment located in its(their) normal position within the genome and in addition, in the case of plant cells, within different genomes within a cell, for example in the nuclear genome and within a plastid or mitochondrial genome as well. A nucleic acid fragment that is heterologous with respect to an organism into which it has been inserted or transferred is sometimes referred to as a "transgene."

The term "homology" describes a mathematically based comparison of sequence similarities which is used to identify genes or proteins with similar functions or motifs. The nucleic acid and protein sequences of the present invention can be used as a "query sequence" to perform a search against public databases to, for example, identify other family members, related sequences or homologs. The term "homologous" refers to the relationship between two nucleic acid sequence and/or proteins that possess a "common evolutionary origin", including nucleic acids and/or proteins from superfamilies (e.g., the immunoglobulin superfamily) in the same species of animal, as well as homologous nucleic acids and/or proteins from different species of animal (for example, myosin light chain polypeptide, etc.; see Reeck et al., (1987) *Cell,* 50:667). Such proteins (and their encoding nucleic acids) may have sequence homology, as reflected by sequence similarity, whether in terms of percent identity or by the presence of specific residues or motifs and conserved positions. The methods disclosed herein contemplate the use of the presently disclosed nucleic and protein sequences, as well as sequences having sequence identity and/or similarity.

By "host cell" it is meant a cell which contains a vector and supports the replication and/or expression of the vector. Host cells may be prokaryotic cells such as *E. coli,* or eukaryotic cells such as yeast, insect, amphibian, or mammalian cells. Alternatively, the host cells are monocotyledonous or dicotyledonous plant cells.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. "Introduced" includes reference to stable or transient transformation methods, as well as sexually crossing. Thus, "introduced" in the context of inserting a nucleic acid fragment (e.g., a recombinant DNA construct/expression construct) into a cell, can mean "transfection" or "transformation" or "transduction", and includes reference to the incorporation of a nucleic acid fragment into a eukaryotic or prokaryotic cell where the nucleic acid fragment may be incorporated into the genome of the cell (e.g., chromosome, plasmid, plastid or mitochondrial DNA), converted into an autonomous replicon, or transiently expressed (e.g., transfected mRNA).

As used herein the term "isolated" refers to a material such as a nucleic acid molecule, polypeptide, or small molecule, such as cyclopamine, that has been separated from the environment from which it was obtained. It can also mean altered from the natural state. For example, a polynucleotide or a polypeptide naturally present in a living animal is not "isolated" but the same polynucleotide or polypeptide separated from the coexisting materials of its natural state is "isolated", as the term is employed herein. Thus, a polypeptide or polynucleotide produced and/or contained within a recombinant host cell is considered isolated. Also intended as "isolated polypeptides" or "isolated nucleic acid molecules", etc., are polypeptides or nucleic acid molecules that have been purified, partially or substantially, from a recombinant host cell or from a native source.

As used here "modulate" or "modulating" or "modulation" and the like are used interchangeably to denote either up-regulation or down-regulation of the expression or biosynthesis of a material such as a nucleic acid, protein or small molecule relative to its normal expression or biosynthetic level in a wild type or control organism. Modulation includes expression or biosynthesis that is increased or decreased by about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.1%, 99.5%, 99.9%, 100%, 110%, 115%, 120%, 125%, 130%, 135%, 140%, 145%, 150%, 155%, 160%, 165% or 170% or more relative to the wild type or control expression or biosynthesis level. As described herein, various material accumulation, such as that of cyclopamine, can be increased, or in the case of some embodiments, sometimes decreased relative to a control. One of ordinary skill will be able to identify or produce a relevant control.

As used herein, "nucleic acid" means a polynucleotide (or oligonucleotide), including single or double-stranded polymers of deoxyribonucleotide or ribonucleotide bases, and unless otherwise indicated, encompasses naturally occurring and synthetic nucleotide analogues having the essential nature of natural nucleotides in that they hybridize to complementary single-stranded nucleic acids in a manner similar to naturally occurring nucleotides. Nucleic acids may also include fragments and modified nucleotide sequences. Nucleic acids disclosed herein can either be naturally occurring, for example genomic nucleic acids; or isolated, purified, non-genomic nucleic acids, including synthetically produced nucleic acid sequences such as those made by chemical oligonucleotide synthesis, enzymatic synthesis, or by recombinant methods, including for example, cDNA, codon-optimized sequences for efficient expression in different transgenic plants reflecting the pattern of codon usage in such plants, nucleotide sequences that differ from the nucleotide sequences disclosed herein due to the degeneracy of the genetic code but that still encode the protein(s) of interest disclosed herein, nucleotide sequences encoding the presently disclosed protein(s) comprising conservative (or non-conservative) amino acid substitutions that do not adversely affect their normal activity, PCR-amplified nucleotide sequences, and other non-genomic forms of nucleotide sequences familiar to those of ordinary skill in the art.

As used herein, "nucleic acid construct" or "construct" refers to an isolated polynucleotide which can be introduced into a host cell. This construct may comprise any combination of deoxyribonucleotides, ribonucleotides, and/or modified nucleotides. This construct may comprise an expression cassette that can be introduced into and expressed in a host cell.

As used herein "operably linked" refers to a functional arrangement of elements. A first nucleic acid sequence is operably linked with a second nucleic acid sequence when the first nucleic acid sequence is placed in a functional relationship with the second nucleic acid sequence. For instance, a promoter is operably linked to a coding sequence if the promoter effects the transcription or expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence.

As used herein, the terms "plant" or "plants" that can be used in the present methods broadly include the classes of higher and lower plants amenable to transformation techniques, including angiosperms (monocotyledonous and dicotyledonous plants), gymnosperms, ferns, and unicellular and multicellular algae. The term "plant" also includes plants which have been modified by breeding, mutagenesis or genetic engineering (transgenic and non-transgenic plants). It includes plants of a variety of ploidy levels, including aneuploid, polyploid, diploid, haploid and hemizygous. The plant may be in any form including suspension cultures, embryos, meristematic regions, callus tissue, gametophytes, sporophytes, pollen, microspores, whole plants, shoot vegetative organs/structures (e.g. leaves, stems and tubers), roots, flowers and floral organs/structures, seed (including embryo, endosperm, and seed coat) and fruit, plant tissue (e.g. vascular tissue, ground tissue, and the like) and cells, and progeny of same. The term "food crop plant" includes plants that are either directly edible, or which produce edible products, and that are customarily used to feed humans either directly, or indirectly through animals. Non-limiting examples of such plants include: Cereal crops: wheat, rice, maize (corn), barley, oats, sorghum, rye, and millet; Protein crops: peanuts, chickpeas, lentils, kidney beans, soybeans, lima beans; Roots and tubers: potatoes, sweet potatoes, and cassavas; Oil crops: corn, soybeans, canola (rapeseed), wheat, peanuts, palm, coconuts, safflower, sesame, cottonseed, sunflower, flax, olive, and safflower; Sugar crops: sugar cane and sugar beets; Fruit crops: bananas, oranges, apples, pears, breadfruit, pineapples, and cherries; Vegetable crops and tubers: tomatoes, lettuce, carrots, melons, asparagus, etc.; Nuts: cashews, peanuts, walnuts, pistachio nuts, almonds; Forage and turf grasses; Forage legumes: alfalfa, clover; Drug crops: coffee, cocoa, kola nut, poppy, tobacco; Spice and flavoring crops: vanilla, sage, thyme, anise, saffron, menthol, peppermint, spearmint, coriander. The terms "biofuels crops", "energy crops", "oil crops", "oilseed crops", and the like, to which the present methods and compositions can also be applied include the oil crops and further include plants such as sugarcane, castor bean, *Camelina*, switchgrass, *Miscanthus*, and *Jatropha*, which are used, or are being investigated and/or developed, as sources of biofuels due to their significant oil production and accumulation.

The terms "peptide", "polypeptide", and "protein" are used to refer to polymers of amino acid residues. These terms are specifically intended to cover naturally occurring biomolecules, as well as those that are recombinantly or synthetically produced.

The term "promoter" or "regulatory element" refers to a region or nucleic acid sequence located upstream or downstream from the start of transcription and which is involved in recognition and binding of RNA polymerase and/or other proteins to initiate transcription of RNA. Promoters need not be of plant or algal origin, for example, promoters derived from plant viruses, such as the CaMV35S promoter, or from other organisms, can be used in variations of the embodiments discussed herein. Promoters useful in the present methods include constitutive, tissue-specific, cell-type specific, seed-specific, inducible, repressible, and developmentally regulated promoters.

A skilled person appreciates that a promoter sequence can be modified to provide for a range of expression levels of an operably linked heterologous nucleic acid molecule. Less than the entire promoter region can be utilized and the ability to drive expression retained. However, it is recognized that expression levels of mRNA can be decreased with deletions of portions of the promoter sequence. Thus, the promoter can be modified to be a weak or strong promoter. A promoter is classified as strong or weak according to its affinity for RNA polymerase (and/or sigma factor); this is related to how closely the promoter sequence resembles the ideal consensus sequence for the polymerase. Generally, by "weak promoter" is intended a promoter that drives expression of a coding sequence at a low level. By "low level" is intended levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts. The promoter of choice is preferably excised from its source by restriction enzymes, but can alternatively be PCR-amplified using primers that carry appropriate terminal restriction sites. It should be understood that the foregoing groups of promoters are non-limiting, and that one skilled in the art could employ other promoters that are not explicitly cited herein.

The term "purified" refers to material such as a nucleic acid, a protein, or a small molecule, such as cyclopamine, which is substantially or essentially free from components which normally accompany or interact with the material as found in its naturally occurring environment, and/or which may optionally comprise material not found within the purified material's natural environment. The latter may occur when the material of interest is expressed or synthesized in a non-native environment. Nucleic acids and proteins that have been isolated include nucleic acids and proteins purified by standard purification methods.

The term also embraces nucleic acids and proteins prepared by recombinant expression in a host cell as well as chemically synthesized nucleic acids. The present disclosure also encompasses methods and compositions comprising cyclopamine. In some embodiments, the cyclopamine is purified for therapeutic use and is formulated as a pharmaceutical composition. Such pharmaceutical compositions can be prepared by methods well known in the art. See, e.g., Remington: *The Science and Practice of Pharmacy*, 21$^{st}$ Edition (2005), Lippincott Williams & Wilkins, Philadelphia, Pa.

"Recombinant" refers to a nucleotide sequence, peptide, polypeptide, or protein, expression of which is engineered or manipulated using standard recombinant methodology. This term applies to both the methods and the resulting products. As used herein, a "recombinant construct", "expression construct", "chimeric construct", "construct" and "recombinant expression cassette" are used interchangeably herein.

As used herein, the phrase "sequence identity" or "sequence similarity" is the similarity between two (or more) nucleic acid sequences, or two (or more) amino acid sequences. Sequence identity is frequently measured as the percent of identical nucleotide or amino acid residues at corresponding positions in two or more sequences when the sequences are aligned to maximize sequence matching, i.e., taking into account gaps and insertions.

One of ordinary skill in the art will appreciate that sequence identity ranges are provided for guidance only. It is entirely possible that nucleic acid sequences that do not show a high degree of sequence identity can nevertheless encode amino acid sequences having similar functional activity. It is understood that changes in nucleic acid sequence can be made using the degeneracy of the genetic code to produce multiple nucleic acid molecules that all encode substantially the same protein. Means for making this adjustment are well-known to those of skill in the art. When percentage of sequence identity is used in reference to amino acid sequences it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

Sequence identity (or similarity) can be readily calculated by known methods, including but not limited to those described in: *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., *SIAM J Applied Math.*, 48: 1073 (1988). Methods to determine identity are designed to give the largest match between the sequences tested. Moreover, methods to determine identity are codified in publicly available computer programs. Optimal alignment of sequences for comparison can be conducted, for example, by the local homology algorithm of Smith & Waterman, by the homology alignment algorithms, by the search for similarity method or, by computerized implementations of these algorithms (GAP, BESTFIT, PASTA, and TFASTA in the GCG Wisconsin Package, available from Accelrys, Inc., San Diego, Calif., United States of America), or by visual inspection. See generally, (Altschul, S. F. et al., J. Mol. Biol. 215: 403-410 (1990) and Altschul et al. Nucl. Acids Res. 25: 3389-3402 (1997)).

One example of an algorithm that is suitable for determining percent sequence identity and sequence similarity is the BLAST® algorithm, which is described in (Altschul, S., et al., NCBI NLM NIH Bethesda, Md. 20894; & Altschul, S., et al., J. Mol. Biol. 215: 403-410 (1990). Software for performing BLAST® analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value, the cumulative score goes to zero or below due to the accumulation of one or more negative-scoring residue alignments, or the end of either sequence is reached. The BLAST® algorithm parameters W, T, and X determine the sensitivity and speed of the alignment. The BLASTN® program (for nucleotide sequences) uses as defaults a wordlength (W) of 11, an expectation (E) of 10, a cutoff of 100, M=5, N=−4, and a comparison of both strands. For amino acid sequences, the BLASTP® program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST®algorithm also performs a statistical analysis of the similarity between two sequences (see, e.g., Karlin & Altschul, Proc. Nat'l. Acad. Sci. USA 90: 5873-5877 (1993)). One measure of similarity provided by the BLAST® algorithm is the smallest sum probability (P (N)), which provides an indication of the probability by which a match between two nucleotide or amino acid sequences would occur by chance. BLAST® searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, Comput. Chem., 17: 149-163 (1993)) and XNU (Claverie and States, Comput. Chem., 17: 191-201 (1993)) low-complexity filters can be employed alone or in combination.

The constructs and methods disclosed herein encompass nucleic acid and protein sequences having sequence identity/sequence similarity at least about 75%, 80%, 85%, 90%, 95%, 96%, 97%, 98%, 99%, 100% to those specifically disclosed.

A "transgenic" organism, such as a transgenic plant, is a host organism that has been stably or transiently genetically engineered to contain one or more heterologous nucleic acid fragments, including nucleotide coding sequences, expression cassettes, vectors, etc. Introduction of heterologous nucleic acids into a host cell to create a transgenic cell is not limited to any particular mode of delivery, and includes, for example, microinjection, adsorption, electroporation, particle gun bombardment, whiskers-mediated transformation, liposome-mediated delivery, *Agrobacterium*-mediated transfer, the use of viral and retroviral vectors, etc., as is well known to those skilled in the art.

Conventional techniques of molecular biology, recombinant DNA technology, microbiology, chemistry useful in practicing the methods of the present disclosure are described, for example, in Green and Sambrook (2012) *Molecular Cloning: A Laboratory Manual*, Fourth Edition, Cold Spring Harbor Laboratory Press; Ausubel et al. (2003 and periodic supplements) *Current Protocols in Molecular Biology*, John Wiley & Sons, New York, N.Y.; Amberg et al. (2005) *Methods in Yeast Genetics: A Cold Spring Harbor Laboratory Course Manual*, 2005 Edition, Cold Spring Harbor Laboratory Press; Roe et al. (1996) *DNA Isolation and Sequencing: Essential Techniques*, John Wiley & Sons; J. M. Polak and James O'D. McGee (1990) *In Situ Hybridization: Principles and Practice*; Oxford University Press; M. J. Gait (Editor) (1984) *Oligonucleotide Synthesis: A Practical Approach*, IRL Press; D. M. J. Lilley and J. E. Dahlberg (1992) *Methods in Enzymology: DNA Structure Part A: Synthesis and Physical Analysis of DNA*, Academic Press; and *Lab Ref A Handbook of Recipes, Reagents, and Other Reference Tools for Use at the Bench*, Edited by Jane Roskams and Linda Rodgers (2002) Cold Spring Harbor Laboratory Press; Burgess and Deutscher (2009) *Guide to Protein Purification*, Second Edition (*Methods in Enzymology*, Vol. 463), Academic Press. Note also U.S. Pat. Nos. 8,178,339; 8,119,365; 8,043,842; 8,039,243; 7,303,906; 6,989,265; US20120219994A1; and EP1483367B1. The entire contents of each of these texts and patent documents are herein incorporated by reference.

II. Overview of the Several Embodiments

In one embodiment, the invention relates to a transgenic plant or a transgenic organism that produces cyclopamine and/or verazine-derived metabolite. The transgenic plant or the transgenic organism, comprising within its genome, and expressing, a heterologous nucleotide sequence coding for one or more cytochrome P450 enzyme(s) and/or a γ-aminobutyrate transaminase. In one embodiment, the transgenic plant or the transgenic organism, wherein said one or more cytochrome P450 enzyme(s) and/or said γ-aminobutyrate transaminase is selected from among SEQ ID NOs:1, 2, 3, 4, 5, 6, 7, 8, 9, 10, 11, 12, 13, 14, 15, 16, 17, 18, 19, 20, 21, 22, 23, 24, 25, or 26. In an embodiment the transgenic plant or the transgenic organism is selected from among a species of *Brachypodium*, a species of *Setaria*, a species of *Populus*, tobacco, corn, rice, soybean, cassava, canola (rapeseed), wheat, peanut, palm, coconut, safflower, sesame, cottonseed, sunflower, flax, olive, safflower, sugarcane, castor bean, switchgrass, *Miscanthus*, *Camelina* and *Jatropha*. In another embodiment the transgenic plant or the transgenic organism, wherein said heterologous nucleotide sequence is codon-optimized for expression in said transgenic plant. In yet another embodiment, the transgenic plant or the transgenic organism, wherein said heterologous nucleotide sequence is expressed in a tissue or organ selected from among an inflorescence, a flower, a sepal, a petal, a pistil, a stigma, a style, an ovary, an ovule, an embryo, a receptacle, a seed, a fruit, a stamen, a filament, an anther, a male or female gametophyte, a pollen grain, a meristem, a terminal bud, an axillary bud, a leaf, a stem, a root, a tuberous root, a rhizome, a tuber, a stolon, a corm, a bulb, an offset, a cell of said plant in culture, a tissue of said plant in culture, an organ of said plant in culture, and a callus.

In another embodiment, the invention relates to a method of making the transgenic plant or the transgenic organism, comprising the steps of: (i) inserting into the genome of a plant cell or an organism cell a heterologous nucleotide sequence comprising, operably linked for expression: (a) a promoter sequence; (b) at least one heterologous nucleotide sequence coding for a cytochrome P450 enzyme, and/or a γ-aminobutyrate transaminase; (ii) obtaining a transformed plant cell or a transformed organism cell; and (iii) regenerating from said transformed plant cell or said transformed organism cell a genetically transformed plant or a genetically transformed organism, wherein said genetically transformed plant or said genetically transformed organism produces cyclopamine and/or verazine-derived metabolite. In another embodiment the invention relates to a transgenic plant or a transformed organism made by the method.

In a further embodiment, the invention relates to a method of obtaining or producing cyclopamine and/or verazine-derived metabolite, comprising recovering cyclopamine from a transgenic plant or a transgenic organism. In yet another embodiment the invention contemplates cyclopamine and/or verazine-derived metabolite made by the method. In yet another embodiment, the invention relates to a method of preparing a cyclopamine and/or verazine-derived metabolite containing pharmaceutical composition, comprising formulating cylcopamine and/or verazine-derived metabolite as a pharmaceutical composition comprising a pharmaceutically acceptable carrier, dilient, or excipient, wherein said cyclopamine and/or verazine-derived metabolite is recovered from a transgenic plant. In a further embodiment, the pharmaceutical composition, wherein said transgenic plant or said transgenic organism is made by the method.

In another embodiment, the invention relates to a pharmaceutical composition comprising cyclopamine and/or verazine-derived metabolite, wherein said cylcopamine and/or verazine-derived metabolite is obtained by growing a plant or an organism, and recovering cyclopamine and/or verazine-derived metabolite from said plant or said organism. Cyclopamine and/or verazine-derived metabolite for use in human therapy, wherein said cyclopamine and/or verazine-derived metabolite is recovered from a transgenic plant or an organism; and/or wherein said transgenic plant or transgenic organism is made by the method; and/or wherein said cyclopamine and/or verazine-derived metabolite is produced by the method. Use of cyclopamine and/or verazine-derived metabolite in human and/or animal therapy, wherein said cyclopamine and/or verazine-derived metabolite is recovered from a transgenic plant or a transgenic organism; and/or wherein said transgenic plant or said transgenic organism is made by the method; and/or wherein said cyclopamine and/or verazine-derived metabolite is produced by the method. Use of cyclopamine and/or verazine-derived metabolite for the preparation of a medicament for the treatment of cancer, wherein said cyclopamine and/or verazine-derived metabolite is recovered from a transgenic plant or a transgenic organism; and/or wherein said transgenic plant is made by the method; and/or wherein said cyclopamine and/or verazine-derived metabolite is produced by the method.

III. Biochemical Pathway Elucidation

The chemical diversity of plant natural products has provided humans with a variety of intriguing structures and biological activities. Due to these biological activities, 25% of medicines today are either derived directly from plants or are structural modifications of plant natural products. An understanding of how these molecules are formed would serve a dual role to enable a study of the in planta function, as well as development of a synthetic biology production platform.

Natural products typically do not accumulate to high levels in the plant. If the source plant for a novel drug is not amenable to cultivation, drug development can be precluded. Engineering of a natural product biosynthetic pathway into an easily cultivated host plant can result in a sustainable supply of a drug. The first obstacle to this approach, however, is knowledge of the underlying biosynthetic genes.

Absent knowledge concerning the underlying genes or enzymes involved in a biosynthetic pathway, the candidate gene selection process requires extensive enzymatic and bioinformatic analysis concerning protein prediction, annotation, and phylogenetic relationships. Initial transcriptome sequencing of different *Veratrum californicum* tissue cDNAs led to an extensive list of more than 56,000 expressed genes, none of which had been previously characterized. Moreover, many of the intermediates and metabolites are transitory and structurally unusual and/or complex; requiring multiple qualitative and quantitative detection methods, which add additional levels of difficulty to identification of genes within the biosynthetic pathway. In addition, further complicating biosynthetic pathway analysis, several of the enzymes identified herein do not exhibit single-substrate specificity, i.e., one enzyme may catalyze multiple reactions. Thus, the inventors performed detailed analyses to distinguish metabolites of interest from intermediates and/or side products to elucidate the order and steps involved in the biosynthesis of cyclopamine.

Elucidation of biochemical pathways is of importance to understanding an organism on the molecular level. From a biotechnological perspective, knowledge of underlying genes of enzymes involved in biochemical synthesis is also required for suppressing, modifying, or even refactoring entire pathways on a synthetic biology platform. Protein purification and mining of cDNA libraries often required decades to elucidate complete pathways.

Biochemical pathway elucidation in non-model systems has often taken decades to complete. A prominent example is the well-known plant natural product morphine produced by the opium poppy *Papaver somniferum*. Though discovered in the early 1800's, the biosynthetic pathway is still not completely elucidated at the gene level. Much of the enzyme discovery work was accomplished by antibody screening, protein purification, amino acid sequencing, and subsequent cloning based upon those sequences. Genes encoding only 6 of the 8 enzymes committed to the biosynthesis of morphine have been isolated and characterized from the 1990's to the present, i.e., several decades of work to uncover fewer than 8 genes.

Next-gen sequencing technology enables revolutionary new approaches to biochemical pathway discovery in the non-model system. Nucleotide sequence data acquisition is achieved at a previously unparalleled rate; however, bioinformatic interrogation of these large data sets remains a challenge. A combination of bioinformatics and next-gen sequencing has the potential to shorten natural product pathway discovery in non-model systems from several decades to several years. Methods employing next-gen sequencing technology are currently being tested in this respect.

Presented herein is a broadly applicable biosynthetic gene discovery method that is based on correlating plant metabolite accumulation with RNAseq gene expression data. As proof-of-concept of this method, the biosynthetic pathway to the complex steroid alkaloid cyclopamine was chosen.

To identify genes in this pathway, the inventors interrogated a *V. californicum* RNAseq dataset using a cyclopamine accumulation profile as the predefined model for gene expression with the pattern-matching algorithm Haystack. The inventors have identified and refactored in *Spodoptera frugiperda* Sf9 cells four *V. californicum* enzymes that catalyze the first six steps from cholesterol in the biosynthesis of the steroid alkaloid cyclopamine. The pathway refactoring method developed eliminates the need to synthesize and purify biosynthetic intermediates for validation of pathway enzyme activity.

Three of the newly discovered enzymes, i.e., cholesterol 22-hydroxylase, 22-hydroxycholesterol 26-hydroxylase/oxidase, and 22-hydroxy-26-aminocholesterol 22-oxidase, are cytochromes P450. The fourth enzyme is a γ-aminobutyrate transaminase that catalyzes the transfer of nitrogen to 22-hydroxycholesterol-26-al. Enzymatic activity was confirmed by refactoring the plant pathway in *Spodoptera frugiperda* Sf9 cells. Structure elucidation of the enzymatic products was achieved by GC-MS, LC-MS/MS and NMR spectroscopy.

IV. Examples

The following examples are provided to illustrate various aspects of the present disclosure, and should not be construed as limiting the disclosure only to these particularly disclosed embodiments.

The materials and methods employed in the examples below are for illustrative purposes only, and are not intended to limit the practice of the present embodiments thereto.

Any materials and methods similar or equivalent to those described herein as would be apparent to one of ordinary skill in the art can be used in the practice or testing of the present embodiments.

Example 1

RNA extraction

*V. californicum* plant material was obtained from wild populations in northern Utah. Tissue culture was initiated from wild collected seed and grown in the dark at 24° C. on a combination of Linsmaier and Skoog vitamins and Murashige and Skoog media supplemented with 0.5 mg/l 1-naphthaleneacetic acid (Sigma). Refer to Table 1 for full media components. RNA extraction for each tissue (bulb, flower, leaf, fall rhizome, spring rhizome, root, green shoot, white shoot, and tissue culture samples) was performed as previously described (protocol 13). RNA quantity and integrity were evaluated with a NanoDrop 2000 (Thermo Scientific) and a Bioanalyzer 2100 (Agilent Technologies) prior to cDNA library preparation.

TABLE 1

LS/MS Rooting Media. LS/MS media was prepared with the following concentrations and brought to a final pH of 5.75.

|  | Supplier | Final Concentration (mg/l) |
|---|---|---|
| Macronutrients |  |  |
| $NH_4NO_3$ | Phytotechnology laboratories | 1650 |
| $KNO_3$ | Sigma | 1900 |
| $MgSO_4 \times 7H_2O$ | Sigma | 370 |
| $KH_2PO_4$ | Sigma | 170 |
| $CaCl_2 \times 2H_2O$ | Sigma | 440 |
| Iron |  |  |
| $Na_2EDTA \times 2H_2O$ | Sigma | 37.3 |
| $FeSO_4 \times 7H_2O$ | Sigma | 27.8 |
| Micronutrients |  |  |
| $H_3BO_3$ | Sigma | 6.2 |
| $MnSO_4 \times H_2O$ | Phytotechnology laboratories | 16.9 |
| $ZnSO_4 \times 7H_2O$ | Sigma | 8.6 |
| KI | Sigma | 0.83 |
| $Na_2MoO_4 \times 2H_2O$ | Phytotechnology laboratories | 0.25 |
| $CuSO_4 \times 5H_2O$ | Sigma | 0.025 |
| $CoCl_2 \times 6H_2O$ | Sigma | 0.025 |
| Vitamines |  |  |
| Thiamine HCl | Sigma | 0.1 |
| Nicotinic Acid | Sigma | 0.5 |
| Pyroxidine HCl | Sigma | 0.5 |
| myo-inositol | Sigma | 100 |
| Other |  |  |
| Sucrose | Phytotechnology laboratories | 30000 |
| 1-naphthaleneacetic acid | Phytotechnology laboratories | 0.5 |
| Gelzan | Phytotechnology laboratories | 3000 |

Liquid Chromatography Mass Spectrometry (LC-MS/MS) Method

Liquid chromatographic separation was achieved with 10 μl injections on a LC-20AD (Shimadzu) LC system coupled to a 4000 QTRAP (AB Sciex Instruments) for MS/MS analysis. Separation was achieved using a Phenomenex Gemini C-18 NX column (150×2.00 mm, 5 μm) with a flow rate of 0.5 ml/min and the following gradient program [solvent A (0.05% formic acid/0.04% ammonium hydroxide (25%) v/v in $H_2O$; solvent B (0.05% formic acid/0.04% ammonium hydroxide (25%) v/v in 90% acetonitrile]: Solvent B was held at 20% for 2 min, then 2-11 min 20-30% B, 11-18 min 30-100% B, 18-22 min 100% B, 22-23 min 100-20% B, and held at 20% B for an additional 5 minutes. Program parameters included a TurbolonSpray ionization source temperature of 500° C. and low resolution for Q1 and Q3 done with MRM (Multiple Reaction Monitoring) scans in the positive ion mode. Specific ion fragments and parameters can be found in Table 2. In conjunction, EMS (Enhanced MS) scan with a mass range of 380 to 425 m/z, and EPI (Enhanced Product Ion) scans for 398, 417, and 418 m/z were included in the method. Compound identification was determined by comparison of retention time and fragmentation pattern to the authentic standard cyclopamine (where applicable). Quantitation was performed by plotting peak area versus pmol of standard using Analyst 1.5 (Applied Biosystems).

TABLE 2

Q-TRAP 4000 Method Parameters

|  | Q1 Mass | Q3 Mass | Dwell (msec) | DP | CE |
|---|---|---|---|---|---|
| Veratramine | 410 | 392 | 100 | 120 | 40 |
|  | 410 | 295 | 100 | 120 | 40 |
| Cyclopamine | 412 | 321 | 100 | 120 | 40 |
|  | 412 | 394 | 100 | 120 | 40 |
| Muldamine | 458 | 398 | 100 | 100 | 47 |
|  | 458 | 253 | 100 | 100 | 47 |
| 22-Keto 26-hydroxycholesterol | 417 | 271 | 100 | 70 | 30 |
|  | 417 | 253 | 100 | 70 | 30 |
| 22-hydroxy-26-amino-cholesterol | 418 | 400 | 100 | 70 | 30 |
|  | 418 | 382 | 100 | 70 | 30 |
| Verazine | 398 | 253 | 100 | 70 | 60 |
|  | 398 | 159 | 100 | 70 | 60 |

Gas Chromatography Mass Spectrometry (GC-MS) Method

Samples were first extracted with either hexane:isopropanol 3:2 followed by hexane only or ethyl acetate. Dried extracts were derivatized with 40 µl Sylon HTP (Sigma) for 1 hour at 90° C. prior to injection with a 7683B autosampler onto a 7890A gas chromatograph coupled to a 5975C mass spectrometer inert XL MSD with triple-axis detector (Agilent Technologies). Both full scan and SIM methods were run in the splitless mode with 1 µl injection volume and a flow rate of 1 ml/min with helium as the carrier gas. Separation was performed on a Zebron ZB-5MSi column with guardian 5M (30 m×0.25 mm×0.25 µm) with 5% Polysilarylene –95% Polydimethylsiloxane copolymer composition and 106 relative voltage. The initial temperature of 240° C. was held for 5 minutes and increased to 300° C. at a rate of 10° C./min and held for 25 minutes. The full scan method measured mass from 50 to 800 amu and ions detected in the SIM mode included: 99.1, 129, 165, 171, 173.1, 187, 261, 314.1, 329.3, 330, 370, 382.3, 417.4, 456.4, 458, 460, 470, 472.3, 486, 546, 560, and 634.

Metabolite Extraction and Quantitation by LC-MS/MS

Quantitation of cyclopamine in extracts from *V. californicum* was performed by LC-MS/MS. Extracts were prepared by grinding frozen plant tissue in liquid nitrogen followed by 5 minutes of vortexing in 70% ethanol added in a 200 µl to 100 mg w/v ratio. Samples were subject to centrifugation for 10 minutes (14,000×g) at room temperature and the supernatant filtered through a 0.2 µm PTFE membrane (Millipore) prior to injection. Extracts were diluted 10-10,000 fold with 70% ethanol, depending on alkaloid content, prior to LC-MS/MS analysis (see LC-MS/MS method above).

Transcriptome Assembly and Retrieval of Expression Data cDNA library construction, Illumina paired-end sequencing, and de novo transcriptome assembly were performed at the National Center for Genome Resources (Santa Fe, N. Mex.). For the transcriptome assembly, 54 bp paired-end Illumina reads for each tissue were first examined for gross abnormalities and poor sequence quality and trimmed with the FASTX Toolkit. Subsequently short contig assembly was performed using the de Bruijn graph-based assembler ABySS several times with varying kmer lengths to generate 20 sets of synthetic ESTs with lengths between 100-500 base pairs. ABySS scaffolder was used to scaffold the synthetic ESTs and GapCloser from SOAPdenovo to close the NNN gap spacers. Lastly, the assembly was completed by combining the obtained scaffolds using Mira in the EST assembly mode. Post processing included translational predictions for each contig using ESTSCAN and determination of expression data by alignment analysis of the trimmed reads to the assembled contigs using BWA.

To further enable comparison of gene expression between various tissues, the number of reads aligned to each contig was normalized by dividing by the total number of reads from the respective tissue sample. Functional annotations to each predicted protein sequence were obtained using Pfam, Superfamily, and Uniprot.

Haystack Modeling

Identification of genes whose expression pattern correlated with accumulation of cyclopamine was determined using the Haystack program. The LC-MS/MS cyclopamine quantitation data for the different *V. californicum* tissues was used to formulate a model based upon the ratio of biosynthetic tissues. 95% of the total cyclopamine was found in the subterranean tissues (root, bulb, and rhizome) whereas 5% was found above ground (leaf, stem, and flower). For the input model, each subterranean tissue was given a value of 20 and all above ground tissues including the tissue culture samples was designated 1. Parameters for Haystack were as follows: correlation cut off=0.7 fold change=2, p-value=0.05 and background=1. Due to the large data input, Haystack analysis was performed on a UNIX server in-house as opposed to the version available online. Annotation data was then merged with the gene outputs from each of the models. Subsequent alignments and phylogenetic analysis were performed using Muscle algorithm and Mega v6.06.

Construction of Viral Expression Vectors

Candidate contigs obtained from Haystack analysis were subjected to BLAST® searches and global alignments to homologous, experimentally characterized gene sequences with the CLC Main Workbench 6.8, for prediction of the open reading frame. Where the reading frame appeared incomplete, Rapid Amplification of cDNA Ends (RACE) was used to obtain the complete coding sequence. *V. californicum* cDNA was prepared from root RNA extracts using M-MLV Reverse Transcriptase (Invitrogen) according to manufacturer's instructions. All primer sequences and PCR programs can be found in the Sequence Listing (SEQ ID NO:27-48) and Table 3, respectively.

TABLE 3

PCR Parameters

| | |
|---|---|
| VC2646 for TOPO cloning, VC2646 for pVL1392 cloning, VC12709 for pVL1392 cloning, VC13284 TOPO cloning | 98° C. for 30 sec, then 35 cycles of 98° C. for 10 sec, 60° C. for 30 sec, 72° C. for 1 min 30 sec, and a final 10 min extension at 72° C. |
| VC12709 5' RACE | 98° C. for 30 sec, then 35 cycles of 98° C. for 10 sec, 65° C. for 30 sec, 72° C. for 1 min and a final 10 min extension at 72° C. |
| VC13284 for pVL1392 cloning | 98° C. for 30 sec, then 35 cycles of 98° C. for 10 sec, 63° C. for 30 sec, 72° C. for 1 min 25 sec, and a final 10 min extension at 72° C. |

TABLE 3-continued

| PCR Parameters | |
| --- | --- |
| VC12084 for pVL1392 cloning | 98° C. for 30 sec, then 35 cycles of 98° C. for 10 sec, 60° C. for 30 sec, 72° C. for 1 min, and a final 10 min extension at 72° C. |
| Tomato GABAT and VC674 for pVL1392 cloning | 98° C. for 30 sec, then 35 cycles of 98° C. for 10 sec, 62° C. for 30 sec, 72° C. for 45 sec, and a final 10 min extension at 72° C. |
| Semi-Quantitative RT-PCR | 95° C. for 2 min, then 26 cycles of 95° C. for 30 sec, 50° C. for 30 sec, 72° C. for 15 sec |

The cDNAs encoding cholesterol 22-hydroxylase (accession numbers KJ869252, KJ869253), 22-hydroxy-26-aminocholesterol 22-oxidase (accession numbers KJ869258-KJ869261), 22-hydroxycholesterol-26-al transaminase (accession numbers KJ869262-KJ869264) and γ-aminobutyrate (GABA) transaminase 2 (accession number KJ869265) were determined to b efull length. Cholesterol 22-hydroxylase and 22-hydroxy-26-aminocholesterol 22-oxidase were amplified by Polymerase Chain Reaction (PCR) from cDNA with Phusion DNA polymerase (New England Biolabs) using primers 1-4 and 7-8, respectively, and initially ligated into the pCR-Blunt I-TOPO vector (Invitrogen). Two rounds of amplification were required for cholesterol 22-hydroxylase by nested PCR. Subsequently, cholesterol 22-hydroxylase was amplified from pCR-Blunt II-TOPO with primersS5 and 6 introducing NotI/BamHI restriction sites into the PCR products at the 5' and 3' ends of the open reading frame. The amplified product and pVL1392 Baculovirus transfer vector (BD Biosciences) were digested with NotI/BamHI and ligated together using Rapid Ligase (Promega). Ligated constructs were transformed into E. coli DH5a competent cells. 22-Hydroxy-26-aminocholesterol 22-oxidase was amplified with primers 9 and 10, introducing PstI/XbaI restriction sites at the 5' and 3' end of the open reading frame. The amplified product, along with pVL1392, was digested with PstI/XbaI and subject to ligation and transformation.

22-Hydroxycholesterol-26-al transaminase and GABA transaminase 2 were directly amplified from cDNA using primers 11, 12 incorporating BglII/EcoRI restriction sites at the 5' and 3' end of the open reading frame and 21, 22, incorporating PstI/XbaI restriction sites at the 5' and 3' end of the open reading frame, respectively. 22-Hydroxycholesterol-26-al transaminase and pVL1392 were subject to restriction digest with BglI/EcoRI preceding ligation and transformation. GABA transaminase 2 was digested with XbaI/PstI, preceding ligation and transformation.

RACE was required to determine the 5' sequence of 22-hydroxycholesterol 26-hydroxylase/oxidase gene (accession numbers KJ869254-KJ869257). RACE ready cDNA was prepared using the GeneRacer Kit (Invitrogen) according to manufacturer's instructions using V. californicum root RNA. Primers 13 and 15 were used for PCR (round 1), followed by amplification using primers 14 and 16 (round 2). Resulting RACE fragments were cloned into PCR-Blunt II-TOPO. The full-length gene was directly amplified from V. californicum root cDNA with primers 17 and 18, incorporating BglII/EcoRI restriction sites at the 5' and 3' end of the open reading frame. The amplified product was digested with BglII/EcoRI and ligated into pVL1392 digested with the same enzymes. Each characterized V. californicum contig and subsequent enzyme designation can be found in Table 4.

TABLE 4

Enzyme assignments

| Transcriptome derived Contig designations | CYP designation | Accession numbers | Assigned name based on function |
| --- | --- | --- | --- |
| >medp_verca-20110208\|2646 | CYP90B27v1 | KJ869252 | Cholesterol 22-hydroxylase |
| | CYP90B27v2 | KJ869253 | Cholesterol 22-hydroxylase |
| >medp_verca-20110208\|12709 | CYP94N1v1 | KJ869254 | 22-Hydroxycholesterol 26-hydroxylase/oxidase |
| | CYP94N1v2 | KJ869255 | 22-Hydroxycholesterol 26-hydroxylase/oxidase |
| | CYP94N2v1 | KJ869256 | 22-Hydroxycholesterol 26-hydroxylase/oxidase |
| | CYP94N2v2 | KJ869257 | 22-Hydroxycholesterol 26-hydroxylase/oxidase |
| >medp_verca-20110208\|12084 | N/A | KJ869262 | 22-Hydroxycholesterol-26-al transaminase |
| | N/A | KJ869263 | 22-Hydroxycholesterol-26-al transaminase |
| | N/A | KJ869264 | 22-Hydroxycholesterol-26-al transaminase |
| >medp_verca-20110208\|13284 | CYP90G1v1 | KJ869258 | 22-Hydroxy-26-aminocholesterol 22-oxidase |
| | CYP90G1v2 | KJ869261 | 22-Hydroxy-26-aminocholesterol 22-oxidase |
| | CYP90G1v3 | KJ869260 | 22-Hydroxy-26-aminocholesterol 22-oxidase |
| | CYP90G2 | KJ869259 | 22-Hydroxy-26-aminocholesterol 22-oxidase |

The cDNA encoding GABA transaminase isozyme 2 from Solanum lycopersicum (tomato) implicated in steroid alkaloid biosynthesis (accession number AY240230) was isolated from S. lycopersicum using the Qiagen RNA-easy kit for RNA extraction followed by cDNA synthesis as described above. S. lycopersicum GABA transaminase isozyme 2 was amplified by PCR using Primers 19 and 20, incorporating PstI/XbaI sites at the 5' and 3' end of the open reading frame. The amplified product and pVL1392 were subject to restriction digest with PstI/XbaI and ligated together, preceding transformation.

Virus Co-Transfection, Amplification, and Protein Production

Each pVL1392 expression construct was independently co-transfected with the Baculogold Linearized Baculovirus (BD Biosciences) into S. frugiperda Sf9 cells according to manufacturer's instructions. Sf9 cells were maintained as previously described. Virus amplification and protein production proceeded as previously described. Each cytochrome P450 virus construct was co-expressed with Eschscholzia californica cytochrome P450 reductase (CPR) in S. frugiperda Sf9 cells. S. frugiperda Sf9 cell cultures were also infected with several constructs in parallel. Combinations of each cytochrome P450 can be found in Table 5. In addition, V californicum 22-hydroxycholesterol-26-al transaminase was produced by single infection. Equal volumes for each virus were used in the multiple infections and adjusted to a total viral volume of 2.5 ml.

TABLE 5

Viral combination for in vivo production of metabolites in Sf9 cells

| Combination | Viruses |
|---|---|
| Combination 1 | Cholesterol 22-hydroxylase, CPR |
| Combination 2 | 22-Hydroxycholesterol 26-hydroxylase/oxidase, CPR |
| Combination 3 | 22-Hydroxy-26-aminocholesterol 22-oxidase, CPR |
| Combination 4 | Cholesterol 22-hydroxylase, 22-Hydroxycholesterol 26-hydroxylase/oxidase, CPR |
| Combination 5 | Cholesterol 22-hydroxylase, 22-Hydroxy-26-aminocholesterol 22-oxidase, CPR |
| Combination 6 | Cholesterol 22-hydroxylase, 22-Hydroxycholesterol 26-hydroxylase/oxidase, 22-Hydroxy-26-aminocholesterol 22-oxidase, CPR |
| Combination 7 | Cholesterol 22-hydroxylase, 22-Hydroxycholesterol 26-hydroxylase/oxidase, 22-Hydroxy-26-aminocholesterol 22-oxidase, 22-Hydroxycholesterol-26-al transaminase, CPR |
| Combination 8 | Cholesterol 22-hydroxylase, 22-Hydroxycholesterol 26-hydroxylase/oxidase, 22-Hydroxy-26-aminocholesterol 22-oxidase, γ-aminobutyrate transaminase 2, CPR |
| Combination 9 | Cholesterol 22-hydroxylase, 22-Hydroxycholesterol 26-hydroxylase/oxidase, 22-Hydroxy-26-aminocholesterol 22-oxidase, S. lycopersicum GABA transaminase isozyme 2, CPR |
| Combination 10 | Cholesterol 22-hydroxylase, 22-Hydroxycholesterol 26-hydroxylase/oxidase, 22-Hydroxycholesterol-26-al transaminase, CPR |

Extraction of Multiple Infections for Sf9 In Vivo Product Production

Baculovirus infections were carried out and insect cells were collected as stated above and used for production of each enzymatic product in S. frugiperda Sf9 cells. 1 ml each of S. frugiperda Sf9 cells expressing the various combinations of virus were extracted with 2 volumes of ethyl acetate by vortexing (1 min), centrifugation (16,000×g; 2 min), and were taken to dryness under $N_2$. Samples were either derivatized with 40 µl of Sylon HTP and injected onto the GC-MS with the method stated above or re-suspended in 50 µl of 80% Methanol and analyzed by LC/MS-MS with the method stated above.

Enzyme Assays

Each cytochrome P450 co-expressed with CPR in S. frugiperda Sf9 cells was subjected to individual enzyme assays with the compounds found in Table 6 to determine functionality. Compounds were prepared to 1 mM stock solutions of 100% DMSO and diluted with $H_2O$.

TABLE 6

Substrate testing for cytochrome P450 enzymes co-expressed with CPR.

| | CYP90B27 | CYP90G1 | CYP94N1 |
|---|---|---|---|
| cholesterol | + | − | − |
| 22(R)-hydroxycholesterol | + | + | + |
| 22(S)-hydroxycholesterol | − | − | − |
| 26-hydroxycholesterol | + | − | N/A |
| 22,26-dihydroxycholesterol | N/A | + | N/A |
| 22-keto-cholesterol | N/A | N/A | − |
| 4β-hydroxycholesterol | − | − | − |
| 7β-hydroxycholesterol | + | − | − |
| 24(S)-hydroxycholesterol | − | − | − |
| campesterol | − | N/A | N/A |
| β-sitosterol | − | N/A | N/A |
| stigmasterol | − | N/A | N/A |

Substrate testing for cytochrome P450 enzymes co-expressed with CPR. Production of a detectable product is indicated by a (+).
CYP90B27 refers to cholesterol 22-hydroxylase, CYP90G1 refers to 22-hydroxy-26-aminocholesterol 22-oxidase, and CYP94N1 refers to 22-hydroxycholesterol 26-hydroxylase/oxidase.

Production of a detectable product is indicated by a Yes. Abbreviations for substrates are used for formatting purposes and the full names are as follows from right to left: 22(R)-Hydroxycholesterol, 22(S)-Hydroxycholesterol, 26-Hydroxycholesterol, 22, 26-Dihydroxycholesterol, 22-Keto cholesterol, 4β-Hydroxycholesterol, 7β-Hydroxycholesterol, and 24 (S)-Hydroxycholesterol.

Standards were obtained from Sigma Aldrich, Research Plus, and Avanti. For GC-MS analysis, 5 individual assays per substrate were pooled after incubation at 30° C. for 2 hours; one assay produced sufficient product for analysis by LC-MS/MS. Assay conditions were as follows: 80 µl S. frugiperda Sf9 cell suspension (obtained by re-suspension of 50 ml viral infected culture pellet in 3.5 ml of 100 mM tricine pH 7.4/5 mM thioglycolic acid), 60 mM potassium phosphate buffer pH 8, 1.25 mM NADPH, 7.5 µM substrate, and $H_2O$ in a total volume of 200 µl. Controls were performed with no enzyme and S. frugiperda Sf9 cells expressing an unrelated cytochrome P450, or CPR-only, for each assay.

The 22-hydroxycholesterol-26-al transaminase enzyme assay contained 55 µl S. frugiperda Sf9 cell suspension infected with cholesterol 22-hydroxylase, 22-hydroxycholesterol 26-hydroxylase/oxidase, 22-hydroxy-26-aminocholesterol 22-oxidase and CPR modified baculoviruses (to provide 22-hydroxycholesterol-26-al substrate), 40 µl S. frugiperda Sf9 cells expressing 22-hydroxycholesterol-26-al transaminase, 60 mM potassium phosphate buffer pH 8, 1.5 mM DTT, 100 µM pyridoxal-5-phosphate, 16 mM GABA, 500 µM NADPH, and water to a total volume of 200 µl. Assay mixes lacking either enzyme or GABA, and control cytochrome P450 assays were run in parallel and each was allowed to proceed for 2 hours at 30° C. Samples were extracted twice with 400 µl ethyl acetate. Samples were then dried under $N_2$, re-suspended in 50 µl 80% methanol, and injected onto LC-MS/MS with conditions described above. All enzyme assays utilized crude S. frugiperda Sf9 protein extracts that contain endogenous metabolites, including cholesterol.

Assays to Clarify Order of Enzymatic Transformations

Assay for GC-MS: Cytochrome P450 enzyme assay conditions were identical to those stated above using *S. frugiperda* Sf9 cell suspensions with the following modifications. First, 12 assays each containing 22-hydroxy-26-aminocholesterol 22-oxidase+CPR, 22-hydroxycholesterol 26-hydroxylase/oxidase+CPR, or control cytochrome P450+CPR and each with pure 22(R)-hydroxycholesterol were allowed to incubate overnight at 30° C. Like assays were pooled, extracted 3 times with 2 volumes ethyl acetate, dried under $N_2$, and re-suspended in 180 µl of 25% DMSO. Extracts containing the enzymatic product of the 22-hydroxycholesterol 26-hydroxylase/oxidase+CPR and 22(R)-hydroxycholesterol were divided equally and used as substrate for 22-hydroxy-26-aminocholesterol 22-oxidase+CPR and control cytochrome P450+CPR. Extracts containing the enzymatic product of 22-hydroxy-26-aminocholesterol 22-oxidase+CPR and 22(R)-hydroxycholesterol were divided and used as substrate in 6 assays containing 22-hydroxycholesterol 26-hydroxylase/oxidase+CPR and 6 assays containing control cytochrome P450+CPR. Control P450+CPR assay was run in parallel, treated identically and added to another control P450 assay. Refer to FIG. 1A for an overview of the experiment. Assays were allowed to incubate for 20 min at 30° C. then stopped by addition of 20 µl of 20% TCA with vortexing. Like assays were pooled, extracted, derivatized, and analyzed by GC-MS using the method stated above.

Assay for LC-MS/MS: All assays utilized crude *frugiperda* Sf9 cell suspensions. Enzyme assays started with a combination of cholesterol 22-hydroxylase+CPR and 22-hydroxycholesterol 26-hydroxylase/oxidase+CPR (8 individual reactions) in parallel to cholesterol 22-hydroxylase+CPR and 22-hydroxy-26-aminocholesterol 22-oxidase+CPR (8 reactions). Assays were extracted, and fed to 22-hydroxycholesterol 26-hydroxylase/oxidase+CPR, 22-hydroxy-26-aminocholesterol 22-oxidase+CPR, or 22-hydroxycholesterol-26-al transaminase for several possible enzyme combinations (4 reactions each). Like samples were pooled, extracted, and added to 2 reactions each with enzyme not yet utilized previously. Refer to FIG. 1B for complete list of combinations. Samples were taken at each step post extraction for LC-MS/MS analysis and run with the method stated above.

Enzymatic Product Purification for NMR and High Resolution MS for Structure Elucidation Large-scale 750 ml *S. frugiperda* Sf9 cultures were grown expressing viral combinations 5-7 (Table 5) of the *V. californicum* enzymes as previously described. Cells were collected after three days and re-suspended in 10 ml of 100 mM tricine pH 7.4/5 mM thioglycolic acid; then extracted 3 times with 2 volumes of hexane or ethyl acetate. The remaining aqueous supernatant was extracted once with 1 volume of hexane or ethyl acetate. Extracts for each infection were then pooled, dried under $N_2$, and re-suspended in 5 ml of absolute methanol.

The extracts were purified on a Waters HPLC system equipped with a 2707 autosampler, 1525 binary pump, 2998 photodiode array detector, and Waters Fraction Collector III. In some cases, samples were cleaned up by Solid Phase Extraction (SPE), before HPLC purification. For HPLC extracts were concentrated to 500 µl and then injected in 50 µl portions onto a Phenomenex Gemini C-18 NX column (150×2.00 mm, 5 µm) with the same solvents used for LC-MS/MS as described above with the following binary gradient: Solvent B was held at 20% for 2 min, then 2-11 min 20-30% B, 11-18 min 30-100% B, 18-30 min 100% B, 30-31 min 100-20% B, and held at 20% B for an additional 5 minutes. The flow rate was 0.5 ml/min; 0.5 ml fractions were collected. The resulting fractions were then analyzed by GC-MS or LC-MS/MS as described above, and selected samples were analyzed by NMR or by high resolution MS. NMR spectra were acquired in MeOD at 600 MHz on a BrukerAvance 600 MHz spectrometer equipped with a BrukerBioSpin TCI 1.7 mm MicroCryoProbe. Proton, gCOSY, ROESY, gHSQC, and gHMBC spectra were acquired; $^{13}C$ chemical shifts were obtained from the HSQC and HMBC spectra. Chemical shifts are reported with respect to the residual non-deuterated MeOD signal. Refer to Tables 7 and 8 for NMR designations for 22-keto-cholesterol and 22-keto-26-hydroxycholesterol, respectively. For high resolution MS, the sample was diluted 1:10 in 80% acetonitrile:water (LC-MS grade) containing 0.1% formic acid and infused into an LTQ-Orbitrap Velos Pro (Thermo-Fisher Scientific, San Jose, Calif.) using a Triversa Nanomate (Advion, Ithaca, N.Y.). Data were collected in positive ion mode, detected in the Orbitrap at a nominal resolution setting of 60,000 at m/z 400. Precursors were determined with a wide SIM scan (m/z 385-430). Precursors were isolated in the ion-trap and transferred to the HCD cell for fragmentation at 35 NCE (m/z 418) and 50 NCE (m/z 398). Data were analyzed manually using the Qualbrowser application of Xcalibur (Thermo-Fisher Scientific, San Jose, Calif.).

TABLE 7

22-Keto-cholesterol NMR in MeOD

| position | $^{13}C$ | $^1H$ |
|---|---|---|
| 1 | 38.3 | 1.09$^a$ |
|  |  | 1.88 (dt, 13.0, 3.5) |
| 2 | 31.8 | 1.49$^a$ |
|  |  | 1.78 m |
| 3 | 72.1 | 3.40 m |
| 4 | 42.6 | 2.23 m |
| 5 | 141.9 |  |
| 6 | 122.1 | 5.34 m |
| 7 | 32.7 | 1.55$^a$ |
|  |  | 1.98$^a$ |
| 8 | 36.8 |  |
| 9 | 51.4 | 0.98 (td, 11.0, 5.0) |
| 10 | 37.7 |  |
| 11 | 22.0 | 1.50$^a$ |
|  |  | 1.55$^a$ |
| 12 | 40.8 | 1.31$^a$ |
|  |  | 2.01$^a$ |
| 13 | 43.4 |  |
| 14 | 57.3 | 1.07$^a$ |
| 15 | 25.8 | 1.60$^a$ |
| 16 | 28.2 | 1.19 m |
|  |  | 1.62$^a$ |
| 17 | 53.6 | 1.58$^a$ |
| 18 | 12.2 | 0.76 s |
| 19 | 19.6 | 1.03 s |
| 20 | 50.2 | 2.59 m |
| 21 | 16.7 | 1.10 (d, 7.0) |
| 22 | 217.8 |  |
| 23 | 40.4 | 2.45 m |
|  |  | 2.54 m |
| 24 | 33.1 | 1.41 m |
| 25 | 28.6 | 1.52$^a$ |
| 26 | 13.2 | 0.90 (d, 6.8) |
| 27 | 22.5 | 0.90 (d, 6.8) |

TABLE 8

22-keto-26-hydroxycholesterol (SF 20797). NMR in MeOD

| position | $^{13}$C | $^{1}$H |
|---|---|---|
| 1 | 38.3 | 1.09$^a$ |
|   |      | 1.88 (dt, 13.6, 3.3) |
| 2 | 31.9 | 1.49$^a$ |
|   |      | 1.79 m |
| 3 | 72.1 | 3.39$^a$ |
| 4 | 42.7 |  |
| 5 | 142.1 |  |
| 6 | 122.1 | 5.34 (br d, 5.1) |
| 7 | 32.7 | 1.50$^a$ |
|   |      | 1.97$^a$ |
| 8 | 32.5 | 1.45$^a$ |
| 9 | 51.3 | 0.98 (td, 11.2, 5.0) |
| 10 | 37.4 |  |
| 11 | 21.8 | 1.53$^a$ |
|    |      | 1.57$^a$ |
| 12 | 40.6 | 1.30$^a$ |
|    |      | 2.01$^a$ |
| 13 | 43.2 |  |
| 14 | 57.1 | 1.07$^a$ |
| 15 | 25.4 | 1.15$^a$ |
|    |      | 1.63$^a$ |
| 16 | 28.1 | 1.21$^a$ |
|    |      | 1.63$^a$ |
| 17 | 53.3 | 1.60$^a$ |
| 18 | 12.0 | 0.76 s |
| 19 | 19.6 | 1.03 s |
| 20 | 50.2 | 2.60$^a$ |
| 21 | 16.7 | 1.11 (d, 7.0) |
| 22 | 217.0 |  |
| 23 | 40.1 | 2.46 (ddd, 17.6, 9.2, 5.9) |
|    |      | 2.62$^a$ |
| 24 | 27.4 | 1.31$^a$ |
|    |      | 1.67$^a$ |
| 25 | 35.9 | 1.56$^a$ |
| 26 | 16.6 | 0.91 (d, 6.6) |
| 27 | 67.7 | 3.35 (dd, 10.6, 6.2) |
|    |      | 3.40$^a$ |

Dimedone Aldehyde Trapping

Enzyme assays containing 22-hydroxycholesterol 26-hydroxylase/oxidase and 22(R)-hydroxycholesterol as substrate, or cholesterol 22-hydroxylase+22-hydroxycholesterol 26-hydroxylase/oxidase utilizing endogenous cholesterol in S. frugiperda Sf9 cells as substrate, or cholesterol 22-hydroxylase+22-hydroxycholesterol 26-hydroxylase/oxidase and 22-hydroxycholesterol-26-al transaminase, also utilizing endogenous cholesterol in S. frugiperda Sf9 cells as substrate with either 80 µl 10 mg/ml dimedone in 10% DMSO or 80 µl 10% DMSO were incubated overnight at 30° C. Assays were extracted twice with 2 volumes ethyl acetate and analyzed by LC-MS/MS. All cytochrome P450 enzymes were co-expressed with CPR.

Sodium Borohydride Reduction 2 ml S. frugiperda Sf9 cells expressing cholesterol 22-hydroxylase+22-hydroxycholesterol 26-hydroxylase/oxidase+22-hydroxycholesterol-26-al transaminase+22-hydroxy-26-aminocholesterol 22-oxidase+CPR were extracted twice with equal volume ethyl acetate. Extracts were divided equally, dried under $N_2$, and re-suspended in 50 µl 80% methanol each. One sample was treated with 50 µl 1 M $NaBH_4$ in 1 M NaOH for 15 minutes. 100 µl $H_2O$ were added to both samples, and each extracted twice with equal volumes of chloroform. Samples were dried under $N_2$, re-suspended in 50 µl 80% methanol and analyzed by LC-MS/MS as described above. S. frugiperda Sf9 cells expressing CPR only were run in parallel as control.

Semi-Quantitative RT-PCR

Semi-quantitative RT-PCR was performed on cDNA prepared from each V. californicum tissue using Taq DNA polymerase (New England Biolabs). Cycle parameters can be found in Table 3; primers specific to each gene can be found in the Sequence Listing (SEQ ID NO:27-48). Arabidopsis Protein Phosphatase 2A SubunitA2 (PP2AA2) cDNA sequence was used to BLAST© the V. californicum transcriptome to find a suitable homolog to be used as a housekeeping gene for normalization. Resulting products were run on a 2% agarose gel and band intensity was quantitated with the image processing and analysis software Image J.

SDS-PAGE

SDS-PAGE was performed for each functional gene to verify recombinant protein production. 10% Mini-PROTEAN TGX (Biorad) precast gels were used on a Mini-PROTEAN Tetra Cell (Biorad). 1 µl S. frugiperda Sf9 cell suspension co-infected with V. californicum cytochrome P450 and CPR was loaded onto the gel alongside a CPR only control and pure BSA (Fisher Scientific). Protein bands were visualized by coomassie blue staining using commassie brilliant blue R-250 (Amresco).

Results and Discussion

RNA-Seq and De Novo Transcriptome Assembly

Multiplex paired-end sequencing of V. californicum cDNA produced from bulb, flower, leaf, fall rhizome, spring rhizome, root, green shoot, white shoot, and tissue culture samples on two 2×50 bp Hi-Seq channels resulted in 41,106,915 bases of an average read count of 2,520. The raw reads in the HiSeq datasets were analyzed and filtered for artifacts/contaminants. The reads were 5' and 3' quality trimmed using a FRED score of 15 to eliminate noisy reads. The de novo short read assembly was produced with multiple runs of de Bruijn assembler (kmer sweep). Native Abyss scaffolding and gap closing was performed to produce collections of synthetic EST scaffolds. These scaffolds were merged and assembled with Mira, and any remaining redundancy was removed to produce a final contig set. Post-processing included protein prediction as FASTA, protein product motif annotation as GFF3, and post-hoc alignment of cleaned read data to contigs. The results of the dataset processing and assembly produced 56,994 contigs. The depth of the transcriptome sequencing was sufficient to utilize mapped read-counts as a metric of relative gene expression. The average contig sequence length indicates high quality assembly and was sufficient for downstream sequence alignment and phylogenetic gene tree estimation.

Transcriptome Dataset Interrogation

Predicted peptide sequences were submitted to Pfam, Uniprot, and Superfamily in addition to BLAST® search at NCBI to provide an annotation to each translated contig. Expression data for each contig was normalized using total reads per organ type to serve as the dataset for Haystack. LC-MS/MS determination of the steroid alkaloid profile in the same V. californicum tissues used for RNA-Seq resulted in a pronounced accumulation of cyclopamine in rhizome, fall rhizome being the highest, followed by root and bulb (FIG. 2). The accumulation of highest quantities of cyclopamine in subterranean organs suggests that biosynthesis occurs in underground organs of the plant. Transport of metabolites in plants has been demonstrated (i.e. nicotine in tobacco and cyanogenic glucosides in cassava), but secondary metabolites most often are synthesized at or near their site of accumulation. Since little is known about cyclopamine biosynthesis in Veratrum, it was initially hypothesized that underground tissues (rhizome, root, and bulb) are biosynthetic for cyclopamine.

Because ca. 20 times more cyclopamine accumulates in subterranean organs compared to aerial organs, root, rhizomes, and bulb were given a value of 20 for the Haystack input. The above ground organs leaf, stem, flower, and tissue culture samples (derived from seed) were designated a value of 1 in order to create a generalized model based on biosynthesis. Haystack uses a model-based, pattern-matching algorithm to identify genes with expression patterns that fit a predefined input model (here cyclopamine accumulation). In our approach, the LC-MS/MS alkaloid data for *Veratrum* is the input model used to search the deep transcriptome experimental dataset of *Veratrum*. Haystack determines the correlation of the experimental dataset with each input model pattern and applies a series of statistical tests and ad hoc filters to identify genes of interest. Using a correlation cut off of 0.7, 3,219 genes were obtained that fit the 20:1 subterranean organ:aerial organ cyclopamine accumulation model.

In parallel to co-localization modeling, the protein-coding gene sequences in the *Veratrum* RNAseq transcriptome dataset were classified into putative gene families using PlantTribes 2.0. PlantTribes is based on the similarity-based clustering procedure TribeMCL, and incorporates the *Veratrum* protein sequences into existing plant tribe alignments and phylogenies. In addition to this tribe clustering approach, a complete minimal representative dataset from all available plant species of cytochromes P450 relevant to alkaloid biosynthesis was developed. Cytochromes P450 were chosen first due to the hypothesized number of oxidative transformations necessary to convert cholesterol into cyclopamine. Our experience in plant alkaloid biosynthesis has taught us that these types of transformations are typically catalyzed by cytochromes P450. The second choice of enzyme class would be 2-oxo-glutarate-dependent dioxygenases, should the cytochrome P450 dataset not yield positive results.

This dataset can be used to better define and cluster the tribes that are of most interest to the cyclopamine pathway. Multiple sequence alignment and phylogenetic tree estimation were done on these relevant tribes and gene families using the MAFFT alignment software and RAxML for maximum likelihood tree generation. In addition to *Veratrum*, the RNAseq transcriptome assembly sequences from *Colchicum autumnale* (autumn crocus) and *Narcissus* (daffodil) were included in the tribe clustering steps of the computational pipeline. Similar to *Veratrum*, these two species are also monocots. However, *Colchicum* and *Narcissus* do not produce cyclopamine, but instead make the unrelated alkaloids colchicine and galanthamine, respectively. Therefore, *Colchicum* and *Narcissus* sequences helped identify tribe clusters that only contain *Veratrum* genes.

A series of selection criteria were established to score and sort the resulting clades. A given clade was scored on the percentage of clade members that significantly co-localized with cyclopamine (e.g. present in the Haystack output dataset). Clades missing significantly co-localized gene members were penalized. Clades containing genes that were not significantly co-localized with the alkaloid were penalized. Lastly, clades that contain genes from species that do not produce cyclopamine incurred a score penalty. Therefore, the *Colchicum* and *Narcissus* gene sequences served as controls in the clade-scoring portion of the computational pipeline. These criteria were combined to score and rank the clades that contain Haystack output gene members to identify the clade(s) with the highest likelihood of containing genes that function in the steroid alkaloid biosynthesis pathway. Candidate genes from clades with the highest scores were selected for downstream functional characterization (Table 9; FIG. 10).

TABLE 9

Selected top-scoring cytochrome P450 candidate cDNAs for the enzymatic conversion of cholesterol to cyclopamine

| Gene ID | Putative function |
| --- | --- |
| >medp_verca-20110208\|2398 | similar to CYP71D unknown function |
| >medp_verca-20110208\|31930 | similar to CYP71D unknown function |
| >medp_verca-20110208\|10041 | similar to CYP728 taxane 13a-hydroxylase |
| >medp_verca-20110208\|13942 | similar to CYP734 brassinolide C-26 hydroxylase |
| >medp_verca-20110208\|13284 | similar to CYP90B1 steroid C-22 hydroxylase |
| >medp_verca-20110208\|18017 | similar to CYP90B1 steroid C-22 hydroxylase |
| >medp_verca-20110208\|18580 | similar to CYP90B1 steroid C-22 hydroxylase |
| >medp_verca-20110208\|2646 | similar to CYP90B1 steroid C-22 hydroxylase |
| >medp_verca-20110208\|32399 | similar to CYP90B1 steroid C-22 hydroxylase |
| >medp_verca-20110208\|12709 | similar to CYP94D unknown function |

Since a nitrogen atom must be introduced into the steroid skeleton to produce an alkaloid, aminotransferases fitting the model were included in the candidate gene list as well (Table 10).

TABLE 10

Selected top-scoring transaminases in the steroidal alkaloid biosynthetic pathway

| Gene ID | Putative function |
| --- | --- |
| >medp_verca-20110208\|12217 | aminotransferase ACS10 |
| >medp_verca-20110208\|12084 | gamma aminobutyrate transaminase 1, mitochondrial-like |
| >medp_verca-20110208\|5285 | 1-aminocyclopropane-1-carboxylate synthase |
| >medp_verca-20110208\|28717 | aminotransferase ACS12-like |
| >medp_verca-20110208\|15871 | histidinol-phosphate aminotransferase, chloroplastic-like |
| >medp_verca-20110208\|10159 | cysteine desulfurase 1 |
| >medp_verca-20110208\|1461 | methionine S-methyltransferase |

Full-length candidate cDNAs were expressed using *S. frugiperda* Sf9 cells using a baculovirus-based expression vector due to the suitability of insect cells for producing functional post transcriptionally-modified, membrane-bound proteins, and for the ability to accommodate multiple-virus infections. *S. frugiperda* Sf9 cells provide a facile synthetic biology platform for the systematic refactoring of plant biosynthetic pathways.

Cholesterol 22-hydroxylase

Figure 15A:
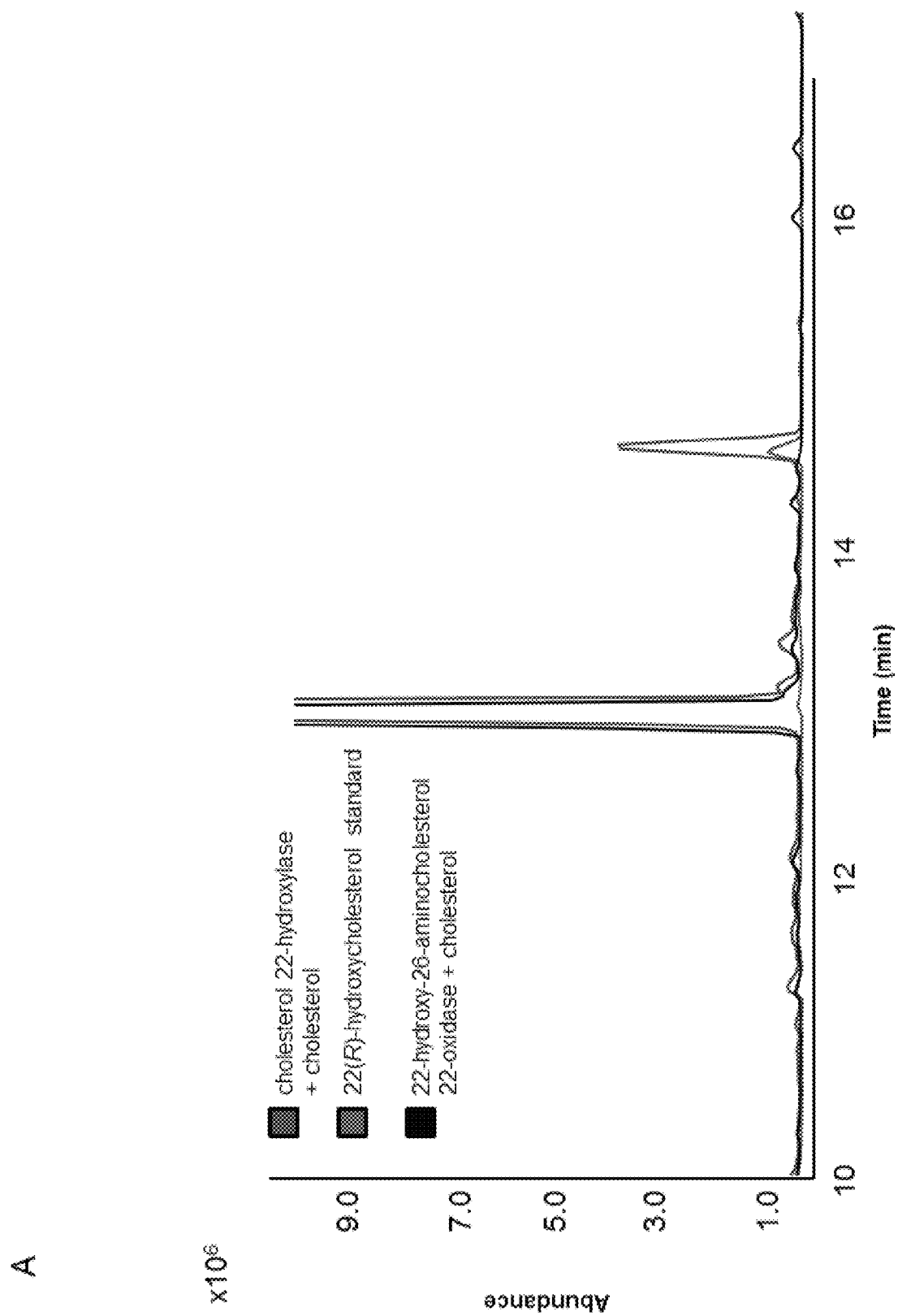

The top-scoring candidate cDNAs resulting from interrogation of the *V. californicum* transcriptome dataset were systematically introduced, together with *E. californica* cytochrome P450 reductase (CPR), into *S. frugiperda* Sf9 insect cells, which were harvested as previously described and used in enzyme assays with cholesterol as substrate. Cholesterol was chosen as the initial precursor for study based upon existing knowledge of steroid alkaloid biosynthesis. Other related compounds were also tested in enzyme assays to determine enzyme specificity (Table 6). The contig designated VC2646, which annotated as a steroid C-22 hydroxylase, added a hydroxyl group to the 22-position of cholesterol exclusively in the Rorientation (FIG. 3; FIG. 15A). One homolog of VC2646 was identified having 99.8% identity and performing the same enzymatic function. CYP assignments for both homologs are CYP90B27v1 and CYP90B27v2. The inventors have designated this enzyme cholesterol 22-hydroxylase. S. frugiperda Sf9 cells expressing cholesterol 22-hydroxylase and the E. californica CPR demonstrated that this enzyme could produce the product in vivo during viral infection utilizing endogenous S. frugiperda cholesterol. Cholesterol 22-hydroxylase also hydroxylated 26-hydroxycholesterol and 7β-hydroxycholesterol, presumably in the 22-position. Cholesterol 22-hydroxylase oxidizes the hydroxyl group at the 22-position to a ketone, but only to a low degree (FIG. 3). The identity of the enzymatic product of cholesterol 22-hydroxylase acting on cholesterol was confirmed by GC-MS comparison to 22(R)-hydroxycholesterol authentic standard. 22(R)- and 22(S)-hydroxycholesterol are chromatographically resolved by this GC-MS method.

22-Hydroxycholesterol 26-hydroxylase/oxidase

To identify the second enzyme in the pathway, a series of triple infections of S. frugiperda Sf9 cells were carried out that all contained cholesterol 22-hydroxylase and E. californica CPR, but varied the second enzyme. Candidates for the second enzyme were the remaining top-scoring candidate cDNAs resulting from interrogation of the V. californicum transcriptome dataset (minus the cholesterol 22-hydroxylase already identified). Contig VC12709 annotated as a fatty acid hydroxylase and was found to hydroxylate 22(R)-hydroxycholesterol at the C-26 position forming 22,26-dihydroxycholesterol (FIG. 3). This enzyme also oxidizes the hydroxyl group at the 26 position creating a highly reactive 22-hydroxycholesterol-26-al (FIG. 11A). Four homologs were discovered, with identities ranging from 93-99% and all possessing identical functionality. Hydroxylation of cholesterol by VC12709 was not detected (FIG. 15B), so this enzyme was subsequently designated 22-hydroxycholesterol 26-hydroxylase/oxidase. CYP assignments for these homologs are CYP94N1v1, CYP94N1v2, CYP94N2v1, and CYP94N2v2. The identity of 22,26-dihydroxycholesterol produced by action of VC12709 on 22(R)-hydroxycholesterol was ultimately determined using the 22-hydroxylating activity of cholesterol 22-hydroxylase to produce 22,26-dihydroxycholesterol from pure 26-hydroxycholesterol and comparing the mass spectra of the two products.

22-Hydroxycholesterol-26-al Transaminase

Figure 12A:
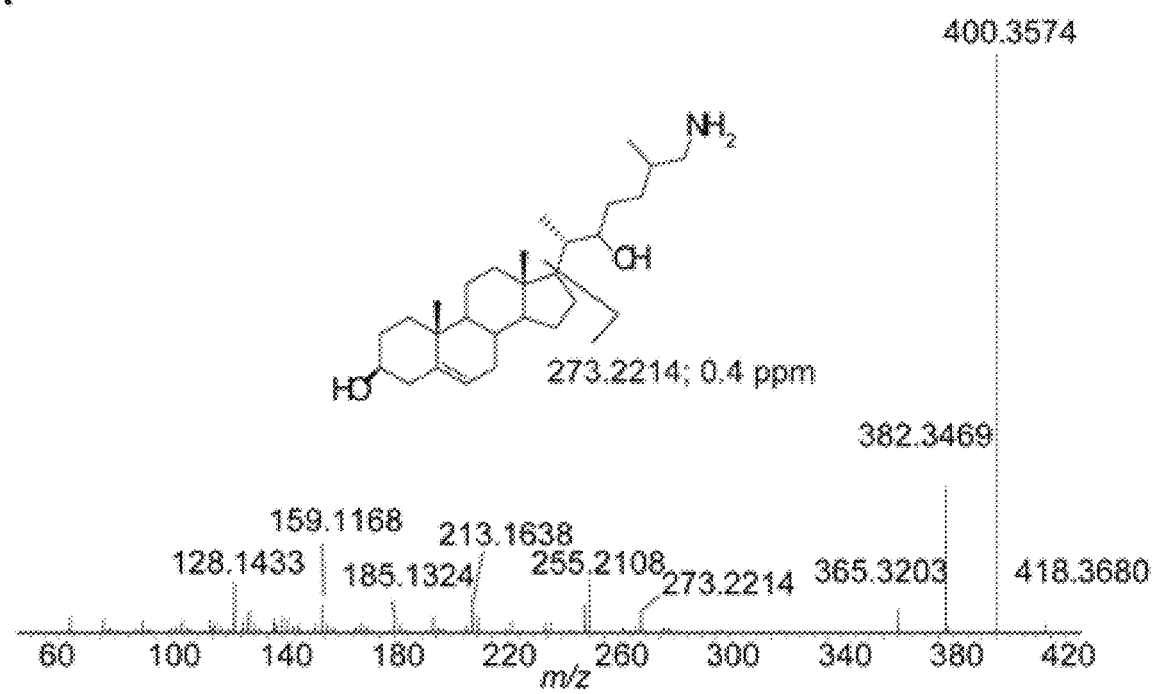
Figure 12B:
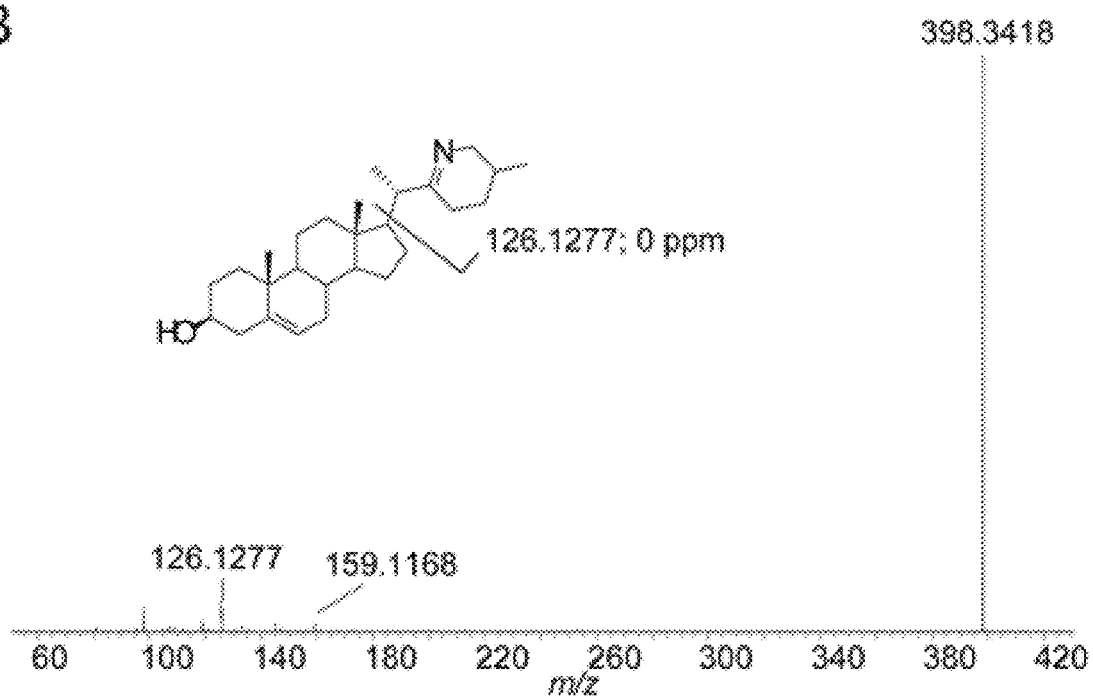

To identify the third enzyme in the pathway, a series of quadruple infections of insect cells were carried out that all contained cholesterol 22-hydroxylase, 22-hydroxycholesterol 26-hydroxylase/oxidase, and E. californica CPR, but varied the third enzyme. Candidates for the third enzyme were the remaining top-scoring candidate cDNAs resulting from interrogation of the V. californicum transcriptome dataset (minus the two enzymes already identified). A GABA transaminase designated VC12084 was shown to incorporate nitrogen into the 26-position of 22-hydroxycholesterol-26-al using GABA as an amino group donor to produce 22-hydroxy-26-aminocholesterol (FIGS. 4A, 4B, 4C and 4D). Three homologs were detected, each with over 99% identity and all catalyzing the same reaction. The structure of 22-hydroxy-26-aminocholesterol was confirmed by high resolution MS (FIGS. 12A and 12B). This enzyme was subsequently designated 22-hydroxycholesterol-26-al transaminase. In corroboration of our results, addition of the hydroxyl group followed by nitrogen addition to the 26-position is supported by early studies using Veratrum grandiflorum in which 22(R),26-dihydroxycholesterol was found to be a predominant sapogenin in budding V. grandiflorum extracts and surmised to be a precursor to the nitrogen-containing metabolite verazine, and recent studies in Solanum lycopersicum which suggest that C-26-hydroxyl is the position of oxidation and transamination based on metabolite accumulation using S. lycopersicum RNAi lines of genes involved in α-tomatine biosynthesis.

22-Hydroxy-26-aminocholesterol 22-oxidase

To identify the fourth enzyme in the pathway, a series of quintuple infections of insect cells were carried out that all contained cholesterol 22-hydroxylase, 22-hydroxycholesterol 26-hydroxylase, 22-hydroxycholesterol-26-al transaminase, and E. californica CPR, but varied the fourth enzyme. Candidates for the fourth enzyme were the remaining top-scoring candidate cDNAs resulting from interrogation of the V. californicum transcriptome dataset (minus the three enzymes already identified). Contig VC13284 also annotated as a steroid C-22 hydroxylase. VC13284 was able to hydroxylate at the 22-position but only slightly above background as detected by LC-MS/MS, but was able to oxidize an existing hydroxyl group at position 22 with much greater efficiency than cholesterol 22-hydroxylase (FIG. 3). VC13284 oxidizes the 22-hydroxy position of 22(R)-hydroxycholesterol to form 22-keto-cholesterol (FIG. 3), 22,26-dihydroxycholesterol to form 22-keto-26-hydroxycholesterol (FIG. 3), and 22-hydroxy-26-aminocholesterol to form a short lived intermediate that spontaneously cyclizes to verazine (FIGS. 4A, 4B, 4C and 4D). Four homologs were isolated, each having more than 97% identity and all performing identical reactions. CYP designations for each sequence are CYP90G1v1, CYP90G1v2, CYP90G1v3, and CYP90G2. The structures of the enzymatic products 22-keto-cholesterol and 22-keto-26-hydroxycholesterol were confirmed by NMR spectroscopy. The structure of verazine was confirmed by high-resolution mass spectrometry (FIGS. 12A and 12B). This enzyme was subsequently designated 22-hydroxy-26-aminocholesterol 22-oxidase.

Figures 13A, 13B, 13C:
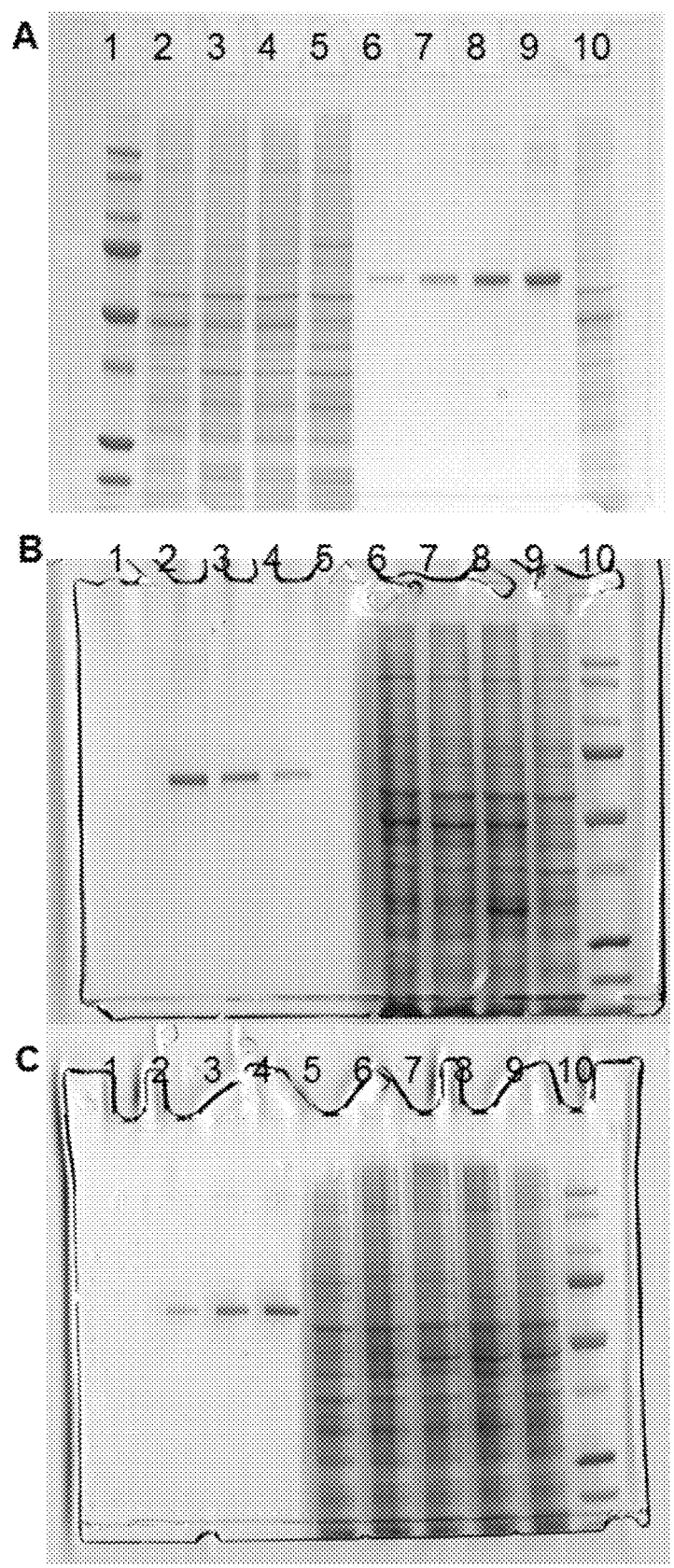
Figures 14A, 14B:
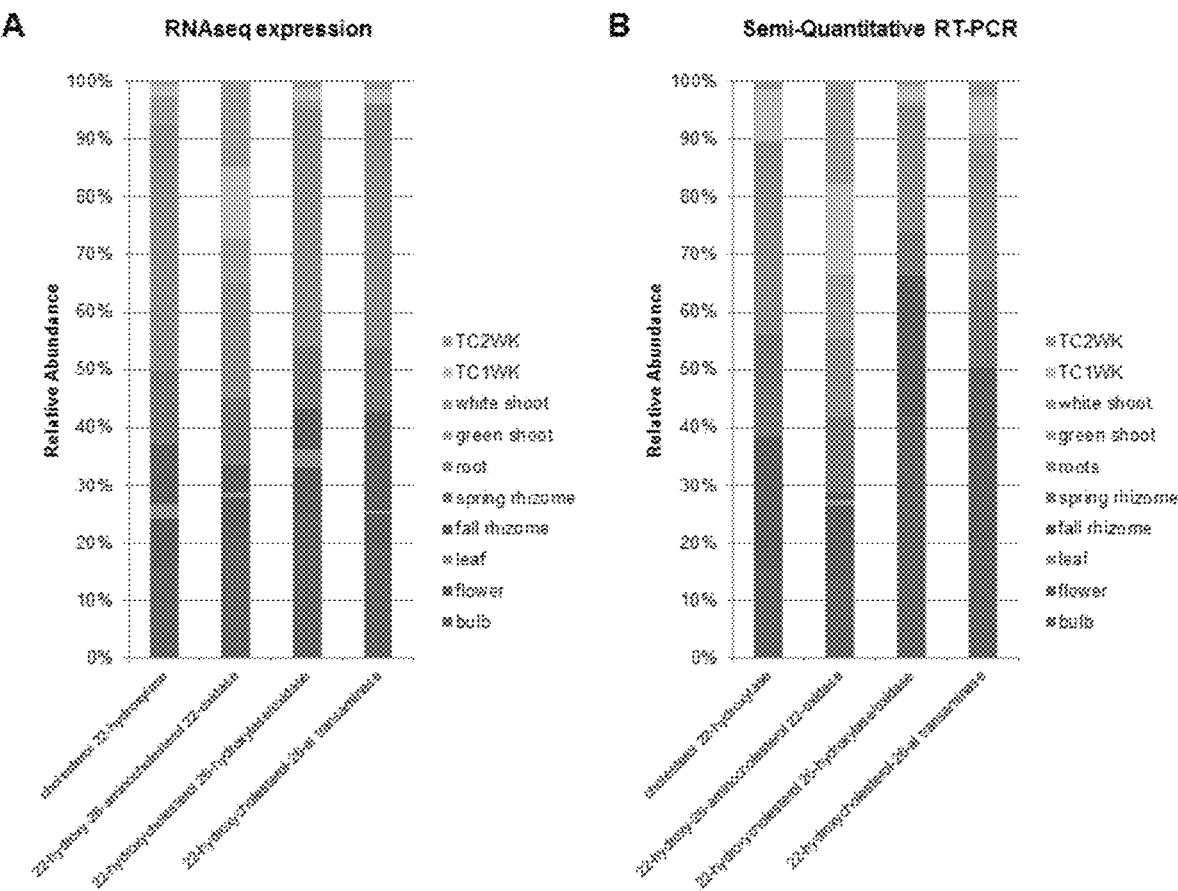

The recombinant proteins cholesterol 22-hydroxylase, 22-hydroxy-26-aminocholesterol 22-oxidase, and 22-hydroxycholesterol 26-hydroxylase/oxidase (all cytochromes P450) could be detected by SDS-PAGE (FIGS. 13A, 13B and 13C); however, a band for the gene product of 22-hydroxycholesterol-26-al transaminase (a GABA transaminase) was not observed. To verify the expression data obtained by read mapping, the inventors performed semi-quantitative RT-PCR on each functionally identified contig. As seen in FIGS. 14A and 14B, the expression patterns found by RNA-seq vs semi-quantitative RT-PCR was comparable. The overall pattern is consistent for each gene between both sets of data. These results validate the use of alignment data from the cleaned reads to the assembled contigs to determine relative gene expression.

Biosynthetic Pathway to Verazine

Figure 15B:
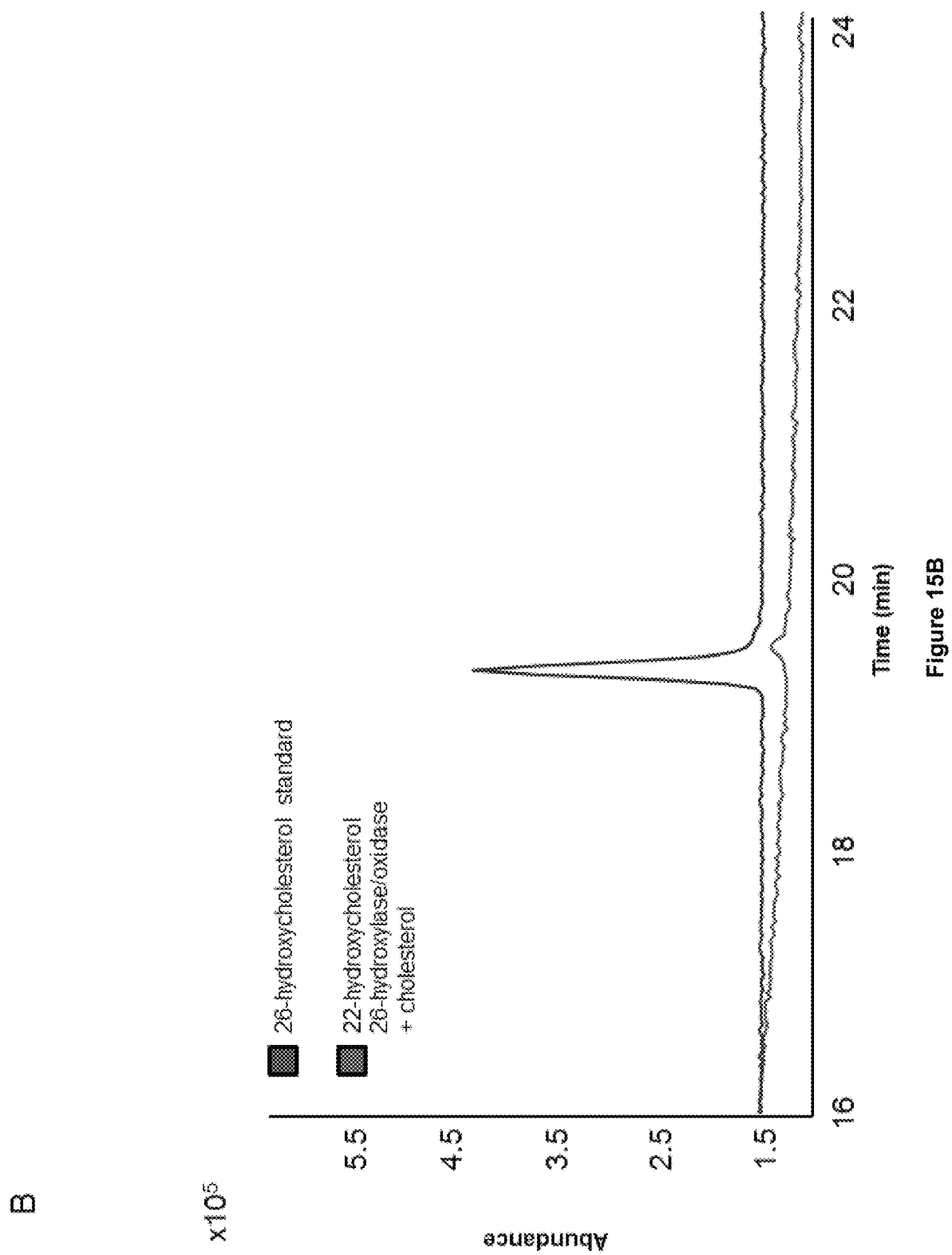

The substrate specificities that were determined for the four new enzymes of steroid alkaloid biosynthesis suggested a potential metabolic grid in the metabolism of cholesterol. To determine the likely order of biosynthesis, the following experiments were done. Cholesterol 22-hydroxylase catalyzes the 22-hydroxylation of cholesterol; this is most likely the first step in the biosynthesis of steroid alkaloids in V. californicum, confirmed by the inability of 22-hydroxycholesterol 26-hydroxylase/oxidase to hydroxylate cholesterol and very low ability of 22-hydroxy-26-aminocholesterol 22-oxidase to accept a substrate without a C-22 hydroxyl group (FIGS. 15A and 15B).

To establish the pathway order after 22-hydroxylation of cholesterol, a series of enzyme assays were carried out using *S. frugiperda* Sf9 cell extracts containing each cytochrome P450 co-expressed only with *E. californica* CPR (or no co-expression in regards to 22-hydroxycholesterol-26-al transaminase). The order of addition for each enzyme was varied, and products were analyzed by GC-MS or LC-MS/MS. The flow chart for both sets of experiments is presented in FIGS. 1A and 1B. For each set of experiments, enzyme assays were extracted (at each arrow in FIGS. 1A and 1B) to provide substrate for the next enzyme assay and subsequent enzymes were tested in a systematically varied order.

Figure 16C:
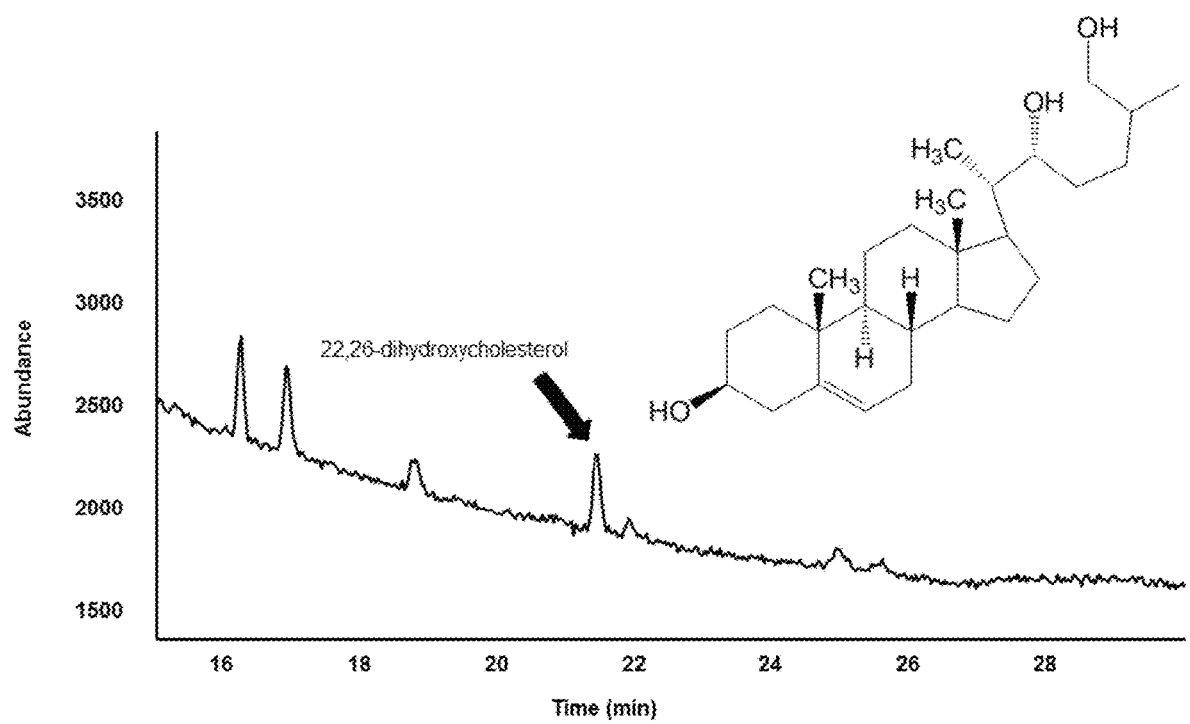
Figure 16D:
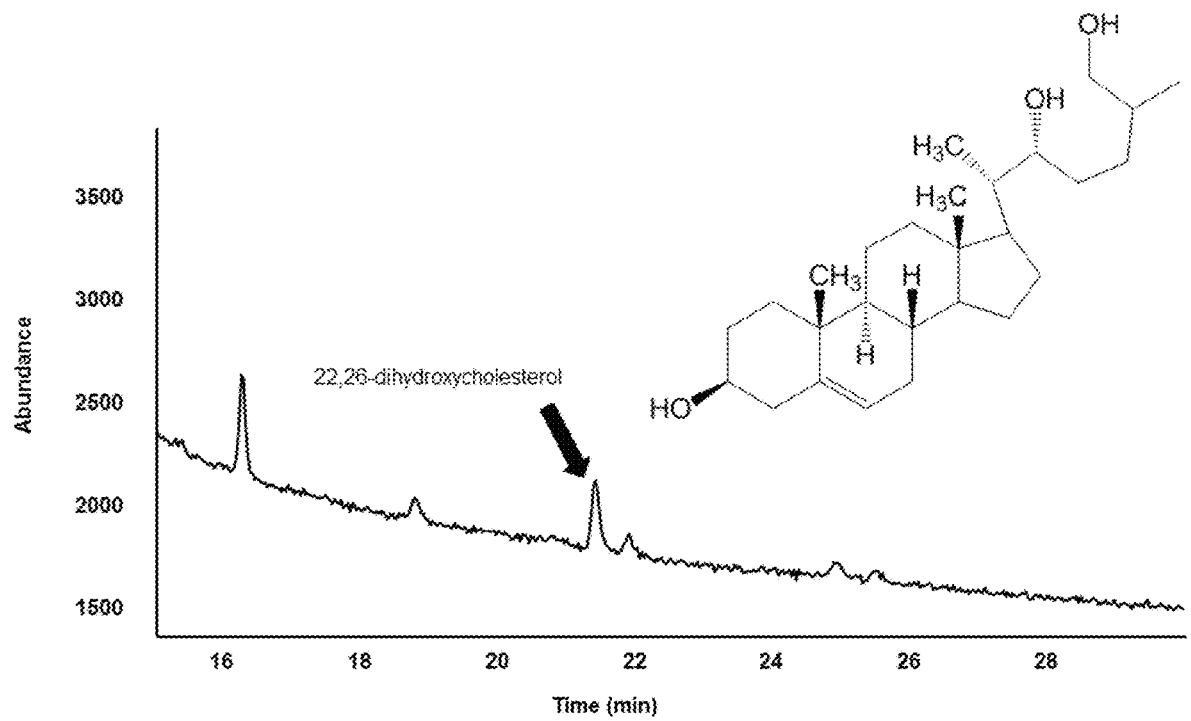
Figure 16E:
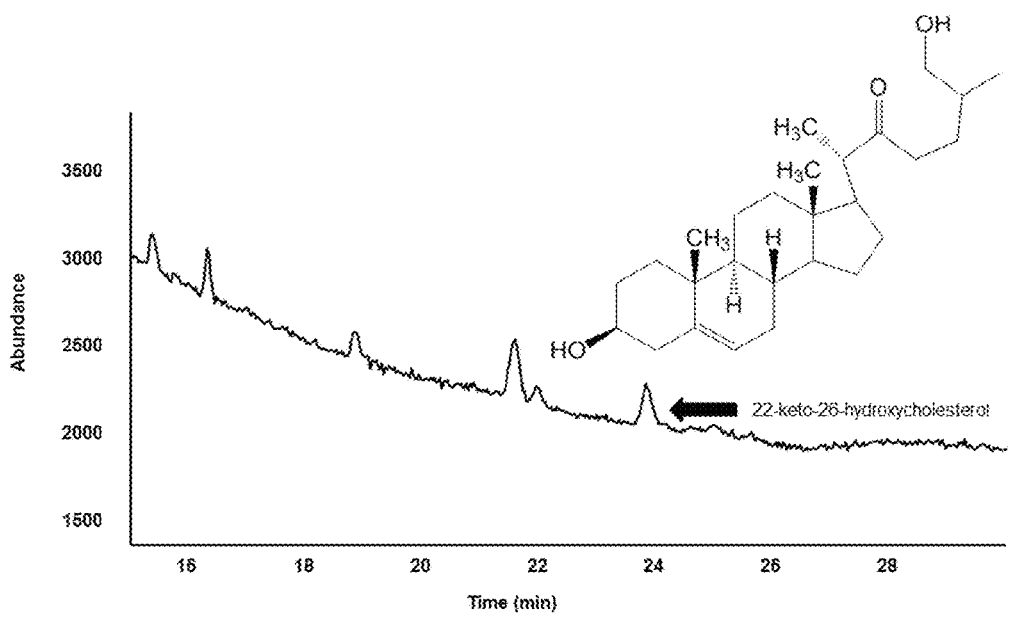
Figure 16F:
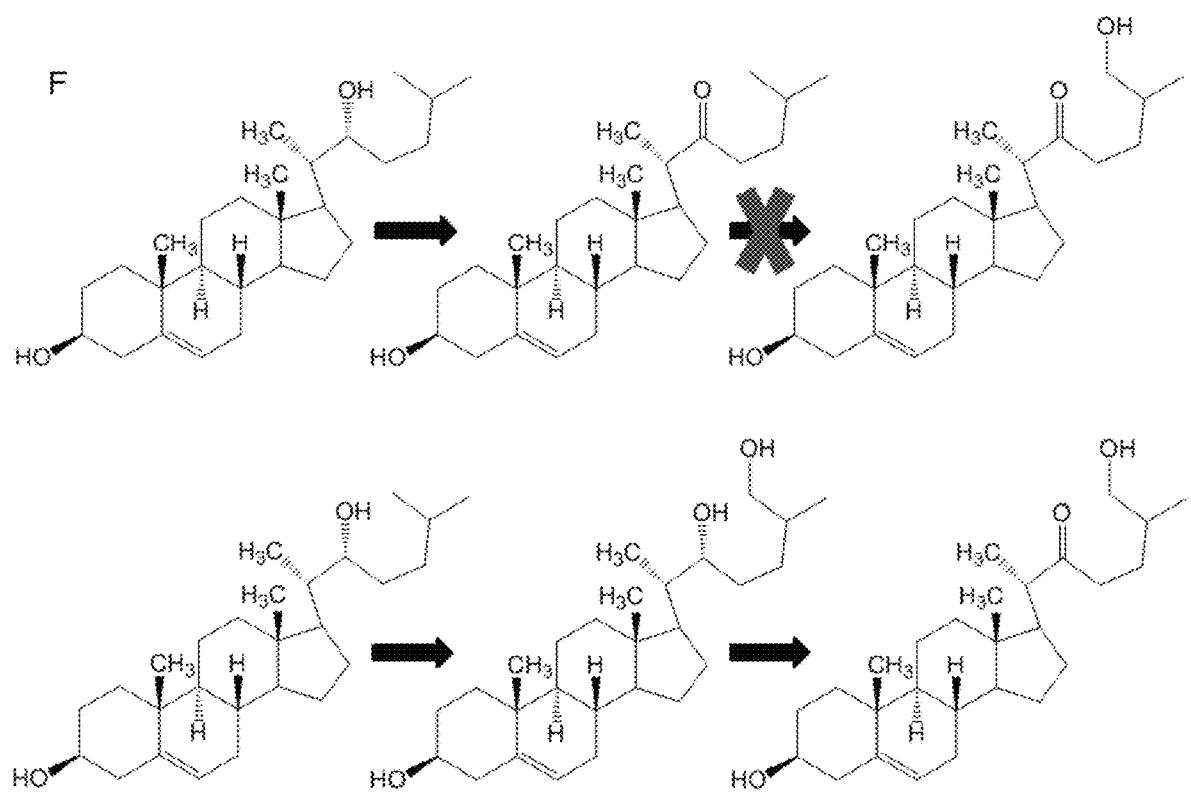

Initially, 22-hydroxy-26-aminocholesterol 22-oxidase was incubated with 22(R)-hydroxycholesterol to produce 22-keto-cholesterol; the enzymatic product was extracted, and then tested as substrate with 22-hydroxycholesterol 26-hydroxylase/oxidase. In parallel, 22-hydroxycholesterol 26-hydroxylase/oxidase was incubated with 22(R)-hydroxycholesterol to produce 22,26-dihydroxycholesterol; the compound was extracted, and then tested as substrate with 22-hydroxy-26-aminocholesterol 22-oxidase. As seen in FIG. 16C; E, 22-keto-26-hydroxycholesterol was only produced at detectable levels by 22-hydroxy-26-aminocholesterol 22-oxidase from 22,26-dihydroxycholesterol. 22-Hydroxycholesterol 26-hydroxylase/oxidase was unable to hydroxylate 22-keto-cholesterol at levels detected by GC-MS. The ability of 22-hydroxy-26-aminocholesterol 22-oxidase to accept 22,26-dihydroxycholesterol as substrate and produce 22-keto-26-hydroxycholesterol, along with the lack of product detection for 22-hydroxycholesterol 26-hydroxylase/oxidase incubated with 22-keto-cholesterol, provided evidence that 22-hydroxycholesterol 26-hydroxylase/oxidase acted directly after cholesterol 22-hydroxylase. This evidence was substantiated with another set of enzyme assays, beginning with cholesterol 22-hydroxylase, showing that 22-hydroxycholesterol 26-hydroxylase/oxidase produced very little product when provided with 22-keto-cholesterol (using the increased sensitivity of LC-MS/MS for detection) as seen in FIG. 11B, as compared to the large amount of product produced when 22,26-dihydroxycholesterol is acted upon by 22-hydroxy-26-aminocholesterol 22-oxidase (FIG. 11A).

Figures 4A, 4B:
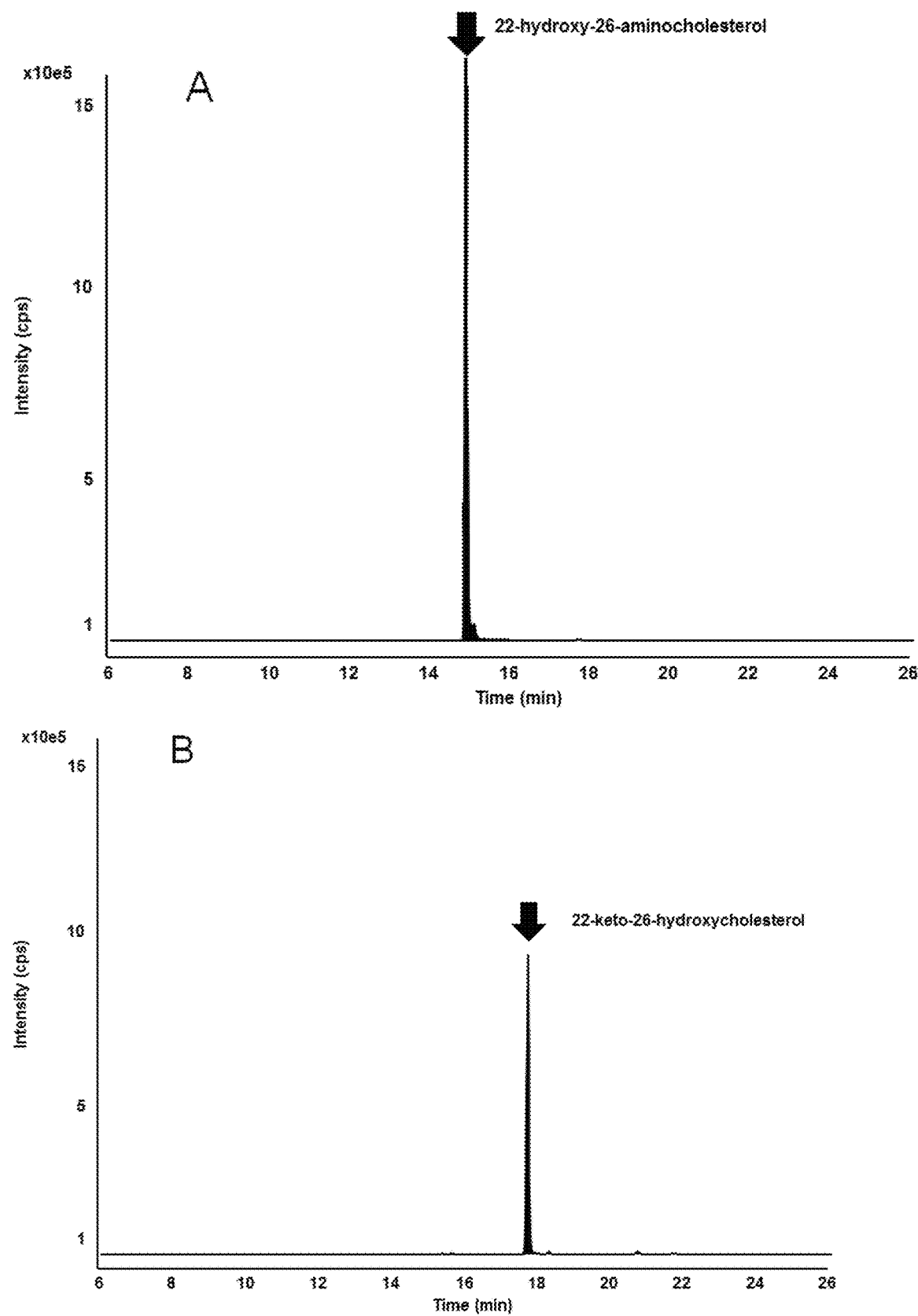
Figure 4C:
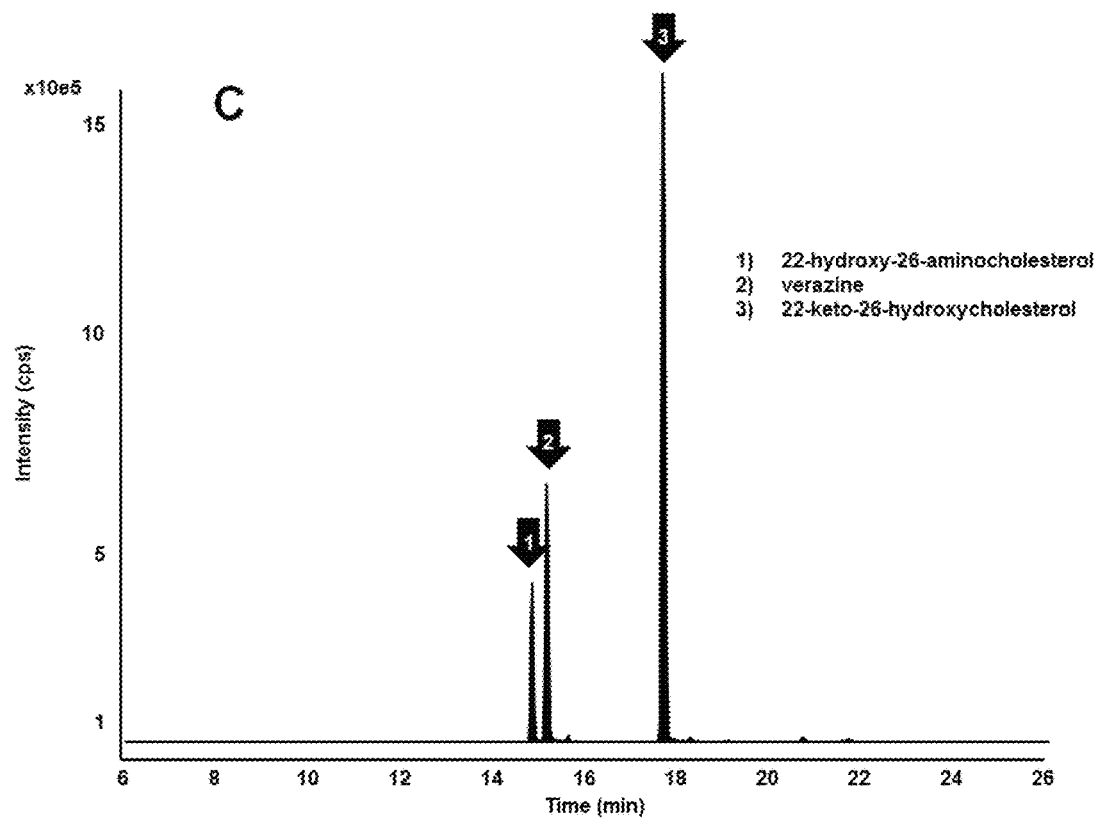
Figure 4D:
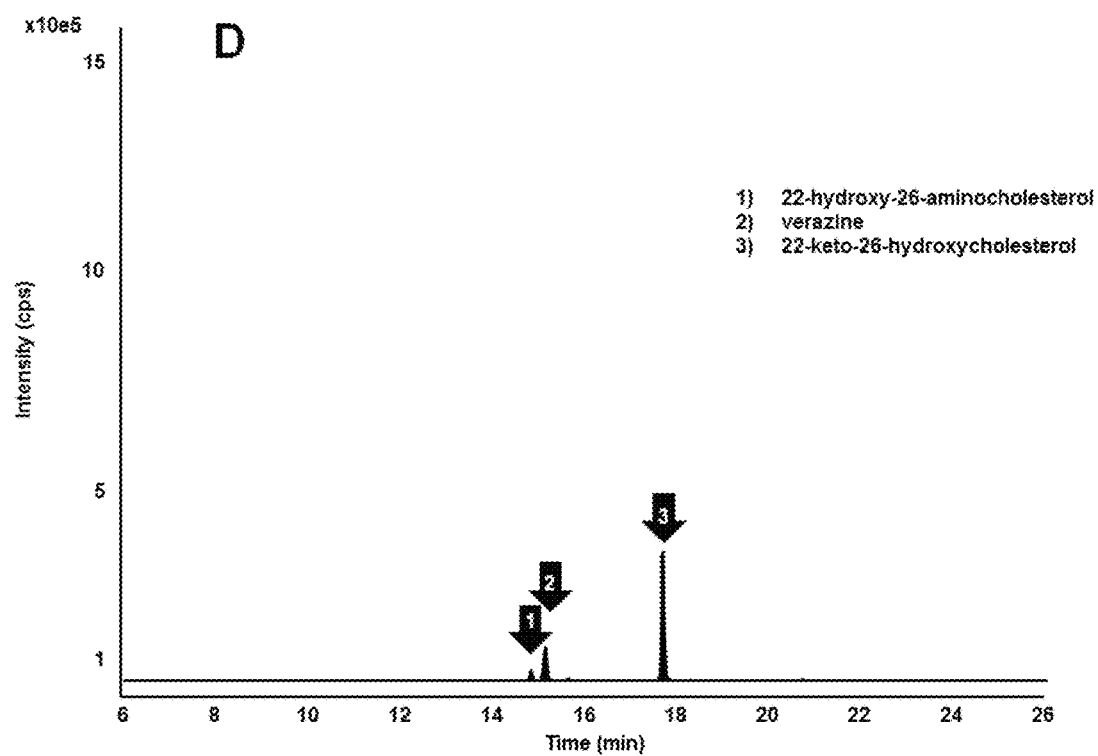

22-Hydroxycholesterol-26-al transaminase produced the same product in the presence or absence of 22-hydroxy-26-aminocholesterol 22-oxidase (FIG. 4A; C). 22-Hydroxycholesterol-26-al transaminase, therefore, did not require a 22-ketone moiety on the substrate. When cholesterol 22-hydroxylase acted in the presence of 22-hydroxycholesterol 26-hydroxylase/oxidase, several side products were made in addition to 22,26-dihydroxycholesterol (FIG. 11A). This included 22-keto-26-hydroxycholesterol, 22-hydroxycholesterol-26-al and two other products. Since an amino group was not added to the 22-ketone moiety of 22-keto-26-hydroxycholesterol, 22-keto-26-hydroxycholesterol most likely does not participate in the steroid alkaloid pathway. The short lived and highly reactive 22-hydroxycholesterol-26-al must be the substrate of the 22-hydroxycholesterol-26-al transaminase. Once the amino group is transferred to the C-26 aldehyde, 22-hydroxy-26-aminocholesterol 22-oxidase oxidizes the C-22-hydroxyl moiety to a ketone, and cyclization to verazine spontaneously occurs (FIG. 4C).

Figure 17:
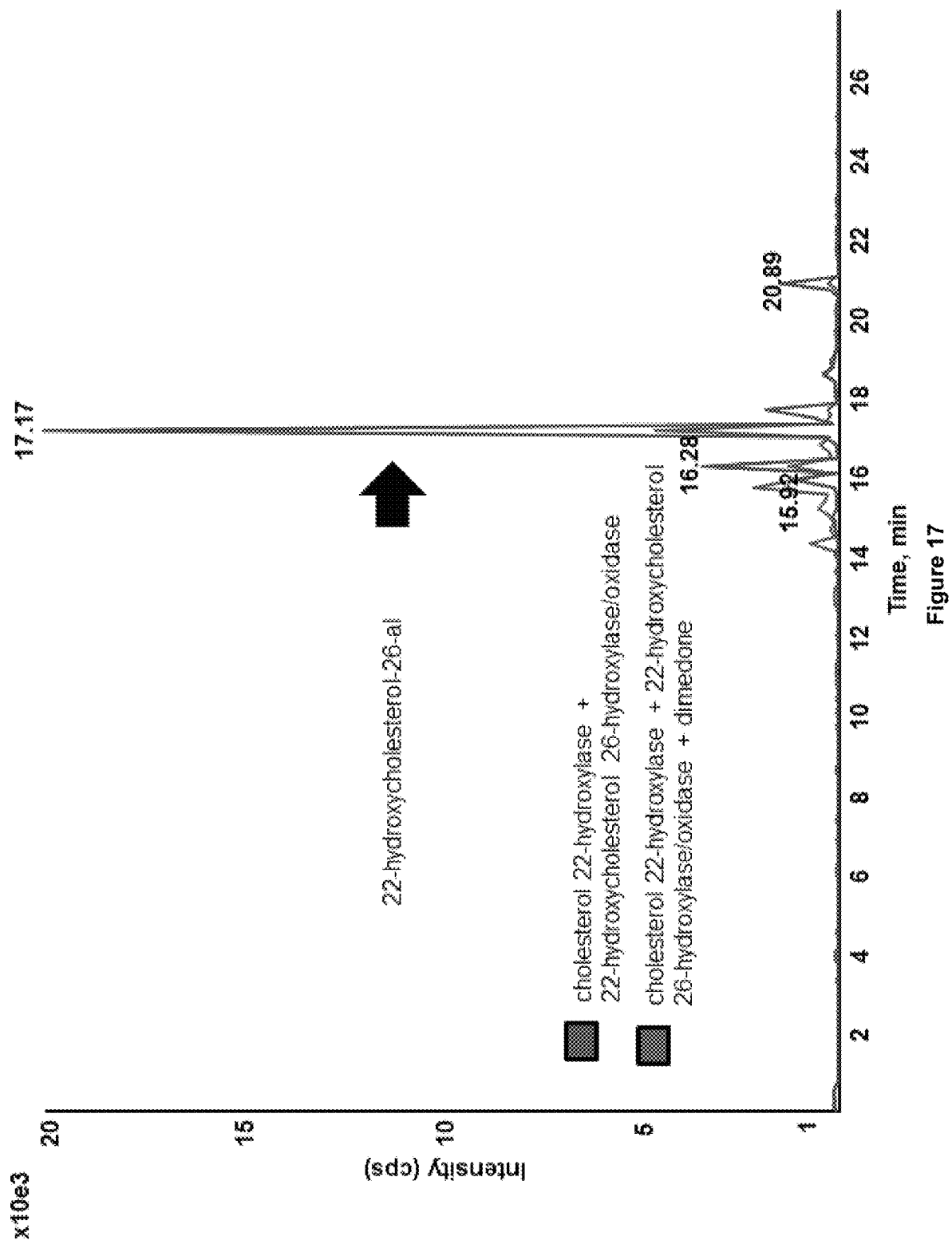

Evidence of the short-lived intermediate 22-hydroxycholesterol-26-al was obtained with a dimedone aldehyde trapping experiment (FIG. 17). The dimedone derivative could not be identified, however, a reduction in enzymatic product was observed in the presence of dimedone. The amino group is added prior to oxidation of the C-22 hydroxyl group, therefore the amino group must be transferred to the C-26 aldehyde. The structure of the predicted cyclic imine verazine was supported by borohydride reduction of the double bond (FIG. 18) and exact mass analysis as demonstrated by high resolution MS (FIGS. 12A and 12B).

The biosynthetic pathway proposed herein (FIG. 5) is consistent with an hypothesized pathway presented in earlier studies of steroidal alkaloids in the genus *Veratrum*. In further support of the proposed pathway, selected biosynthetic intermediates were detected in *V. californicum* extracts by LC-MS/MS (FIGS. 6A and 6B). The accumulation of these intermediates follows the same pattern as cyclopamine (FIG. 2). Verazine has also been detected in steroid alkaloid producing *Veratrum* species and was previously hypothesized an intermediate in steroidal alkaloid biosynthesis.

Site of Steroid Alkaloid Biosynthesis in *V. californicum*

A comparison was made between biosynthetic gene expression profiles and cyclopamine accumulation in *V. californicum* (FIG. 7). A pattern emerged that indicates that biosynthetic genes are most highly expressed in root, spring rhizome and bulb tissue, while steroid alkaloid accumulation is highest in spring and fall rhizome. Moreover, the higher level of cyclopamine in fall rhizome compared to spring rhizome indicates an accumulation of the steroid alkaloid during rhizome growth in summer.

FIGS. 6A and 6B show a comparison of the relative quantity of each detectable intermediate to the transcript level of the corresponding biosynthetic enzyme. Each gene expression value and metabolite accumulation value is expressed as a percent of the total for comparison. Interestingly, in all cases, the percent of gene expression and metabolite accumulation are similar in root and spring rhizome, but fall rhizome has significantly more metabolite relative to transcript level; the opposite is true for bulb, comparable with the accumulation pattern of cyclopamine. The biosynthetic intermediates were below limits of detection in bulb, so transport of these metabolites is plausible. Accumulation of these metabolites in fall rhizome and low gene expression suggests the rhizome may be used in metabolite storage for the plant. *Veratrum californicum* rarely seeds and new growth is mainly established by rhizome, generating evolutionary pressure for its protection.

Evolution of Steroid Alkaloid Biosynthesis

Recently, a biosynthetic pathway was proposed for steroid glycoalkaloids in *S. lycopersicum*. The pathway shares many similar reactions as the proposed cyclopamine pathway in *V. californicum* (FIG. 5), but some key differences emerge. In *S. lycopersicum*, initial transformations of cholesterol include C-22 hydroxylation followed by C-26 hydroxylation and closure of the E-ring. Oxidation at C-26, then transamination at that position occurs next. In conjunction with our results, previous work on steroid alkaloid formation in *Veratrum* does not support E-ring closure prior to aldehyde formation and transamination. Verazine production requires formation of the F-ring following transamination; prior to E-ring closure. If the pathway was identical to that proposed in *S. lycopersicum*, the E-ring closure prior to amination would not allow for the formation of verazine.

The contrasting pathways may be explained by the phylogenetic relationship of these enzymes. FIG. 8 shows a phylogenetic analysis of select cytochrome P450 enzymes including several involved in steroid metabolism and FIG. 9 shows the phylogenetic relationship of selected plant GABA transaminases. Cholesterol 22-hydroxylase in *V. californicum* and GAME7, the proposed cholesterol 22-hydroxylase in *S. lycopersicum*, do not share a recent common ancestor and appear evolutionarily distinct. Each shows only 20% identity at the amino acid level; the same for 26-hydroxylase in *S. lycopersicum* (GAME8) and *V. californicum* 22-hydroxycholesterol 26-hydroxylase/oxidase. GAME4, the *S. lycopersicum* enzyme that performs oxidation at position 26 does not cluster near 22-hydroxy-26-aminocholesterol 22-oxidase or 22-hydroxycholesterol 26-hydroxylase/oxidase of *V. californicum*. These relationships do not appear to be due to the evolutionary distinction between monocot and eudicots, as *V. californicum* cholesterol 22-hydroxylase and 22-hydroxy-26-aminocholesterol 22-oxidase share common ancestor cytochrome P450 enzymes from both classes of plants. Both of these enzymes cluster closer to the CYP90B1s from *Arabidopsis thaliana* and *S. lycopersicum*. The *Arabidopsis* CYP90B1 was shown to hydroxylate cholesterol, as well as other steroids in brassinosteroid metabolism. The relationship of the *V. californicum* enzymes and the CYP90B1s may be indicative of *Veratrum* alkaloid biosynthesis evolution deriving from the brassinosteroid pathway.

The phylogenetic relationship of GABA transaminases shows evidence of a potential polyploidy event that led to the duplication and subsequent neo-functionalization of the GABA transaminase genes. The *V. californicum* 22-hydroxycholesterol-26-al transaminase that incorporates nitrogen into 22-hydroxycholesterol-26-al does not cluster closely with the *S. lycopersicum* GABA transaminase isozyme 2 involved in steroid alkaloid biosynthesis as seen in FIG. 9, despite 64% identity. Due to the potential function and sequence homology, the inventors decided to test whether *S. lycopersicum* GABA transaminase isozyme 2 can incorporate nitrogen into 22-hydroxycholesterol-26-al. As seen in FIGS. 4A, 4B, 4C and 4D, it was demonstrated that *S. lycopersicum* GABA transaminase isozyme 2 was able to transaminate 22-hydroxycholesterol-26-al to 22-hydroxy-26-aminocholesterol with subsequent cyclization to verazine. The *S. lycopersicum* GABA transaminase isozyme 2 was used as query to BLAST© the *V. californicum* transcriptome, and interestingly, the best hit was another transaminase, contig VC674. VC674, designated GABA transaminase 2, annotated as a GABA transaminase with 68% identity to *S. lycopersicum* GABA transaminase isozyme 2 and 69% identity to *V. californicum* 22-hydroxycholesterol-26-al transaminase at the amino acid level. Despite the homology to *V. californicum* 22-hydroxycholesterol-26-al transaminase and *S. lycopersicum* GABA transaminase isozyme 2, GABA transaminase 2 was unable to catalyze the reaction (FIGS. 19A and 19B). The V *californicum* 22-hydroxycholesterol-26-al transaminase shows closer homology to other monocot GABA transaminases and to *Amborella*, which predates the monocot/eudicot division. These phylogenetic trees support a unique and independent evolution of the pathway to steroid alkaloids in *Veratrum* compared to tomato.

The *S. lycopersicum* genes recently identified in steroid alkaloid biosynthesis were found to cluster on chromosomes 7 and 12. Homologs in potato were also found to cluster. Although the genome sequence of *V. californicum* is not yet available, it would facilitate identification of the remainder of the pathway should these biosynthetic genes also cluster.

Besides engineering the cyclopamine and/or verazine-derived metabolite pathway(s) in higher plants and algae in order to obtain cyclopamine and/or verazine-derived metabolites economically and in high yield, the present disclosure also encompasses cyclopamine and/or verazine-derived metabolite production in plant cell cultures, cell-free extracts, production in organisms such as transgenic fungi, yeasts, bacteria such as *E. coli* and *B. subtilis*, and the use of immobilized enzymes, etc. In certain embodiments, the methods and compounds of the present disclosure may be used to regulate proliferation of cells and/or cell death in vitro and/or in vivo such as in the treatment of malignant disorders of the head, neck, nasal cavity, paranasal sinuses, nasopharynx, oral cavity, oropharynx, larynx, hypopharynx, salivary glands, paragangliomas, pancreas, stomach, skin, esophagus, liver and biliary tree, bone, intestine, colon, rectum, ovaries, prostate, lung, breast, lymphatic system, blood, bone marrow central nervous system, or brain.

Those skilled in the art will recognize, or be able to ascertain using no more than routine experimentation, many equivalents to the specific embodiments of the disclosure specifically described herein. Such equivalents are intended to be encompassed within the scope of the following claims.

What is claimed is:

1. A transgenic plant or plant cell, yeast cell, insect cell, or bacterial cell that produces a verazine-derived metabolite, the transgenic plant or plant cell, yeast cell, insect cell, or bacterial cell comprising within its genome, and expressing, four heterologous nucleotide sequences, wherein the heterologous nucleotide sequences encode for: (i) a cholesterol 22-hydroxylase enzyme having at least about 95% sequence identity to SEQ ID NO: 2; (ii) a 22-hydroxycholesterol 26-hydroxylase/oxidase enzyme having at least about 95% sequence identity to SEQ ID NO: 6; (iii) a 22-hydroxy-26-aminocholesterol 22-oxidase enzyme having at least about 95% sequence identity to SEQ ID NO: 20; and (iv) a γ-aminobutyrate transaminase enzyme that comprises an amino acid sequence having at least about 95% sequence identity to SEQ ID NO: 16.

2. The transgenic plant or plant cell, yeast cell, insect cell, or bacterial cell of claim 1, wherein the cholesterol 22-hydroxylase enzyme comprises the amino acid sequence of SEQ ID NO: 2; the 22-hydroxycholesterol 26-hydroxylase/oxidase enzyme comprises the amino acid sequence of SEQ ID NO: 6; the 22-hydroxy-26-aminocholesterol 22-oxidase enzyme comprises the amino acid sequence of SEQ ID NO: 20; and the γ-aminobutyrate transaminase enzyme comprises the amino acid sequence of SEQ ID NO: 16.

3. The transgenic plant or plant cell, yeast cell, insect cell, or bacterial cell of claim 2, wherein said heterologous nucleotide sequences are SEQ ID NO: 1 (encoding the cholesterol 22-hydroxylase enzyme), SEQ ID NO: 5 (encoding the 22-hydroxycholesterol 26-hydroxylase/oxidase enzyme), SEQ ID NO: 19 (encoding the 22-hydroxy-26-aminocholesterol 22-oxidase enzyme), and SEQ ID NO: 15 (encoding the γ-aminobutyrate transaminase enzyme).

4. The transgenic plant or plant cell, yeast cell, insect cell, or bacterial cell of claim 1, selected from the group consisting of a species of *Brachypodium*, a species of *Setaria*, a species of *Populus*, tobacco, corn, rice, soybean, cassava, canola (rapeseed), wheat, peanut, palm, coconut, safflower, sesame, cottonseed, sunflower, flax, olive, safflower, sugarcane, castor bean, switchgrass, *Miscanthus, Camelina sativa, Papaver somniferum*, and *Jatropha*.

5. The transgenic plant or plant cell, yeast cell, insect cell, or bacterial cell of claim 4, wherein one or more of said heterologous nucleotide sequences encoding an enzyme is codon-optimized for expression in said transgenic plant.

6. A method of making a transgenic plant or plant cell, yeast cell, insect cell, or bacterial cell, the method comprising the steps of:
 (i) inserting into the genome of a plant cell or plant cell, yeast cell, insect cell, or bacterial cell at least four heterologous nucleotide sequences comprising:
   (i) a promoter sequence operably linked for expression to a nucleotide sequence coding for a cholesterol 22-hydroxylase enzyme that comprises an amino acid sequence having at least about 95% sequence identity to SEQ ID NO: 2;
   (ii) a promoter sequence operable linked for expression to a nucleotide sequence coding for a 22-hydroxycholesterol 26-hydroxylase/oxidase enzyme that comprises an amino acid sequence having at least about 95% sequence identity to SEQ ID NO: 6;
   (iii) a promoter sequence operable linked for expression to a nucleotide sequence coding for a 22-hydroxy-26-aminocholesterol 22-oxidase enzyme that comprises an amino acid sequence having at least about 95% sequence identity to SEQ ID NO: 20; and
   (iv) a promoter sequence operably linked for expression to a nucleotide sequence coding for a γ-aminobutyrate transaminase enzyme that comprises an amino acid sequence having at least about 95% sequence identity to SEQ ID NO: 16;
 (ii) obtaining a transformed cell comprising said four heterologous nucleotide sequences; and
 (iii) regenerating from said transformed cell a genetically transformed plant or a plurality of genetically transformed cells, wherein said genetically transformed plant or said plurality of genetically transformed cells produce a verazine-derived metabolite.

7. The method of claim 6, wherein the transgenic plant or plant cell, yeast cell, insect cell, or bacterial cell is selected from the group consisting of a species of *Brachypodium*, a species of *Setaria*, a species of *Populus*, tobacco, corn, rice, soybean, cassava, canola (rapeseed), wheat, peanut, palm, coconut, safflower, sesame, cottonseed, sunflower, flax, olive, safflower, sugarcane, castor bean, switchgrass, *Miscanthus, Camelina sativa, Papaver somniferum*, and *Jatropha*.

8. The method of 7, wherein one or more of said heterologous nucleotide sequences encoding an enzyme is codon-optimized for expression in said transgenic plant.

9. The method of claim 6, wherein the transgenic plant or plant cell, yeast cell, insect cell, or bacterial cell is a yeast cell.

10. The method of claim 9, wherein one or more of said heterologous nucleotide sequences encoding an enzyme is codon-optimized for expression in yeast.

11. The method of claim 6, wherein the cholesterol 22-hydroxylase enzyme comprises the amino acid sequence of SEQ ID NO: 2; the 22-hydroxycholesterol 26-hydroxylase/oxidase enzyme comprises the amino acid sequence of SEQ ID NO: 6; the 22-hydroxy-26-aminocholesterol 22-oxidase enzyme comprises the amino acid sequence of SEQ ID NO: 20; and the γ-aminobutyrate transaminase enzyme comprises the amino acid sequence of SEQ ID NO: 16.

12. The method of claim 11, wherein the transgenic plant or plant cell, yeast cell, insect cell, or bacterial cell is a yeast cell.

13. The method of claim 12, wherein one or more of said heterologous nucleotide sequences encoding an enzyme is codon-optimized for expression in yeast.

14. The method of claim 6, wherein said heterologous nucleotide sequences encoding an enzyme are SEQ ID NO: 1 (encoding the cholesterol 22-hydroxylase enzyme), SEQ ID NO: 5 (encoding the 22-hydroxycholesterol 26-hydroxylase/oxidase enzyme), SEQ ID NO: 19 (encoding the 22-hydroxy-26-aminocholesterol 22-oxidase enzyme), and SEQ ID NO: 15 (encoding the γ-aminobutyrate transaminase enzyme).

15. The transgenic plant or plant cell, yeast cell, insect cell, or bacterial cell of claim 1 that is a yeast cell.

16. The transgenic plant or plant cell, yeast cell, insect cell, or bacterial cell of claim 15, wherein one or more of said heterologous nucleotide sequences encoding an enzyme is codon-optimized for expression in yeast.

17. The transgenic plant or plant cell, yeast cell, insect cell, or bacterial cell of claim 2 that is a yeast cell.

18. The transgenic plant or plant cell, yeast cell, insect cell, or bacterial cell of claim 17, wherein one or more of said heterologous nucleotide sequences encoding an enzyme is codon-optimized for expression in yeast.

19. The transgenic plant or plant cell, yeast cell, insect cell, or bacterial cell of claim 3, that is a yeast cell.

20. The transgenic plant or plant cell, yeast cell, insect cell, or bacterial cell of claim 2, selected from the group consisting of a species of *Brachypodium*, a species of *Setaria*, a species of *Populus*, tobacco, corn, rice, soybean, cassava, canola (rapeseed), wheat, peanut, palm, coconut, safflower, sesame, cottonseed, sunflower, flax, olive, safflower, sugarcane, castor bean, switchgrass, *Miscanthus, Camelina sativa, Papaver somniferum*, and *Jatropha*.

* * * * *